US011124801B2

(12) United States Patent
Coles et al.

(10) Patent No.: US 11,124,801 B2
(45) Date of Patent: Sep. 21, 2021

(54) GENES, CONSTRUCTS AND MAIZE EVENT DP-202216-6

(71) Applicant: PIONEER HI-BRED INTERNATIONAL, INC., Johnston, IA (US)

(72) Inventors: Nathan David Coles, Woodland, CA (US); Olga Danilevskaya, Middleton, WI (US); Jeffrey Habben, Urbandale, IA (US); Mary A Rupe, Altoona, IA (US); Jeffrey R Schussler, Marion, IA (US); Bo Shen, Johnston, IA (US); Benjamin P Weers, Polk City, IA (US); Jingrui Wu, Johnston, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 40 days.

(21) Appl. No.: 16/386,373

(22) Filed: Apr. 17, 2019

(65) Prior Publication Data
US 2019/0320607 A1    Oct. 24, 2019

Related U.S. Application Data

(60) Provisional application No. 62/741,529, filed on Oct. 4, 2018, provisional application No. 62/659,579, filed on Apr. 18, 2018.

(51) Int. Cl.
*C12N 15/82* (2006.01)
*C12Q 1/6895* (2018.01)

(52) U.S. Cl.
CPC ....... *C12N 15/8261* (2013.01); *C12Q 1/6895* (2013.01); *C12N 15/8286* (2013.01); *C12Q 2600/13* (2013.01); *C12Q 2600/158* (2013.01)

(58) Field of Classification Search
None
See application file for complete search history.

(56) References Cited

U.S. PATENT DOCUMENTS

| | | |
|---|---|---|
| 5,811,536 A | 9/1998 | Yanofsky |
| 5,859,326 A | 1/1999 | An |
| 5,990,386 A | 11/1999 | An |
| 6,025,483 A | 2/2000 | Yanofsky |
| 6,025,543 A | 2/2000 | Yanofsky |
| 6,229,068 B1 | 5/2001 | Yanofsky et al. |
| 6,995,302 B1 | 2/2006 | Kojima et al. |
| 2002/0129403 A1 | 9/2002 | Yanofsky et al. |
| 2004/0019933 A1 | 1/2004 | Podila et al. |
| 2005/0091717 A1 | 4/2005 | Amasino et al. |
| 2005/0108791 A1 | 5/2005 | Edgerton |
| 2005/0241014 A1 | 10/2005 | Colliver et al. |
| 2006/0206965 A1 | 9/2006 | Gleissner et al. |
| 2006/0248612 A1 | 11/2006 | Vancanneyt et al. |
| 2007/0006344 A1 | 1/2007 | Nuccio et al. |
| 2007/0033671 A1 | 2/2007 | Jiang et al. |
| 2007/0039070 A1 | 2/2007 | Bloksberg et al. |
| 2007/0048756 A1 | 3/2007 | Mei et al. |
| 2007/0250945 A1 | 10/2007 | Sung et al. |
| 2007/0270578 A1 | 11/2007 | Frankard |
| 2009/0089896 A1 | 4/2009 | Wiig et al. |
| 2009/0217406 A1 | 8/2009 | Puzio et al. |
| 2009/0255013 A1 | 10/2009 | Alvarez-Venegas et al. |
| 2010/0024065 A1 | 1/2010 | Mullet et al. |
| 2010/0175146 A1* | 7/2010 | Bruce .................. C07K 14/415 800/278 |
| 2010/0186114 A1 | 7/2010 | Spangenberg et al. |
| 2010/0218273 A1 | 8/2010 | Bruce |
| 2010/0257637 A1 | 10/2010 | Shirley et al. |
| 2011/0093985 A1 | 4/2011 | Suzuki et al. |
| 2012/0042411 A1 | 2/2012 | Malcuit et al. |
| 2013/0263324 A1 | 10/2013 | Lassner et al. |
| 2014/0130202 A1 | 5/2014 | Gantet et al. |
| 2015/0128309 A1 | 5/2015 | Sastry-Dent et al. |
| 2015/0240253 A1 | 8/2015 | McGonigle et al. |
| 2015/0284737 A1 | 10/2015 | Bate et al. |
| 2016/0138036 A1 | 5/2016 | Park et al. |
| 2016/0237447 A1 | 8/2016 | Abad et al. |
| 2016/0304890 A1 | 10/2016 | Song et al. |

FOREIGN PATENT DOCUMENTS

| | | |
|---|---|---|
| WO | 9400582 | 1/1994 |
| WO | 9746078 | 12/1997 |
| WO | 9904003 | 1/1999 |
| WO | 9947654 | 9/1999 |
| WO | 200032780 | 6/2000 |
| WO | 200119995 | 3/2001 |

(Continued)

OTHER PUBLICATIONS

Kim et al. Genome-wide analysis of Agrobacterium T-DNA integration sites in the *Arabidopsis* genome generated under non-selective conditions. Plant J. Sep. 2007;51(5):779-91. Epub Jun. 3, 20070. (Year: 2007).*

Rice, Elena A. et al: "Expression of a Truncated ATHB17 Protein in Maize Increases Ear Weight at Silking"; PLOS ONE; Apr. 2014; vol. 9, Issue 4; pp. 1-21.

Schilling, Susanne et al: "MADS-box genes and crop domestication: the jack of all traits"; Journal of Experimental Botany; 2018; vol. 69, No. 7; pp. 1447-1469.

Schwarz-Sommer, Zsuzsanna et al: "Genetic Control of Flower Development by Homeotic Genes in Antirrhinum majus"; Science Articles; Nov. 16, 1990; vol. 250; pp. 931-936.

Shcherbo, Dmitry et al: "Far-red fluorescent tags for protein imaging in living tissues"; Biochem J; Mar. 15, 2009; vol. 418; pp. 567-574.

(Continued)

*Primary Examiner* — Cynthia E Collins

(57) ABSTRACT

The compositions and methods disclosed relate to DNA compositions, plant cells, seeds, plant parts that relate to maize plants with increased grain yield trait. Also provided are assays for detecting the presence of the maize DP-202216-6 event based on the DNA sequence of the recombinant construct inserted into the maize genome and the DNA sequences flanking the insertion site. Kits and conditions useful in conducting the assays are provided.

6 Claims, 5 Drawing Sheets

Specification includes a Sequence Listing.

(56) References Cited

FOREIGN PATENT DOCUMENTS

| WO | 200229028 | 4/2002 |
|---|---|---|
| WO | 200233091 | 4/2002 |
| WO | 2004035797 | 4/2004 |
| WO | 2007110600 | 10/2007 |
| WO | 2007132789 | 11/2007 |
| WO | 2014208508 | 12/2014 |

OTHER PUBLICATIONS

Shi, Jinrui et al: "Overexpression of ARGOS Genes Modifies Plant Sensitivity to Ethylene, Leading to Improved Drought Tolerance in Both *Arabidopsis* and Maize"; Plant Physiology; Sep. 2015; vol. 169; pp. 266-282.
Shore, Paul et al: "The MADS-box family of transcription factors"; European Journal of Biochemistry; 1995; vol. 229; pp. 1-13.
Song, Guo-Qing et al: "Overexpression of the MADS-box gene K-domain increases the yield potential of blueberry"; Plant Science; 2018; vol. 276; pp. 22-31.
Song, Zing-Xin et al: "Soybean GmbZIP123 gene enhances lipid content in the seeds of transgenic *Arabidopsis* plants"; Journal of Experimental Botany; 2013; vol. 64, No. 14; pp. 4329-4341.
Sun, Jindong et al: "Interactions of Nitrate and CO2 Enrichment on Growth, Carbohydrates, and Rubisco in *Arabidopsis* Starch Mutants. Significance of Starch and Hexose"; Plant Physiology; Nov. 2002; vol. 130; pp. 1573-1583.
Sun, Jindong et al: "Inconsistency of mesophyll conductance estimate causes theinconsistency for the estimates of maximum rate of Rubiscocarboxylation among the linear, rectangular and non-rectangularhyperbola biochemical models of leaf photosynthesis—A case study ofCO2enrichment and leaf aging effects in soybean"; Plant Science; 2014; vol. 226; pp. 49-60.
Tang, Weining et al: "Binding Site Selection for the Plant MADS Domain Protein AGL15, An In Vitro and In Vivo Study"; The Journal of Biological Chemistry; Jul. 25, 2003; vol. 278, No. 30; pp. 28154-28159.
Theissen, Gunter et al: "Floral quartets"; Nature; Jan. 25, 2001; vol. 409; pp. 469-471.
Thompson, Julie D. et al: "The CLUSTAL_X windows interface: flexible strategies for multiple sequence alignment aided by quality analysis tools"; Nucleic Acids Research; 1997; vol. 25, No. 24; pp. 4876-4882.
Trachsel, Samuel et al: "Interrelations among Early Vigor, Flowering Time, Physiological Maturity, and Grain Yield in Tropical Maize (*Zea mays* L.) under Multiple Abiotic Stresses"; Crop Science; 2017; vol. 57; pp. 229-242.
Wang, Lin et al: "Comparative analyses of C4 and C3 photosynthesis in developing leaves of maize and rice"; Nature Biotechnology; Nov. 2014; vol. 32, No. 11; pp. 1158-1170.
Wei, Bo et al: "Functional divergence of two duplicated D-lineage MADS-box genes BdMADS2 and BdMADS4 from Brachypodium distachyon"; Journal of Plant Physiology; 2013; vol. 170; pp. 424-431.
Wei, Bo et al: "Novel microRNAs uncovered by deep sequencing of sm.all RNA transcriptomes in bread wheat (*Triticum aestivum* L.) and *Brachypodium distachyon* (L.) Beauv"; Functional & Integrative Genomics; 2009; vol. 9: pp. 499-511.
Xing, Shuping et al: "Techniques for the Analysis of Protein-Protein Interactions in Vivo"; Plant Physiology; Jun. 2016; vol. 171; pp. 727-758.
Yadav, M. R. et al: "Strategies for improving nitrogen use efficiency: A review"; Agricultural Reviews; 2017; vol. 38; pp. 29-40.
Yoo, Sang-Dong et al: "*Arabidopsis mesophyll* protoplasts: a versatile cell system for transient gene expression analysis"; Nature Protocols; 2007; vol. 2, No. 7; pp. 1565-1573.
Yu, Y. T. et al: "Identification of a major quantitative trait locus for ear size induced by space flight in sweet corn"; Genetics and Molecular Research; 2014; vol. 13; pp. 3069-3078.

Zastrow-Hayes, Gina M. et al: "Southern-by-Sequencing: A Robust Screening Approach for Molecular Characterization of Genetically Modified Crops"; The Plant Genome; Mar. 13, 2015; vol. 8, No. 1; pp. 1-15.
Zhang, Hanma et al: "An *Arabidopsis* MADS Box Gene That Controls Nutrient-Induced Changes in Root Architecture"; Science; Jan. 16, 1998; vol. 279; pp. 407-409.
Zhang, Yong et al: "Model-based Analysis of ChIP-Seq (MACS)"; Genome Biology; 2008; vol. 9; pp. R137.1-R137-9.
Zhao, Qiong et al: "MADS-box genes of maize: frequent targets of selection during domestication"; Genetics Research (Cambridge); Feb. 2011; vol. 93; pp. 65-75.
Zhao, Yang et al: "Whole-genome survey and characterization of MADS-box gene family in maize and sorghum"; Plant Cell Tissue Organ Culture; 2011; vol. 105; pp. 159-173.
Zheng, Zhi-Liang et al: "Carbon and nitrogen nutrient balance signaling in plants"; Plant Signaling & Behavior; Jul. 2009; vol. 4; pp. 584-591.
International Search Report and Written Opinion of the International Searching Authority for PCT/US2019/027599, dated Sep. 16, 2019.
An, Gynheung et al: "Functional Analysis of the 3' Control Region of the Potato Wound-Inducible Proteinase Inhibitor II Gene"; The Plant Cell; Jan. 1989; vol. 1; pp. 115-122.
Andorf, Carson M et al: "MaizeGDB update: new tools, data and interface for the maize model organism database"; Nucleic Acids Research, 2016, vol. 44, pp. D1195-D1201.
Ashburner, Michael et al: "Gene Ontology: tool for the unification of biology"; Nat Genet.; May 2000 ; vol. 25; No. (1): pp. 25-29.
Assem, Shireen K et al: "Comparison of the efficiency of some novel maize promoters in monocot and dicot plants"; Arab J. Biotech; Jan. 2002; vol. 5; No. (1); pp. 57-66.
Becker, Annette et al: "The major clades of MADS-box genes and their role in the development and evolution of flowering plants"; Molecular Phylogenetics and Evolution; Apr. 2003; vol. 29; pp. 464-489.
Castiglioni, Paolo et al: "Bacterial RNA Chaperones Confer Abiotic Stress Tolerance in Plants and Improved Grain Yield in Maize under Water-Limited Conditions"; Plant Physiology; Jun. 2008; vol. 147; pp. 446-455.
Century, Karen et al: "Regulating the Regulators: The Future Prospects for Transcription-Factor-Based Agricultural Biotechnology Products"; Plant Physiology; May 2008; vol. 147; pp. 20-29.
Christensen, Alan H. et al: "Maize polyubiquitin genes: structure, thermal perturbation of expression and transcript splicing, and promoter activity following transfer to protoplasts by electroporation"; Plant Molecular Biology; 1992; vol. 18; pp. 675-689.
Coen, Enrico S. et al: "The war of the whorls: genetic interactions controlling flower development"; Nature; Sep. 5, 1991; vol. 353 pp. 31-37.
De Pater, B. Sylvia et al: "The promoter of the rice gene GOSZ is active in various different monocot tissues and binds rice nuclear factor ASF-I"; The Plant Journal; 1992; vol. 2; pp. 837-844.
De Veau, Edward J. et al: "Photorespiratory Rates in Wheat and Maize as Determined by 0-Labeling"; Plant Physiol.; 1989; vol. 90; pp. 500-511.
Du, Zhou et al: "agriGO: a GO analysis toolkit for the agricultural community"; Nucleic Acids Research; 2010; vol. 38; pp. W64-W70.
Echarte, L. et al: "Kernel Number Determination in Argentinean Maize Hybrids Released between 1965 and 1993"; Crop Science; 2004; vol. 44; pp. 1654-1661.
Egli, D. B. et al: "Is There a Role for Sink Size in Understanding Maize Population—Yield Relationships?"; Crop Science; 2015; vol. 55; pp. 2453-2462.
Ferrandiz, Cristina et al: "Redundant regulation of meristem identity and plant architecture by Fruitfull, APETALA1 and Cauliflower"; Development; 2000; vol. 127; pp. 725-734.
Fornara, Fabio et al: "Functional Characterization of OsMADS18, a Member of the AP1/SQUA Subfamily of MADS Box Genes"; Plant Physiology; Aug. 2004; vol. 135; pp. 2207-2219.
Gan, Yinbo et al: "Nutritional regulation of ANR1 and other root-expressed MADS-box genes in *Arabidopsis thaliana*"; Planta; 2005; vol. 222; pp. 730-742.

(56) References Cited

OTHER PUBLICATIONS

Gilmore, A. R. et al: "ASReml User Guide Release 3.0"; 2009; NSW Department of Industry and Investment; HP1 1ES; pp. 1-372.
Gilmore, Arthur R. et al: "Average Information REML: An Official Algorithm for Variance Parameter Estimation in Linear Mixed Models"; Biometrics; Dec. 1995; vol. 51; pp. 1440-1450.
Gramzow, Lydia et al: "A hitchhiker's guide to the MADS world of plants"; Genome Biology; Jun. 28, 2010; vol. 11; pp. 1-11.
Guo, Siyi et al: "The interaction between OsMADS57 and OsTB1 modulates rice tillering via DWARF14"; Nature Communications; Mar. 2013; vol. 4; pp. 1-12.
Habben, Jeffrey E. et al: "Transgenic alteration of ethylene biosynthesis increases grain yield in maize under field drought-stress conditions"; Plant Biotechnology Journal; 2014; vol. 12; pp. 685-693.
Hartmann, Ulrike et al: "Molecular cloning of SVP: a negative regulator of the floral transition in *Arabidopsis*"; The Plant Journal; 2000; vol. 21; pp. 351-360.
Hensgens, Lambert A. M. et al: "Transient and stable expression of gusA fusions with rice genes in rice, barley and perennial ryegrass"; Plant Molecular Biology; 1993; vol. 23; pp. 643-669.
Hoagland, D. R. et al: "The Water-Culture Method for Growing Plants without Soil"; California Agricultural Experiment Station; 1950; vol. 347; pp. 1-32.
Horstman, Anneke et al: "A Cautionary Note on the Use of Split-YFP/BiFC in Plant Protein-Protein Interaction Studies"; International Journal of Molecular Sciences; 2014; vol. 15; pp. 9628-9643.
Huang, Baowen et al: "Overexpression of the class D MADS-box gene SI-AGL11 impacts fleshy tissue differentiation and structure in tomato fruits"; Journal of Experimental Botany; 2017; vol. 68, No. 17; pp. 4869-4884.
Huang, Hai et al: "DNA Binding Properties of Two *Arabidopsis* MADS Domain Proteins: Binding Consensus and Dimer Formation"; The Plant Cell; Jan. 1996; vol. 8; 81-94.
Jiao, Yinping et al: "Improved maize reference genome with single-molecule technologies"; Nature; Jun. 22, 2017; vol. 546; pp. 524-539.
Kanai, R. et al: "Separation of Mesophyll Protoplasts and Bundle Sheath Cells from Maize Leaves for Photosynthetic Studies"; Plant Physiol.; 1973; vol. 51; pp. 1133-1137.
Krall, John P. et al: "Protection of Pyruvate,Pi Dikinase from Maize against Cold Lability by Compatible Solutes"; Plant Physiol.; 1989; vol. 89; pp. 280-285.
Langmead, Ben et al: "Ultrafast and memory-efficient alignment of short DNA sequences to the human genome"; Genome Biology; 2009; vol. 10; pp. 1-10.
Lawit, Shai J. et al: "Transgenic manipulation of plant embryo sacs tracked through cell-type-specific fluorescent markers: cell labeling, cell ablation, and adventitious embryos"; Plant Reprod; 2013; vol. 26; pp. 125-137.
Lawit, Shai J. et al: "Maize DELLA Proteins dwarf plant8 and dwarf plant9 as Modulators of Plant Development"; Plant Cell Physiol.; vol. 51; pp. 1854-1868.
Li, Bo et al: "RSEM: accurate transcript quantification from RNA-Seq data with or without a reference genome"; BMC Bioinformatics; 2011; vol. 12; pp. 1-16.
Li, Qunhua et al: "Measuring Reproducibility of High-Throughput Experiments"; The Annals of Applied Statistics; 2011; vol. 5, No. 3; pp. 1752-1779.
Love, Michael I. et al: "Moderated estimation of fold change and dispersion for RNA-seq data with DESeq2"; Genome Biology; 2014; vol. 15; pp. 1-21.
Mandel, M. Alejandra et al: "The *Arabidopsis* AGL8 MADS Box Gene 1s Expressed in Inflorescence Meristems and 1s Negatively Regulated by APETALAI"; The Plant Cell; Nov. 1995; vol. 7; pp. 1763-1771.
Masclaux-Daubresse, Celine et al: "Nitrogen uptake, assimilation and remobilization in plants: challenges for sustainable and productive agriculture"; Annals of Botany; 2010; vol. 105; pp. 1141-1157.
Matias-Hernandez, Luis et al: "VERDANDI Is a Direct Target of the MADS Domain Ovule Identity Complex and Affects Embryo Sac Differentiation in *Arabidopsis*"; The Plant Cell; Jun. 2010; vol. 22; pp. 1702-1715.
Maxwell, Kate et al: "Chlorophyll fluorescence—a practical guide"; Journal of Experimental Botany; Apr. 2000; vol. 51, No. 345; pp. 659-668.
Munster, T. et al: "Maize MADS-Box Genes Galore"; Maydica; 2002; vol. 47; pp. 287-301.
Nelson, Donald E. et al: "Plant nuclear factor Y (NF-Y) B subunits confer drought tolerance and lead to improved corn yields on water-limited acres"; PNAS; Oct. 16, 2007; vol. 104; pp. 16450-16455.
Nuccio, Michael L. et al: "Expression of trehalose-6-phosphate phosphatase in maize ears improves yield in well-watered and drought conditions"; Nature Biotechnology; Aug. 2015; vol. 33, No. 8; pp. 862-869.
Onouchi, Hitoshi et al: "Mutagenesis of Plants Overexpressing CONSTANS Demonstrates Novel Interactions among *Arabidopsis* Flowering-Time Genes"; The Plant Cell; Jun. 2000; vol. 12; pp. 885-900.
Ort, Donald R. et al: "Redesigning photosynthesis to sustainably meet global food and bioenergy demand"; PNAS; Jul. 14, 2015; vol. 112, No. 28; pp. 8529-8536.
Perez-Rodriguez, Paulino et al: "PInTFDB: updated content and new features of the plant transcription factor database"; Nucleic Acids Research; 2010; vol. 38; pp. D822-D827.
Purugganan, Michael D. et al: "Molecular Evolution of Flower Development: Diversification of the Plant MADS-Box Regulatory Gene Family"; Genetics Society of America; May 2015; vol. 140; pp. 345-356.
Rabara, Roel C. et al: "The Potential of Transcription Factor-Based Genetic Engineering in Improving Crop Tolerance to Drought"; OMICS a Journal of Integrative Biology; 2014; vol. 18, No. 10; pp. 601-614.
Ray D K et al: "Yield trends insufficient to double global crop production by 2050"; PLoS ONE; Jun. 19, 2013; vol. 8; pp. 1-2.
Catron, et al.; (2019) "Petition for Determination of Nonregulated Status for Enhanced Grain Yield Potential and Glufosinate-ammonium Resistant DP202216 Maize"; Jun. 3, 2019; USDA-APHIS.

\* cited by examiner

```
  1  MGRGPVQLRR IENKINRQVT FSKRRNGLLK KAHEISVLCD AEVALIVFST KGKLYEYSSH
 61  SSMEGILERY QRYSFEERAV LNPSIEDQAN WGDEYVRLKS KLDALQKSQR QLLGEQLSSL
121  TIKELQQLEQ QLDSSLKHIR SRKNQLMFDS ISALQKKEKA LTDQNGVLQK FMEAEKEKNK
181  ALMNAQLREQ QNGASTSSPS LSPPIVPDSM PTLNIGPCQH RGAAESESEP SPAPAQANRG
241  NLPPWMLRTV K
```

GENES, CONSTRUCTS AND MAIZE EVENT DP-202216-6

REFERENCE TO SEQUENCE LISTING SUBMITTED ELECTRONICALLY

The official copy of the sequence listing is submitted electronically via EFS-Web as an ASCII formatted sequence listing with a file named "7768USNP_ST25.txt" created on Apr. 18, 2018, and having a size of 51 kilobytes and is filed concurrently with the specification. The sequence listing contained in this ASCII formatted document is part of the specification and is herein incorporated by reference in its entirety.

FIELD

Embodiments disclosed herein relate to the field of plant molecular biology, specifically to DNA constructs for increasing yield of a plant. Embodiments disclosed herein more specifically relate to maize plants, genes, cells, seeds, plant parts, DNA, processed plant product and constructs relating to maize event DP-202216-6 and methods and compositions thereof.

BACKGROUND

Corn is an agriculturally important crop and serves as a food and feed source for animal, human, and industrial uses. Increased grain yield may be achieved in maize plants by a variety of ways, including expression of a transgene to increase grain yield in addition to improved breeding. Performance of a transgene in a plant including the agronomic parameters, may be impacted by a variety of factors such as the use of expression elements including promoter/regulatory elements, the genomic location of the insert sequence, copy number of the inserted transgene and genetic (germplasm) and environmental factors such as soil, temperature, light and moisture. The identification of constructs, testing of orthologs and transformation events that result in increased grain yield of a maize plant at a commercially relevant level in the field are the result of a substantial and significant developmental effort towards product advancement. Accordingly, it would be desirable to have maize plants that demonstrate increased grain yield.

SUMMARY

A corn seed includes Event DP-202216-6, wherein said seed comprises a DNA molecule selected from the group consisting of SEQ ID NOS: 7, 8, 9, 10, 11, 12, 13, 14 and a combination thereof, wherein a representative sample of corn event DP-202216-6 seed of has been deposited with American Type Culture Collection (ATCC) with Accession No. PTA-124653. In some embodiments, a corn plant, or part thereof, grown from the seed of PTA-124653 is described herein.

A maize plant stably transformed with a recombinant polynucleotide sequence encoding a polypeptide comprising an amino sequence that is at least 90%, 93% 95%, 97%, 98% or 99% identical to SEQ ID NO: 1, wherein the maize plant exhibits increased grain yield compared to a control maize plant not containing the recombinant polynucleotide. In some embodiments, the recombinant polynucleotide is operably linked to a weak heterologous constitutive regulatory element. In some embodiments, the grain yield is at least about three bushels/acre when compared to the control maize plant, wherein the maize plant and the control maize plant are grown in a field under normal crop growing conditions. In some embodiments, the grain yield in the field range from about 2 to about 8 bu/acre when compared to the control population of maize plants grown in a population density of about 20,000 to about 50,000 plants per acre. In some embodiments, the weak heterologous constitutive regulatory element is a maize GOS2 promoter. In some embodiments, the amino acid sequence is at least 95% identical to SEQ ID NO: 1 and the maize plant comprises a polynucleotide encoding a polypeptide that provides herbicide tolerance and a polynucleotide that encodes a polypeptide or an RNA sequence that provides resistance to one or more insect pests. Maize seed produced from the maize plant described herein exhibit yield improvement characteristics. In an embodiment, the regulatory element comprises a heterologous intron element.

A recombinant polynucleotide construct includes a polynucleotide encoding a polypeptide comprising an amino acid sequence that is at least 90%, 93% 95%, 97%, 98% or 99% identical to SEQ ID NO: 1, wherein the polynucleotide is operably linked to a heterologous regulatory element. In some embodiments, the amino acid sequence based on SEQ ID NO: 1 may have one or more variations including, insertion, deletion or substitution.

A method of increasing grain yield of a maize plant, the method comprising expressing a polynucleotide sequence encoding a polypeptide that is at least 90%, 93% 95%, 97%, 98% or 99% identical to SEQ ID NO: 1, wherein the polynucleotide is operably linked to a heterologous regulatory sequence; and growing the maize plant in a field to increase grain yield compared to a control maize plant not containing the polynucleotide operably linked to the heterologous regulatory sequence.

A method of producing a seed, the method comprising the following:
 (a) crossing a first plant with a second plant, wherein at least one of the first plant and the second plant comprises a recombinant DNA construct, wherein the recombinant DNA construct comprises a polynucleotide operably linked to at least one regulatory element, wherein the polynucleotide encodes a MADS protein having an amino acid sequence of at least 90% sequence identity, based on the Clustal V or Clustal W method of alignment, when compared to SEQ ID NO: 1; and
 (b) selecting a seed of the crossing of step (a), wherein the seed comprises the recombinant DNA construct.

A plant grown from the seed produced by the method described herein, wherein the plant exhibits increased yield, when compared to a control plant not comprising the recombinant DNA construct.

In some embodiments, a method of selecting a plant that exhibits increased yield the method comprises:
 (a) obtaining a plant, wherein the plant comprises in its genome a recombinant DNA construct comprising a polynucleotide operably linked to at least one regulatory element, wherein said polynucleotide encodes a MADS protein having an amino acid sequence of at least 90% sequence identity, based on the Clustal V or Clustal W method of alignment, when compared to SEQ ID NO: 1;
 (b) growing the plant in a field under conditions wherein the polynucleotide is expressed; and
 (c) selecting the plant of part that exhibits increased yield when compared to a control plant not comprising the recombinant DNA construct.

In some embodiments, the plant is selected from the group consisting of maize, soybean, sunflower, sorghum, canola, wheat, alfalfa, cotton, rice, barley, millet, sugar cane and switchgrass. In an embodiment, the amino acid sequence of the MADS protein comprises a sequence that is at least 99% identical to SEQ ID NO: 1.

A recombinant polynucleotide includes a polynucleotide sequence encoding a polypeptide having an amino acid sequence that is at least 95% identical to SEQ ID NO: 1, wherein the recombinant polynucleotide comprises a heterologous regulatory element. In some embodiments, a plant or seed includes the recombinant polynucleotide described herein.

A maize plant that exhibits increased expression of an endogenous polynucleotide encoding a polypeptide comprising a sequence that is at least 95% identical to SEQ ID NO: 1, wherein the increased expression is due to a heterologous regulatory element. In some embodiments, the heterologous regulatory element is a plant-derived enhancer element. In some embodiments, the heterologous regulatory element is a weak constitutive promoter element. In some embodiments, the maize plant is an inbred or a hybrid plant.

In some embodiments, the maize plant includes a second polypeptide that provides herbicide tolerance and a third polypeptide that provides insect resistance.

A recombinant DNA construct comprising an expression cassette, wherein the expression cassette in operable linkage includes a maize gos2 promoter; a maize ubiquitin gene 1 (ubiZM1) intron; a maize MADS box gene encoding the maize ZMM28 protein; a pinII terminator; a maize ubiquitin gene 1 (ubiZM1) promoter; a maize ubiquitin gene 1 (ubiZM1) 5' UTR; a maize ubiquitin gene 1 (ubiZM1) intron; a mo-pat gene; and a pinII terminator. In some embodiments, a plant includes the DNA construct described herein and the plant is a corn plant. In some embodiments, the plant includes the sequence that is at least 95% identical to the polynucleotide sequence set forth in SEQ ID NO: 6.

A corn plant, seed, cell or part thereof includes event DP-202216-6, wherein the event comprises the nucleotide sequence set forth in SEQ ID NO: 7 and SEQ ID NO: 8. In some embodiments, the event comprises the nucleotide sequence set forth in SEQ ID NO: 9 and SEQ ID NO: 10. In some embodiments, the event comprises the nucleotide sequence set forth in SEQ ID NO: 11 and SEQ ID NO: 12. In some embodiments, the event comprises the nucleotide sequence set forth in SEQ ID NO: 13 or SEQ ID NO: 14. In some embodiments, the plant part is selected from the group consisting of pericarp, pollen, ovule, flower, grain, shoot, root, stalk, silk, tassel, ear, and leaf tissue.

A corn plant, seed, cell or part thereof includes event DP-202216-6, wherein a representative sample of seed of said corn event has been deposited with American Type Culture Collection (ATCC) with Accession No. PTA-124653. In some embodiments, the plant part is selected from the group consisting of pericarp, pollen, ovule, flower, grain, shoot, root, stalk, silk, tassel, ear, and leaf tissue.

An isolated nucleic acid molecule includes a nucleotide sequence selected from the group consisting of SEQ ID NOS: 7, 8, 9, 10, 11, 12 and in some embodiments, an amplicon includes the nucleic acid sequence selected from the group consisting of SEQ ID NOS: 7, 8, 9, 10, 11, 12 and full length complements thereof. In some embodiments, the amplicon is less than about 500 bp, 1 kb, 1.5 kb, 2.0 kb, 3.0 kb, 5.0 kb, and 10 kb.

A biological sample derived from corn event DP-202216-6 plant, tissue, or seed, wherein said sample comprises a nucleotide sequence which is or is complementary to a sequence selected from the group consisting of SEQ ID NOS: 7, 8, 9, 10, 11, and 12, wherein said nucleotide sequence is detectable in said sample using a nucleic acid amplification or nucleic acid hybridization method, wherein a representative sample of said corn event DP-202216-6 seed of has been deposited with American Type Culture Collection (ATCC) with Accession No. PTA-124653. In some embodiments, the biological sample comprises plant, tissue, or portions of seed, pericarp of seed of transgenic corn event DP-202216-6. In some embodiments, the biological sample is a DNA sample extracted from the transgenic corn plant event DP-202216-6, and wherein said DNA sample comprises one or more of the nucleotide sequences selected from the group consisting of SEQ ID NOS: 7, 8, 9, 10, 11, 12, and the complements thereof. In some embodiments, the biological sample is selected from the group consisting of corn flour, corn meal, corn syrup, corn oil, corn starch, and cereals manufactured in whole or in part to contain corn by-products, wherein said biological sample comprises a detectable amount of said nucleotide sequence.

An extract derived from corn event DP-202216-6 plant, tissue, or seed and comprising a nucleotide sequence which is or is complementary to a sequence selected from the group consisting of SEQ ID NOS: 7, 8, 9, 10, 11, and 12 wherein a representative sample of said corn event DP-202216-6 seed has been deposited with American Type Culture Collection (ATCC) with Accession No. PTA-124653. In some embodiments, said nucleotide sequence is detectable in said extract using a nucleic acid amplification or nucleic acid hybridization method. In some embodiments, a composition is selected from the group consisting of corn flour, corn meal, corn syrup, corn oil, corn starch, and cereals manufactured in whole or in part to contain corn by-products, wherein said composition comprises a detectable amount of said nucleotide sequence.

A method of producing hybrid corn seeds the method includes:
  a) sexually crossing a first inbred corn line comprising a nucleotide sequence selected from the group consisting of SEQ ID NOS: 7, 8, 9, 10, 11, and 12 and a second inbred line having a different genotype;
  b) growing progeny from said crossing; and
  c) harvesting the hybrid seed produced thereby.

In some embodiments, the first inbred corn line is a female parent or the first inbred corn line is a male parent.

A method for producing a corn plant that exhibits increased grain yield in a field, the method comprising:
  a) sexually crossing a first parent corn plant with a second parent corn plant, wherein said first or second parent corn plant comprises Event DP-202216-6 DNA, thereby producing a plurality of first generation progeny plants;
  b) selfing the first generation progeny plant, thereby producing a plurality of second generation progeny plants; and
  c) selecting from the second generation progeny plants that comprise the event DP-202216-6, a plant that exhibits increased grain yield in the field compared to a control corn plant not comprising the event DP-202216-6.

In some embodiments, the event DP-202216-6 comprises a recombinant DNA construct and wherein the event DP-202216-6 comprises encodes a polypeptide that is at least 99% identical to SEQ ID NO: 1.

A method of producing hybrid corn seeds comprising:
  a) sexually crossing a first inbred corn line comprising the DNA construct described herein with a second inbred line not comprising the DNA construct; and
  b) harvesting the hybrid seed produced thereby.

In some embodiments, the step of backcrossing includes backcrossing the second generation progeny plant that comprises corn event DP-202216-6 to the parent plant that lacks the corn event DP-202216-6, thereby producing a backcross progeny plant that exhibits increased grain yield compared to a control corn plant not comprising the event DP-202216-6.

A method for producing a corn plant that exhibits increased grain yield, said method includes:
  a) sexually crossing a first parent corn plant with a second parent corn plant, wherein said first or second parent corn plant is a corn event DP-202216-6 plant, thereby producing a plurality of first generation progeny plants;
  b) selecting a first generation progeny plant that exhibits increased grain yield;
  c) backcrossing the first generation progeny plant of step (b) with the parent plant that lacks the corn event DP-202216-6, thereby producing a plurality of backcross progeny plants; and
  d) selecting from the backcross progeny plants, a plant that exhibits increased grain yield;
     wherein the selected backcross progeny plant of step (d) comprises a sequence selected from the group consisting of SEQ ID NOS: 7, 8, 9, 10, 11 and 12.

In some embodiments, the plants of the first parent corn plant are the female parents or male parents. Hybrid seed are produced by the methods described herein.

A method of determining zygosity of DNA of a corn plant comprising corn event DP-202216-6 in a biological sample comprising:
  a) contacting said sample with a first pair of DNA molecules and a second distinct pair of molecules such that: (i) when used in a nucleic acid amplification reaction comprising corn event DP-202216-6 DNA, produces a first amplicon that is diagnostic for corn event DP-202216-6, and (ii) when used in a nucleic acid amplification reaction comprising corn genomic DNA other than DP-202216-6 DNA, produces a second amplicon that is diagnostic for corn genomic DNA other than DP-202216-6 DNA;
  b) performing a nucleic acid amplification reaction; and
  c) detecting the first and second amplicons so produced, wherein detection of the presence of the first and second amplicons indicates that said sample is heterozygous for corn event DP-202216-6 DNA, wherein detection of the first amplicon indicates that said sample is homozygous for corn event DP-202216-6 DNA.

In some embodiments, the first pair of DNA molecules comprise primer pairs that amplify a DNA fragment that comprises a sequence selected from the group consisting of SEQ ID NOS: 7, 8, 9, 10, 11, 12 and reverse complements thereof. In some embodiments, the first and second pair of DNA molecules comprise a detectable label. In some embodiments, the detectable label is a fluorescent label. In some embodiments, the detectable label is covalently associated with one or more of the primer molecules. In some embodiments, the primer pair comprises SEQ ID NOS: 15 and 16.

A method of detecting the presence of a nucleic acid molecule that is unique to or discriminates event DP-202216-6 in a sample, the method includes:
  a) contacting the sample with a pair of primers or a probe that, when used in a nucleic-acid amplification reaction with genomic DNA from event DP-202216-6 produces a nucleic acid molecule that is diagnostic for event DP-202216-6;
  b) performing a nucleic acid amplification reaction, thereby producing the nucleic acid molecule that is diagnostic for event DP-202216-6; and
  c) detecting the nucleic acid molecule that is diagnostic for event DP-202216-6.

In some embodiments, the nucleic acid molecule that is diagnostic for event DP-202216-6 is an amplicon produced by the nucleic acid amplification chain reaction. In some embodiments, the probe comprises a detectable label. In some embodiments, the detectable label is a fluorescent label. In some embodiments, the detectable label is covalently associated with the probe.

A plurality of polynucleotide primers comprising one or more polynucleotides comprising a length of at least 10 contiguous bases which target event DP-202216-6 DNA template in a sample to produce an amplicon diagnostic for event DP-202216-6 as a result of a polymerase chain reaction amplification method. In some embodiments, polynucleotide primers are characterized by:
  a) a first polynucleotide primer comprises at least 10 contiguous nucleotides of a nucleotide sequence selected from the group consisting of nucleotides 1-425 of SEQ ID NO: 31, nucleotides 1-417 of SEQ ID NO: 32, and the complements thereof; and
  b) a second polynucleotide primer comprises at least 10 contiguous nucleotides from nucleotides of SEQ ID NO: 6, or the complements thereof.

In some embodiments, the polynucleotide primers are characterized by:
  a) the first polynucleotide primer comprises a polynucleotide sequence comprising SEQ ID NO: 15 and the complements thereof; and
  b) the second polynucleotide primer comprises a polynucleotide sequence comprising SEQ ID NO: 16 and the complements thereof.

In some embodiments, said first primer and said second primer are at least 18 nucleotides.

A method of detecting the presence of DNA corresponding to the DP-202216-6 event in a sample, the method includes:
  a) contacting the sample comprising maize DNA with a polynucleotide probe that hybridizes under stringent hybridization conditions with DNA from maize event DP-202216-6 and does not hybridize under said stringent hybridization conditions with a non-DP-202216-6 maize plant DNA;
  b) subjecting the sample and probe to stringent hybridization conditions; and
  c) detecting hybridization of the probe to the DNA; wherein detection of hybridization indicates the presence of the DP-202216-6 event.

A kit for detecting a nucleic acid that is unique to event DP-202216-6 includes at least one nucleic acid molecule of sufficient length of contiguous polynucleotides to function as a primer or probe in a nucleic acid detection method, and which upon amplification of or hybridization to a target nucleic acid sequence in a sample followed by detection of the amplicon or hybridization to the target sequence, are diagnostic for the presence of the nucleic acid sequence unique to event DP-202216-6 in the sample. In some embodiments, the nucleic acid molecule comprises a nucleotide sequence from SEQ ID NO: 7 or 8.

In some embodiments, the nucleic acid molecule is a primer pair comprising a pair of polynucleotide sequences, each comprising at least 10 contiguous bases, wherein the primer pair amplifies a junction sequence of the event DP-202216-6, the junction comprising a polynucleotide sequence selected from the group consisting of SEQ ID NOS: 7, 8, 9, 10, 11, 12, 13, 14, 31, and 32 and complements thereof.

A commodity product produced from a transgenic corn plant comprising event DP-202216-6 and comprising a recombinant DNA molecule comprising a nucleotide sequence selected from the group consisting of SEQ ID NOS: 7, 8, 9, 10, 11, 12, 13, 14, 31, and 32, and full complements thereof, wherein detection of said recombinant DNA molecule in a sample derived from said commodity product is determinative that said commodity product was produced from said transgenic corn plant comprising event DP-202216-6. In some embodiments, the commodity product is selected from the group consisting of whole or processed seeds, animal feed, oil, meal, flour, flakes, bran, biomass, and fuel products.

A method of producing a commodity product, the method comprising: (a) obtaining a corn plant or part thereof comprising transgenic corn event DP-202216-6; and (b) producing a corn commodity product from the corn plant or part thereof.

An antibody generated to target a polypeptide produced from the event DP-202216-6, wherein the polypeptide is produced by a heterologous regulatory element and comprises an amino acid sequence that is at least 99% identical to SEQ ID NO: 1. In some embodiments, the antibody is a monoclonal antibody and comprises a detectable label.

A method of increasing grain yield of a population of maize plants in a field, the method comprising growing a population of maize plants comprising Event DP-202216-6 in a field and thereby increasing grain yield of the population of maize plants compared to a control plant not comprising the Event DP-202216-6. In some embodiments, the population of maize plants are grown under abiotic stress. In some embodiments, the abiotic stress is low nitrogen. In some embodiments, when grown under low nitrogen conditions, the population of maize plants comprising the Event DP-202216-6 exhibits yield stability compared to the control population of plants grown under low nitrogen. In some embodiments, the low nitrogen is about 25% to about 75% reduction in the amount of nitrogen normally applied to grow hybrid corn plants in the field. In some embodiments, the reduction in nitrogen applied to field ranges from about 5% to about 10%, 20%, 30%, 40%, 50%, 60% or 70% compared to a normal application of nitrogen.

According to some embodiments, compositions and methods are provided for identifying a novel corn plant designated DP-202216-6 (ATCC Deposit Number PTA-124653). The methods are based on primers or probes which specifically recognize the 5' and/or 3' flanking sequence of DP-202216-6. DNA molecules are provided that comprise primer sequences that when utilized in a PCR reaction will produce amplicons unique to the transgenic event DP-202216-6. In one embodiment, the corn plant and seed comprising these molecules is contemplated. Further, kits utilizing these primer sequences for the identification of the DP-202216-6 event are provided.

Additional embodiments relate to the specific flanking sequence of DP-202216-6 as described herein, which can be used to develop specific identification methods for DP-202216-6 in biological samples. More particularly, the disclosure relates to the 5' and/or 3' flanking regions of DP-202216-6, which can be used for the development of specific primers and probes. Further embodiments relate to identification methods for the presence of DP-202216-6 in biological samples based on the use of such specific primers or probes.

According to another embodiment, methods of detecting the presence of DNA corresponding to the corn event DP-202216-6 in a sample are provided. Such methods comprise: (a) contacting the sample comprising DNA with a DNA primer set, that when used in a nucleic acid amplification reaction with genomic DNA extracted from corn event DP-202216-6 produces an amplicon that is diagnostic for corn event DP-202216-6, respectively; (b) performing a nucleic acid amplification reaction, thereby producing the amplicon; and (c) detecting the amplicon. In some aspects, the primer set comprises SEQ ID NO: 15 and/or 16, a polynucleotide that detects at least one junction sequence selected from the group consisting of SEQ ID NOS: 7-12 and a combination thereof.

According to another embodiment, methods of detecting the presence of a DNA molecule corresponding to the DP-202216-6 event in a sample, such methods comprising: (a) contacting the sample comprising DNA extracted from a corn plant with a DNA probe molecule that hybridizes under stringent hybridization conditions with DNA extracted from corn event DP-202216-6 and does not hybridize under the stringent hybridization conditions with a control corn plant DNA; (b) subjecting the sample and probe to stringent hybridization conditions; and (c) detecting hybridization of the probe to the DNA. More specifically, a method for detecting the presence of a DNA molecule corresponding to the DP-202216-6 event in a sample, such methods, consisting of (a) contacting the sample comprising DNA extracted from a corn plant with a DNA probe molecule that consists of sequences that are unique to the event, e.g. junction sequences, wherein said DNA probe molecule hybridizes under stringent hybridization conditions with DNA extracted from corn event DP-202216-6 and does not hybridize under the stringent hybridization conditions with a control corn plant DNA; (b) subjecting the sample and probe to stringent hybridization conditions; and (c) detecting hybridization of the probe to the DNA.

In addition, a kit and methods for identifying event DP-202216-6 in a biological sample which detects a DP-202216-6 specific region are provided.

DNA molecules are provided that comprise at least one junction sequence of DP-202216-6; wherein a junction sequence spans the junction between heterologous DNA inserted into the genome and the DNA from the corn cell flanking the insertion site, i.e. flanking DNA, and is diagnostic for the DP-202216-6 event.

According to another embodiment, methods of producing a corn plant that comprise the steps of: (a) sexually crossing a first parental corn line comprising the expression cassettes disclosed herein, which increase yield, and a second parental corn line that lacks such constructs, thereby producing a plurality of progeny plants; and (b) selecting a progeny plant that shows increase in yield. Such methods may optionally include the further step of back-crossing the progeny plant to the second parental corn line to producing a true-breeding corn plant that exhibits yield increase.

Another embodiment further relates to a DNA detection kit for identifying maize event DP-202216-6 in biological samples. The kit includes a first primer or probe which specifically amplifies or detects the 5' or 3' flanking region of DP-202216-6, and a second primer or probe which specifically amplifies or detects a sequence within the insert DNA of DP-202216-6, respectively, or within the flanking DNA, for use in a PCR identification protocol. A further embodiment relates to a kit for identifying event DP-202216-6 in biological samples, which kit comprises a specific probe having a sequence which corresponds or is complementary to, a sequence having between 80% and 100% sequence identity with a specific region of event DP-202216-6. The sequence of the probe corresponds to a specific region comprising part of the 5' or 3' flanking region of event DP-202216-6. In some embodiments, the first or second primer or an appropriate probe comprises SEQ ID NO: 15, 16, 17, 18, 19, 20 and reverse complements thereof.

The methods and kits encompassed by the embodiments disclosed herein can be used for different purposes such as, but not limited to the following: to identify event DP-202216-6 in plants, plant material or in products such as, but not limited to, food or feed products (fresh or processed) comprising, or derived from plant material; additionally or alternatively, the methods and kits can be used to identify transgenic plant material for purposes of segregation between transgenic and non-transgenic material; additionally or alternatively, the methods and kits can be used to determine the quality of plant material comprising maize event DP-202216-6. The kits may also contain the reagents and materials necessary for the performance of the detection method.

A further embodiment relates to the DP-202216-6 maize plant or its parts, including, but not limited to, pollen, ovules, pericarp, vegetative cells, the nuclei of pollen cells, and the nuclei of egg cells of the corn plant DP-202216-6 and the progeny derived thereof. In another embodiment, specific amplicons produced from the maize plant and seed of DP-202216-6 are included.

DESCRIPTION OF THE DRAWINGS

FIG. 2A shows protein sequence SEQ ID NO: 1, the amino acid sequence that includes the. MADS box, Intervening (solid underline), K-box (dotted line), and C-terminal domains.

BRIEF DESCRIPTION OF THE SEQUENCES

Figure 1:
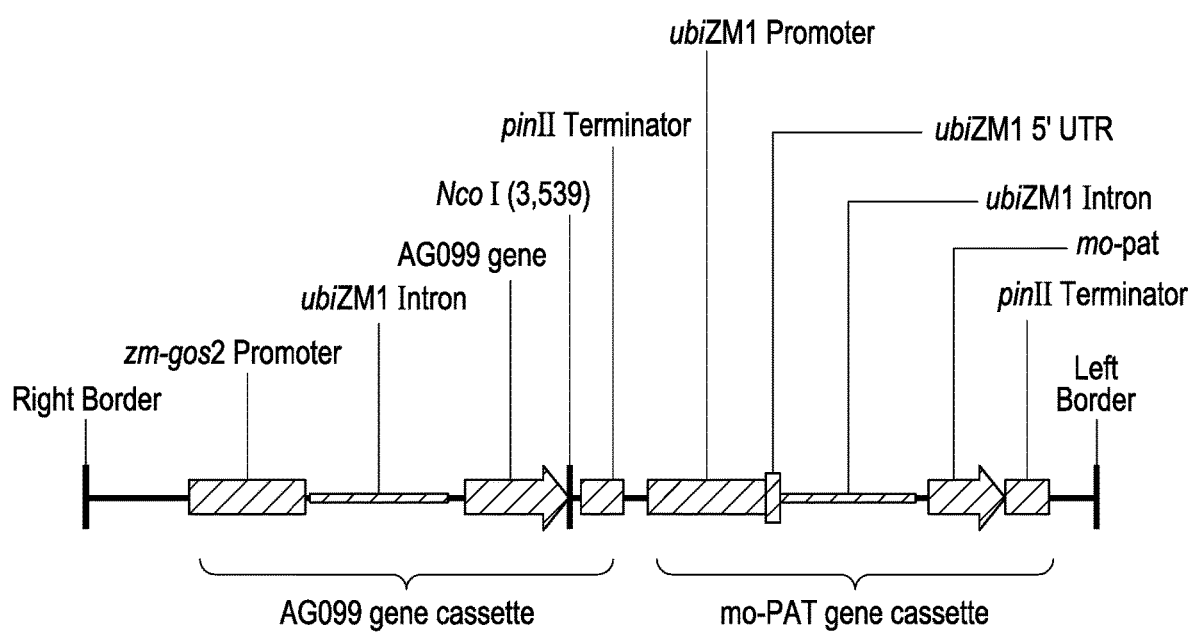
FIG. 1. depicts a schematic diagram of the T-DNA region that is integrated into the genome of the maize plant to generate Event DP-202216-6. The size of the T-DNA is 7,470 bp.

The disclosure can be more fully understood from the following detailed description and the accompanying drawings and Sequence Listing that form a part of this application.

The sequence descriptions summarize the Sequence Listing attached hereto, which is hereby incorporated by reference. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219(2):345-373 (1984).

TABLE 1

| Sequence Listing Description | |
|---|---|
| SEQ ID NO: | Description |
| 1 | Maize MADS-box protein 28 |
| 2 | Maize MADS-box protein 28 DNA |
| 3 | Maize GOS2 promoter |
| 4 | ubiZM1 Intron |
| 5 | T-DNA region of AG099 plasmid |
| 6 | Insert DNA for AG099 |
| 7 | Event DP-202216-6 junction sequence 5' end (10 bp; 5 bp genomic + 5 bp insert) |
| 8 | Event DP-202216-6 junction sequence 3' end (10 bp; 5 bp genomic + 5 bp insert) |
| 9 | Event DP-202216-6 junction sequence 5' end (20 bp; 10 bp genomic + 10 bp insert) |
| 10 | Event DP-202216-6 junction sequence 3' end (20 bp; 10 bp genomic + 10 bp insert) |
| 11 | Event DP-202216-6 junction sequence 5' end (30 bp; 15 bp genomic + 15 bp insert) |
| 12 | Event DP-202216-6 junction sequence 3' end (30 bp; 15 bp genomic + 15 bp insert) |
| 13 | Event DP-202216-6 insert DNA + genomic flanking sequence (10 bp on both 5' and 3' ends) |
| 14 | Event DP-202216-6 insert DNA + genomic flanking sequence (20 bp on both 5' and 3' ends) |
| 15 | DP-2Ø2216-6 forward primer |
| 16 | DP-2Ø2216-6 reverse primer |
| 17 | DP-2Ø2216-6 probe |
| 18 | AG099 forward primer |
| 19 | AG099 reverse primer |

TABLE 1-continued

Sequence Listing Description

| SEQ ID NO: | Description |
|---|---|
| 20 | AG099 probe |
| 21 | mo-PAT forward primer |
| 22 | mo-PAT reverse primer |
| 23 | mo-PAT probe |
| 24 | DP-2Ø2216-6 assay amplicon sequence (105 bp) |
| 25 | AG099 assay amplicon sequence (93 bp) |
| 26 | mo-PAT assay amplicon sequence (76 bp) |
| 27 | hmg-A forward primer |
| 28 | hmg-A reverse primer |
| 29 | hmg-A probe |
| 30 | hmg-A assay amplicon sequence (79 bp) |
| 31 | 5' end 425 bp genomic + 10 bp junction DNA sequence |
| 32 | 3' end 10 bp junction + 407 bp genomic DNA sequence |

DETAILED DESCRIPTION

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof, and so forth. All technical and scientific terms used herein have the same meaning as commonly understood to one of ordinary skill in the art to which this disclosure belongs unless clearly indicated otherwise.

Compositions of this disclosure include a representative sample of seeds which was deposited as Patent Deposit No. PTA-124653 and plants, plant cells, and seed derived therefrom. Applicant(s) have made a deposit of at least 2500 seeds of maize event DP-202216-6 (Patent Deposit No. PTA-124653) with the American Type Culture Collection (ATCC), Manassas, Va. 20110-2209 USA, on Jan. 12, 2018. These deposits will be maintained under the terms of the Budapest Treaty on the International Recognition of the Deposit of Microorganisms for the Purposes of Patent Procedure. The seeds deposited with the ATCC on Jan. 12, 2018 were taken from a representative sample deposit maintained by Pioneer Hi-Bred International, Inc., 7250 NW 62$^{nd}$ Avenue, Johnston, Iowa 50131-1000. Access to this ATCC deposit will be available during the pendency of the application to the Commissioner of Patents and Trademarks and persons determined by the Commissioner to be entitled thereto upon request, in accordance with applicable laws and regulations. Upon issuance of a patent, this deposit of seed of maize Event DP-202216-6 is intended to meet all the necessary requirements of 37 C.F.R. §§ 1.801-1.809, and will be maintained in the ATCC depository, for a period of 30 years, or 5 years after the most recent request, or for the enforceable life of the patent, whichever is longer, and will be replaced if it becomes nonviable during that period. Unauthorized seed multiplication prohibited. The seed may be regulated under one or more applicable National, State or other local regulations and ordinances imposed by one or more competent governmental agencies.

As used herein, the term "corn" means *Zea mays* or maize and includes all plant varieties that can be bred with corn, including wild maize species.

As used herein, the terms "insect resistant" and "impacting insect pests" refers to effecting changes in insect feeding, growth, and/or behavior at any stage of development, including but not limited to: killing the insect; retarding growth; reducing reproductive capability; inhibiting feeding; and the like.

As used herein, the terms "pesticidal activity" and "insecticidal activity" are used synonymously to refer to activity of an organism or a substance (such as, for example, a protein) that can be measured by numerous parameters including, but not limited to, pest mortality, pest weight loss, pest attraction, pest repellency, and other behavioral and physical changes of a pest after feeding on and/or exposure to the organism or substance for an appropriate length of time. For example, "pesticidal proteins" are proteins that display pesticidal activity by themselves or in combination with other proteins.

As used herein, "insert DNA" refers to the heterologous DNA within the expression cassettes used to transform the plant material while "flanking DNA" can exist of either genomic DNA naturally present in an organism such as a plant, or foreign (heterologous) DNA introduced via the transformation process which is extraneous to the original insert DNA molecule, e.g. fragments associated with the transformation event. A "flanking region" or "flanking sequence" as used herein refers to a sequence of at least 20 bp, for some embodiments, at least 50 bp, and up to 5000 bp, which is located either immediately upstream of and contiguous with or immediately downstream of and contiguous with the original foreign insert DNA molecule. Transformation procedures of the foreign DNA will result in transformants containing different flanking regions characteristic and unique for each transformant. When recombinant DNA is introduced into a plant through traditional crossing, its flanking regions will generally not be changed. Transformants will also contain unique junctions between a piece of heterologous insert DNA and genomic DNA, or two (2) pieces of genomic DNA, or two (2) pieces of heterologous DNA. A "junction" is a point where two (2) specific DNA fragments join. For example, a junction exists where insert DNA joins flanking DNA. A junction point also exists in a transformed organism where two (2) DNA fragments join together in a manner that is modified from that found in the native organism. "Junction DNA" refers to DNA that comprises a junction point. Two junction sequences set forth in this disclosure are the junction point between the maize genomic DNA and the 5' and the 3'end of the insert as set forth in one of SEQ ID NOS: 7-14, 31-32 (see Table 1 and the accompanying sequence listing for description).

In an embodiment, the junction sequences of Event DP-202216-6, for example, one or more SEQ ID NOS: 7-14, 31-32 may include polymorphisms (e.g., SNPs) or mutations that may occur spontaneously in the endogenous genomic region of the junction sequence. These may include insertion, deletion or substitution of one or more nucleotides in the junction sequence. Polynucleotide sequences that are at least 90%, 91%, 92%, 93%, 94%, 95%, 96%, 97%, 98%, and 99% to one or more of the junction sequences represented by one of SEQ ID NOS: 7-14, 31-32 are disclosed herein.

As used herein, "heterologous" in reference to a nucleic acid sequence is a nucleic acid sequence that originates from a foreign species, or, if from the same species, is substantially modified from its native form in composition and/or genomic locus by deliberate human intervention. For example, a promoter operably linked to a heterologous nucleotide sequence can be from a species different from that from which the nucleotide sequence was derived, or, if from the same species, the promoter is not naturally found operably linked to the nucleotide sequence. A heterologous protein may originate from a foreign species, or, if from the same species, is substantially modified from its original form by deliberate human intervention.

The term "regulatory element" refers to a nucleic acid molecule having gene regulatory activity, i.e. one that has the ability to affect the transcriptional and/or translational expression pattern of an operably linked transcribable polynucleotide. The term "gene regulatory activity" thus refers to the ability to affect the expression of an operably linked transcribable polynucleotide molecule by affecting the transcription and/or translation of that operably linked transcribable polynucleotide molecule. Gene regulatory activity may be positive and/or negative and the effect may be characterized by its temporal, spatial, developmental, tissue, environmental, physiological, pathological, cell cycle, and/or chemically responsive qualities as well as by quantitative or qualitative indications.

"Promoter" refers to a nucleotide sequence capable of controlling the expression of a coding sequence or functional RNA. In general, a coding sequence is located 3' to a promoter sequence. The promoter sequence comprises proximal and more distal upstream elements, the latter elements are often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different regulatory elements may direct the expression of a gene in different tissues or cell types, or at different stages of development, or in response to different environmental conditions. Promoters that cause a nucleic acid fragment to be expressed in most cell types at most times are commonly referred to as "constitutive promoters".

The "translation leader sequence" refers to a nucleotide sequence located between the promoter sequence of a gene and the coding sequence. The translation leader sequence is present in the fully processed mRNA upstream of the translation start sequence. The translation leader sequence may affect numerous parameters including, processing of the primary transcript to mRNA, mRNA stability and/or translation efficiency. Examples of translation leader sequences have been described (Turner and Foster (1995) *Mol. Biotechnol.* 3:225-236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

A DNA construct is an assembly of DNA molecules linked together that provide one or more expression cassettes. The DNA construct may be a plasmid that is enabled for self-replication in a bacterial cell and contains various endonuclease enzyme restriction sites that are useful for introducing DNA molecules that provide functional genetic elements, i.e., promoters, introns, leaders, coding sequences, 3' termination regions, among others; or a DNA construct may be a linear assembly of DNA molecules, such as an expression cassette.

The expression cassette contained within a DNA construct comprises the necessary genetic elements to provide transcription of a messenger RNA. The expression cassette can be designed to express in prokaryote cells or eukaryotic cells. Expression cassettes of the embodiments are designed to express in plant cells.

The DNA molecules disclosed herein are provided in expression cassettes for expression in an organism of interest. The cassette will include 5' and 3' regulatory sequences operably linked to a coding sequence. "Operably linked" means that the nucleic acid sequences being linked are contiguous and, where necessary to join two protein coding regions, contiguous and in the same reading frame. Operably linked is intended to indicate a functional linkage between a promoter and a second sequence, wherein the promoter sequence initiates and mediates transcription of the DNA sequence corresponding to the second sequence. The cassette may additionally contain at least one additional gene to be co-transformed into the organism. Alternatively, the additional gene(s) can be provided on multiple expression cassettes or multiple DNA constructs.

The expression cassette may include in the 5' to 3' direction of transcription: a transcriptional and translational initiation region, a coding region, and a transcriptional and translational termination region functional in the organism serving as a host. The transcriptional initiation region (i.e., the promoter) may be native or analogous, or foreign or heterologous to the host organism. Additionally, the promoter may be the natural sequence or alternatively a synthetic sequence. The expression cassettes may additionally contain 5' leader sequences in the expression cassette construct. Such leader sequences can act to enhance translation.

A transgenic "event" is produced by transformation of plant cells with a heterologous DNA construct(s), including a nucleic acid expression cassette that comprises a transgene of interest, the regeneration of a population of plants resulting from the insertion of the transgene into the genome of the plant, and selection of a particular plant characterized by insertion into a particular genome location. An event is characterized phenotypically by the expression of the transgene. At the genetic level, an event is part of the genetic makeup of a plant. The term "event" also refers to progeny produced by a sexual outcross between the transformant and another variety that include the heterologous DNA. Even after repeated back-crossing to a recurrent parent, the inserted DNA and flanking DNA from the transformed parent is present in the progeny of the cross at the same chromosomal location. The term "event" also refers to DNA from the original transformant comprising the inserted DNA and flanking sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

Corn plant containing event DP-202216-6 may be bred by first sexually crossing a first parental corn plant consisting of a corn plant grown from event DP-202216-6 corn plant and progeny thereof derived from transformation with the expression cassettes of the embodiments that increase yield when compared to a control plant, and a second parental corn plant that does not have such constructs, thereby producing a plurality of first progeny plants; and then selecting a first progeny plant that demonstrates yield increase; and selfing the first progeny plant, thereby producing a plurality of second progeny plants; and then selecting from the second progeny plants plant with yield increase.

As used herein, the term "plant" includes reference to whole plants, parts of plants, plant organs (e.g., leaves, stems, roots, etc.), seeds, plant cells, and progeny of same. In some embodiments, parts of transgenic plants comprise, for example, plant cells, protoplasts, tissues, callus, embryos as well as flowers, stems, fruits, leaves, and roots originating in transgenic plants or their progeny previously transformed with a DNA molecule disclosed herein, and therefore consisting at least in part of transgenic cells.

As used herein, the term "plant cell" includes, without limitation, seeds, suspension cultures, embryos, meristematic regions, callus tissue, leaves, roots, shoots, gametophytes, sporophytes, pollen, and microspores. The class of plants that may be used is generally as broad as the class of higher plants amenable to transformation techniques, including both monocotyledonous and dicotyledonous plants.

The present disclosure provides a commodity product that is derived from a corn plant comprising event DP-202216-6. As used herein, a "commodity product" generally refers to any composition or material that includes material derived or processed from a plant, seed, plant cell, or plant part comprising event DP-202216-6. Commodity products may be viable (e.g., seeds) or nonviable (e.g., corn meal). Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animal's consumption, oil, meal, flour, flakes, bran, fiber, milk, cheese, paper, cream, wine, ethanol, and any other food for human consumption; and biomasses and fuel products. Viable commodity products include but are not limited to seeds and plant cells. A plant comprising event DP-202216-6 can thus be used to manufacture any suitable commodity product obtainable from a corn plant. Such commodity product that is derived from the plants comprising event DP-202216-6 may contain a detectable amount of the specific and unique DNA corresponding to event DP-202216-6, and specifically may contain a detectable amount of a polynucleotide having a nucleotide sequence of at least 15 consecutive nucleotides of SEQ ID NOS: 9-14, at least 20 consecutive nucleotides of SEQ ID NOS: 9-14 and 31-32, at least 30 consecutive nucleotides of SEQ ID NOS: 9-14 and 31-32. Any standard method of detection for polynucleotide molecules may be used in the commodity product, including methods of detection disclosed herein.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (London) 327:70-73; U.S. Pat. No. 4,945,050, incorporated herein by reference). Additional transformation methods are disclosed below.

As used herein, the term "progeny" denotes the offspring of any generation of a parent plant which comprises corn event DP-202216-6.

Isolated polynucleotides disclosed herein may be incorporated into recombinant constructs, typically DNA constructs, which are capable of introduction into and replication in a host cell. Such a construct may be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., (1985; Supp. 1987) *Cloning Vectors: A Laboratory Manual*, Weissbach and Weissbach (1989) *Methods for Plant Molecular Biology*, (Academic Press, New York); and Flevin et al., (1990) *Plant Molecular Biology Manual*, (Kluwer Academic Publishers). Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

During the process of introducing an insert into the genome of plant cells, it is not uncommon for some deletions or other alterations of the insert and/or genomic flanking sequences to occur. Thus, the relevant segment of the plasmid sequence provided herein might comprise some minor variations. The same is true for the flanking sequences provided herein. Thus, a plant comprising a polynucleotide having some range of identity with the subject flanking and/or insert sequences is within the scope of the subject disclosure. Identity to the sequence of the present disclosure may be a polynucleotide sequence having at least 65% sequence identity, for some embodiments at least 70% sequence identity, for some embodiments at least 75% sequence identity, for some embodiments at least 80% identity, and for some embodiments at least 85% 86%, 87%, 88%, 89%, 90%, 91%, 92%, 93%, 94%, 95%, 96%, 97%, 98%, 99%, 99.5% sequence identity with a sequence exemplified or described herein. Hybridization and hybridization conditions as provided herein can also be used to define such plants and polynucleotide sequences of the subject disclosure. The sequence which comprises the flanking sequences plus the full insert sequence can be confirmed with reference to the deposited seed.

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, for example, to a strand of isolated DNA from corn event DP-202216-6 whether from a corn plant or from a sample that includes DNA from the event. Probes may include not only deoxyribonucleic or ribonucleic acids but also polyamides and other probe materials that bind specifically to a target DNA sequence and can be used to detect the presence of that target DNA sequence. An exemplary probe to detect the event DP-202216-6 comprises SEQ ID NO: 17. In addition, any labeled probe that binds to or exhibits high-stringency complementarity to one or more of the junction sequences, e.g., 5' and/or 3' junctions of the insert DNA adjacent to the genomic DNA of maize event DP-202216-6 comprising a sequence that is at least 99% identical to SEQ ID NOS: 7-14, 31, and 32 are suitable for use as probes.

"Primers" are isolated nucleic acids that anneal to a complementary target DNA strand by nucleic acid hybridization to form a hybrid between the primer and the target DNA strand, then extended along the target DNA strand by a polymerase, e.g., a DNA polymerase. Primer pairs refer to their use for amplification of a target nucleic acid sequence, e.g., by PCR or other conventional nucleic-acid amplification methods. "PCR" or "polymerase chain reaction" is a technique used for the amplification of specific DNA segments (see, U.S. Pat. Nos. 4,683,195 and 4,800,159; herein incorporated by reference).

Probes and primers are of sufficient nucleotide length to bind to the target DNA sequence specifically in the hybridization conditions or reaction conditions determined by the operator. This length may be of any length that is of sufficient length to be useful in a detection method of choice. Generally, 11 nucleotides or more in length, 18 nucleotides or more, and 22 nucleotides or more, are used. Such probes and primers hybridize specifically to a target sequence under high stringency hybridization conditions. Probes and primers according to embodiments may have complete DNA sequence similarity of contiguous nucleotides with the target sequence, although probes differing from the target DNA sequence and that retain the ability to hybridize to target DNA sequences may be designed by conventional methods. Probes can be used as primers, but are generally designed to bind to the target DNA or RNA and are not used in an amplification process.

Specific primers may be used to amplify an integration fragment to produce an amplicon that can be used as a "specific probe" for identifying event DP-202216-6 in biological samples. When the probe is hybridized with the nucleic acids of a biological sample under conditions which allow for the binding of the probe to the sample, this binding can be detected and thus allow for an indication of the presence of event DP-202216-6 in the biological sample. Such identification of a bound probe has been described in the art. In an embodiment of the disclosure, the specific probe is a sequence which, under optimized conditions, hybridizes specifically to a region within the 5' or 3' flanking region of the event and also comprises a part of the foreign DNA contiguous therewith. The specific probe may comprise a sequence of at least 80%, between 80 and 85%, between 85 and 90%, between 90 and 95%, and between 95 and 100% identical (or complementary) to a specific region of the event.

Probes and primers (and amplicons) are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 polynucleotides or more in length. Such probes and primers hybridize specifically to a target sequence under high stringency hybridization conditions. In some embodiments, probes and primers have complete sequence similarity with the target sequence, although probes differing from the target sequence and that retain the ability to hybridize to target sequences may be designed by conventional methods.

Methods for preparing and using probes and primers are described, for example, in Sambrook et al., *Molecular Cloning: A Laboratory Manual*, 2$^{nd}$ ed., vol. 1-3, Cold Spring Harbor Laboratory Press, Cold Spring Harbor, N.Y. 1989 (hereinafter, "Sambrook et al., 1989"); Ausubel et al. eds., *Current Protocols in Molecular Biology*, Greene Publishing and Wiley-Interscience, New York, 1995 (with periodic updates) (hereinafter, "Ausubel et al., 1995"); and Innis et al., *PCR Protocols: A Guide to Methods and Applications*, Academic Press: San Diego, 1990. PCR primer pairs can be derived from a known sequence, for example, by using computer programs intended for that purpose such as the PCR primer analysis tool in Vector NTI version 6 (Informax Inc., Bethesda Md.); PrimerSelect (DNASTAR Inc., Madison, Wis.); and Primer (Version 0.5©, 1991, Whitehead Institute for Biomedical Research, Cambridge, Mass.). Additionally, the sequence can be visually scanned and primers manually identified using guidelines known to one of skill in the art.

A "kit" as used herein refers to a set of reagents for the purpose of performing the method embodiments of the disclosure, more particularly, the identification of event DP-202216-6 in biological samples. A kit of may be used, and its components can be specifically adjusted, for purposes of quality control (e.g. purity of seed lots), detection of event DP-202216-6 in plant material, or material comprising or derived from plant material, such as but not limited to food or feed products. "Plant material" as used herein refers to material which is obtained or derived from a plant.

Primers and probes based on the flanking DNA and insert sequences disclosed herein can be used to confirm (and, if necessary, to correct) the disclosed sequences by conventional methods, e.g., by re-cloning and sequencing such sequences. The nucleic acid probes and primers hybridize under stringent conditions to a target DNA sequence. Any conventional nucleic acid hybridization or amplification method may be used to identify the presence of DNA from a transgenic event in a sample. Nucleic acid molecules or fragments thereof are capable of specifically hybridizing to other nucleic acid molecules under certain circumstances.

A nucleic acid molecule is said to be the "complement" of another nucleic acid molecule if they exhibit complete complementarity or minimal complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, a Practical Approach*, IRL Press, Washington, D.C. (1985), departures from complete complementarity are therefore permissible, as long as such departures do not completely preclude the capacity of the molecules to form a double-stranded structure. In order for a nucleic acid molecule to serve as a primer or probe it needs to be sufficiently complementary in sequence to be able to form a stable double-stranded structure under the particular solvent and salt concentrations employed.

In hybridization reactions, specificity is typically the function of post-hybridization washes, the relevant factors being the ionic strength and temperature of the final wash solution. The thermal melting point ($T_m$) is the temperature (under defined ionic strength and pH) at which 50% of a complementary target sequence hybridizes to a perfectly matched probe. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)-0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$.

Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) and Sambrook et al. (1989).

The principle of hybridization analysis is that a single-stranded DNA or RNA molecule of a known sequence (e.g., the probe) can base-pair to a second DNA or RNA molecule that contains a complementary sequence (the target), with the stability of the hybridization depending on the extent of base pairing that occurs under the conditions tested. Appropriate stringency conditions for DNA hybridization, include for example, 6× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. or up to 0.1×SSC or 0.2×SSC, at 55° C. or 65° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable (e.g., time) is changed. In one embodiment, a nucleic acid of the present disclosure will specifically hybridize to one or more of the nucleic acid molecules set forth in SEQ ID NOS: 6-14, or complements or fragments thereof under high stringency conditions. The hybridization of the probe to the target DNA molecule can be detected by methods known to those skilled in the art. These can include, but are not limited to, fluorescent tags, radioactive tags, antibody based tags, and chemiluminescent tags.

In some embodiments, a complementary sequence has the same length as the nucleic acid molecule to which it hybridizes. In some embodiments, the complementary sequence is 1, 2, 3, 4, 5, 6, 7, 8, 9, or 10 nucleotides longer or shorter than the nucleic acid molecule to which it hybridizes. In some embodiments, the complementary sequence is 1%, 2%, 3%, 4%, or 5% longer or shorter than the nucleic acid molecule to which it hybridizes. In some embodiments, a complementary sequence is complementary on a nucleotide-for-nucleotide basis, meaning that there are no mismatched nucleotides (each A pairs with a T and each G pairs with a C). In some embodiments, a complementary sequence comprises 1, 2, 3, 4, 5, 6, 7, 8, 9, 10 or less mismatches. In some embodiments, the complementary sequence comprises 1%, 2%, 3%, 4%, 5%, 6%, 7%, 8%, 9%, or 10% or less mismatches.

"Percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways that are within the skill in the art, for instance, using publicly available computer software such as BLAST, BLAST-2. Those skilled in the art can determine appropriate parameters for aligning sequences, including any algorithms needed to achieve maximal alignment over the full length of the sequences being compared. The percent identity between the two sequences is a function of the number of identical positions shared by the sequences (e.g., percent identity of query sequence=number of identical positions between query and subject sequences/total number of positions of query sequence×100). For example, Clustal W method of aligning multiple sequences is described in Thompson J, Higgins D and Gibson T (1994). Clustal W: improving the sensitivity of progressive multiple sequence alignment through sequence weighting." Nucleic Acids Research, Vol 22: pp. 4673-80. Another method is Clustal V, described in Higgins D G and Sharp P M (1989). "Fast and sensitive multiple sequence alignments on a microcomputer." CABIOS, Vol. 5, No. 2: pp. 151-153.

Regarding the amplification of a target nucleic acid sequence (e.g., by PCR) using a particular amplification primer pair, stringent conditions permit the primer pair to hybridize only to the target nucleic-acid sequence to which a primer having the corresponding wild-type sequence (or its complement) would bind to produce a unique amplification product, the amplicon, in a DNA thermal amplification reaction.

As used herein, "amplified DNA" or "amplicon" refers to nucleic acid generated as a result of the amplification of a target nucleic acid sequence that is part of a nucleic acid template. For example, in an embodiment, such amplified DNA or amplicons may contain a nucleic acid sequence that is specific to the Events disclosed herein, for example, DP-202216-6. DNA extracted from a plant tissue sample may be subjected to a nucleic acid amplification method using a DNA primer pair that includes a first primer derived from flanking sequence adjacent to the insertion site of inserted heterologous DNA, and a second primer derived from the inserted heterologous DNA to produce an amplicon that is diagnostic for the presence of the event DNA, e.g., DP-202216-6. Alternatively, the second primer may be derived from the flanking genomic sequence. The amplicon may be of any suitable length and has a nucleic acid sequence that is also diagnostic for the Event. Alternatively, primer pairs can be derived from flanking sequence on both sides of the inserted DNA so as to produce an amplicon that includes the entire insert nucleotide sequence as well as the sequence flanking the insert. A primer or a pair of primers derived from the flanking genomic sequence may be located at a distance from the inserted DNA sequence, this distance can range from one nucleotide base pair up to the limits of the amplification reaction, for example 10,000 or about 20,000 bp.

Nucleic acid amplification can be accomplished by any of the various nucleic acid amplification methods known in the art, including PCR. A variety of amplification methods are known in the art and are described, inter alia, in U.S. Pat. Nos. 4,683,195 and 4,683,202 and in Innis et al., (1990) supra. PCR amplification methods have been developed to amplify up to 22 Kb of genomic DNA and up to 42 Kb of bacteriophage DNA (Cheng et al., *Proc. Natl. Acad. Sci. USA* 91:5695-5699, 1994). These methods as well as other methods known in the art of DNA amplification may be used in the practice of the embodiments of the present disclosure. It is understood that a number of parameters in a specific PCR protocol may need to be adjusted to specific laboratory conditions and may be slightly modified and yet allow for the collection of similar results. These adjustments will be apparent to a person skilled in the art.

The amplicon produced by these methods may be detected by a plurality of techniques, including, but not limited to, Genetic Bit Analysis (Nikiforov, et al. *Nucleic Acid Res.* 22:4167-4175, 1994) where a DNA oligonucleotide is designed which overlaps both the adjacent flanking DNA sequence and the inserted DNA sequence. The oligonucleotide is immobilized in wells of a microwell plate. Following PCR of the region of interest (using one primer in the inserted sequence and one in the adjacent flanking sequence) a single-stranded PCR product can be hybridized to the immobilized oligonucleotide and serve as a template for a single base extension reaction using a DNA polymerase and labeled ddNTPs specific for the expected next base. Readout may be fluorescent or ELISA-based. A signal indicates presence of the insert/flanking sequence due to successful amplification, hybridization, and single base extension.

Another detection method is the pyrosequencing technique as described by Winge (2000) *Innov. Pharma. Tech.* 00:18-24. In this method an oligonucleotide is designed that overlaps the adjacent DNA and insert DNA junction. The oligonucleotide is hybridized to a single-stranded PCR product from the region of interest (one primer in the inserted sequence and one in the flanking sequence) and incubated in the presence of a DNA polymerase, ATP, sulfurylase, luciferase, apyrase, adenosine 5' phosphosulfate and luciferin. dNTPs are added individually and the incorporation results in a light signal which is measured. A light signal indicates the presence of the transgene insert/flanking sequence due to successful amplification, hybridization, and single or multi-base extension.

Fluorescence polarization as described by Chen et al., (1999) *Genome Res.* 9:492-498 is also a method that can be used to detect an amplicon. Using this method an oligonucleotide is designed which overlaps the flanking and inserted DNA junction. The oligonucleotide is hybridized to a single-stranded PCR product from the region of interest (one primer in the inserted DNA and one in the flanking DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

TaqMan® (PE Applied Biosystems, Foster City, Calif.) is a quantitative amplification reaction (qPCR) for detecting and quantifying the presence of a DNA sequence and is commercially available. Briefly, TaqMan probes are designed such that they anneal within a DNA region amplified by a specific set of primers and include a fluorophore (FRET) oligonucleotide probe that overlaps the flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence and/or the amount of the flanking/transgene insert sequence due to successful amplification and hybridization.

Molecular beacons have been described for use in sequence detection as described in Tyangi et al. (1996) *Nature Biotech.* 14:303-308. Briefly, a FRET oligonucleotide probe is designed that overlaps the flanking and insert DNA junction. The unique structure of the FRET probe results in it containing secondary structure that keeps the fluorescent and quenching moieties in close proximity. The FRET probe and PCR primers (one primer in the insert DNA sequence and one in the flanking sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

The term "allele" refers to an alternative form of a gene, whereby two genes can differ in DNA sequences. Such differences may result from at least one mutation (e.g., deletion, insertion, and/or substitution) in the nucleic acid sequence. Alleles may result in modified mRNAs or polypeptides whose structure or function may or may not be modified. Any given gene may have none, one, or many allelic forms. Each of these types of changes may occur alone, or in combination with the others, one or more times in a given sequence.

A hybridization reaction using a probe specific to a sequence found within the amplicon is yet another method used to detect the amplicon produced by a PCR reaction. The term "zygosity" generally refers to the similarity of alleles for a gene or trait in an organism (e.g., a plant). If both alleles are the same, the organism is homozygous for the allele. If the two alleles are different, the organism is heterozygous for the gene or trait. If one allele is not present, the organism is hemizygous. If both alleles are not present, the organism is nullizygous. For example, a plant is homozygous for the trait of interest if the insert DNA along with the junction sequence is present at the same location on each chromosome of a chromosome pair (both the alleles). For example, a maize plant having Event DP-202216-6 at the same location on both the copies of the chromosome. Similarly, a plant is considered heterozygous if the transgene insert along with the junction sequence (e.g., Event DP-202216-6) is present on only one of the chromosomes of a chromosome pair (only one allele). A wild-type plant is considered "null" when compared to the transgenic Event DNA.

The term "label" when used herein refers to a detectable compound or composition that is conjugated directly or indirectly to a probe to generate a "labeled" probe. The label may be detectable by itself (e.g. radioisotope labels or fluorescent labels) or, in the case of an enzymatic label, may catalyze chemical alteration of a substrate compound or composition that is detectable (e.g., avidin-biotin).

As used herein, a "line" is a group of plants that display little or no genetic variation between individuals for at least one trait. Such lines may be created by several generations of self-pollination and selection, or vegetative propagation from a single parent using tissue or cell culture techniques.

As used herein, the terms "cultivar" and "variety" are synonymous and refer to a line which is used for commercial production. "Stability" or "stable" means that with respect to the given component, the component is maintained from generation to generation and, for some embodiments, at least three generations at substantially the same level, e.g., for some embodiments±15%, for some embodiments±10%, most for some embodiments±5%. The stability may be affected by temperature, location, stress and the time of planting.

"Agronomically elite" means that a line has desirable agronomic characteristics such as maturity, disease resistance, standability, ear height, plant height, and the like, in addition to yield increase due to the subject event(s).

In some embodiments the DP-202216-6 maize event may further comprise a stack of additional traits. Plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene and co-transformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). Additional traits can include for example, drought tolerance and other abiotic stress tolerance traits. Such traits can be introduced by breeding with maize plants containing other recombinant events or with maize plants containing native variations or genome edited variations.

In some embodiments, DP-202216-6 maize event can be stacked with one or more additional input traits (e.g., herbicide resistance, fungal resistance, virus resistance, stress tolerance, disease resistance, male sterility, stalk strength, and the like) or output traits (e.g., increased yield, modified starches, improved oil profile, balanced amino acids, high lysine or methionine, increased digestibility, improved fiber quality, drought resistance, and the like). In a further embodiment, the DP-202216-6 maize event may be combined with one or more additional Bt insecticidal toxins or other non-Bt insecticidal proteins.

In some embodiments, corn plants containing DP-202216-6 event can be crossed with corn plants containing other corn Events or combination thereof and the resulting properties of the progeny plants are evaluated. For example, corn plants containing DP-202216-6 Event can be crossed or combined with corn plants including one or more combinations, of the following: MON810; DAS-59122-7; MIR604; MON89034; MON863; MON87411; MON87403; MON87427; MON-00603-6 (NK603); MON-87460-4; MON-88017-3; LY038; TC1507; 5307; DAS-06275-8; BT176; BT11; MIR162; GA21; MZDT09Y; SYN-05307-1; DP-004114-3; and DAS-40278-9.

The following examples are offered by way of illustration and not by way of limitation. As described herein, Event DP-202216-6 is also referred to as "Event 16", "E16" "event 16" or "Event 16-6" and they all refer to the same maize event DP-202216-6. The protein encoded by the Maize MADS box ZmM28 gene in the plasmid PHP40099 or the Event DP-202216-6 is also referred to as AG099 protein and the corresponding DNA sequence as AG099 gene or AG099 DNA.

EXAMPLES

Example 1

Performance of Plants with AG099 Across Yield Levels, Treatments, Hybrids and Population Densities A series of grain yield trials were conducted from Years 1 through 4 in elite corn hybrids across multiple testing locations in order to assess the yield in elite maize hybrids having AG099 events. In total, about eighty-six locations containing approximately thirty unique hybrids with maturities ranging from 105-112 days were used to evaluate the performance of AG099 events relative to a wild type control. Testing sites were established across locations such as Iowa, Illinois, Missouri, Nebraska, Indiana, Kansas, Texas, California, Wisconsin, South Dakota and Minnesota. Locations were managed to achieve various yield levels ranging from highly drought stressed 70 bu/acre to optimal growing conditions 250 bu/acre. Soil types consisted of a variety of high sand, sandy loam, silty loam, loam and some clay.

In all locations, entries containing the AG099 construct (Events 18 and Events 16) were compared directly to the wild type for each specific hybrid background (Table 2). Two to four replicates of a split plot design were established at each location, with hybrid the main plot and entry as the sub plot (WT, Event 18, Event 16).

A mixed model analysis of variance was conducted using ASREML where BLUEs (Best Linear Unbiased Estimates) were generated for each event and wild type across all hybrids within a given location. Pairwise contrasts of these event BLUEs to wild type BLUEs were conducted to test significant differences.

TABLE 2

Comparison of two AG099 Events in multiple hybrid background to Wild-Type control averaged across multiple locations in Year 4 of the multi-year trial.
Grain Yield (% increase over control)

| Hybrid | EVT16 | P-Value | EVT18 | P-Value |
|---|---|---|---|---|
| Hybrid1 | 1.6 | 0.06 | 1.8 | 0.09 |
| Hybrid2 | 0.7 | 0.30 | 0.9 | 0.38 |
| Hybrid3 | −1.3 | 0.01 | 1.2 | 0.29 |
| Hybrid4 | −0.6 | 0.00 | 0.2 | 0.83 |
| Hybrid5 | 1.6 | 0.00 | 1.7 | 0.08 |
| Hybrid6 | 2.0 | 0.12 | 0.6 | 0.59 |
| Hybrid7 | 2.9 | 0.10 | 2.9 | 0.01 |
| Hybrid8 | 3.3 | 0.22 | 3.5 | 0.00 |
| Hybrid9 | 3.6 | 0.55 | 0.6 | 0.55 |
| Hybrid10 | 1.2 | 0.52 | 0.2 | 0.07 |

Across all testing locations and hybrids, Event 16 and Event 18 demonstrated an average increase of 4.1 bu/acre and 3.5 bu/acre respectively. Moreover, when averaged across all hybrids in an environment, Event 16 improved yield over the wild type control in 83% of those environments (~5.7 bu/ac) and Event 18 improved yield in 78% of the environments.

Thus, increased expression of a gene encoding AG099 (SEQ ID NO: 1), as exemplified by Event 16, results in plants with increased grain yield in multiple corn hybrid backgrounds, in multiple locations, multiple testing environments, and repeated across several years of testing.

TABLE 3

Yield increase in comparison to control and % wins across various yield environments for AG099 events

|  | <120 bu 17 M Acre | 120-160 bu 24 M Acre | 160-200 bu 29 M Acre | >200 bu 22 M Acre |
|---|---|---|---|---|
| AG099 (EVT 16) % Wins | 91 | 91 | 88 | 77 |
| AG099 (EVT 16) Bu/acre increase | 5 | 5.3 | 5 | 3 |
| AG099 (EVT 18) % Wins | 100 | 91 | 80 | 70 |
| AG099 (EVT 18) Bu/acre increase | 4.9 | 7 | 4.1 | 1.8 |

Several yield trial testing sites were established in Iowa, Illinois, Missouri, Nebraska, Indiana, Wisconsin, and Minnesota in order to evaluate AG099 events in high yielding areas indicative of the mid-western US corn belt. In these locations, yields of over 160 bu/acre were established and often were greater than 180 bu/acre which represents a large portion of the most productive corn growing regions in the United States. In order to evaluate the response of AG099 to drought stress, additional sites in Kansas, Texas and California were established with the capability of specifically managing the amount of water applied to the test plots during the growing season. Managed stress conditions ranged from severe stress of less than 120 bu/acre up to a very mild stress just below 160 bu/acre The results shown in Table 3 demonstrate that Event 16 had 91% wins and demonstrated 5 bu/ac increase over the wild-type in the less than 120 bu/ac zone. In the 120-160 bu/ac zone, Event 16 had 91% wins and about 5.3 bu/ac yield increase over the wild-type control. In the moderately higher yielding zone (160-200 bu/ac), Event 16 showed substantially higher % wins (88%) when compared to Event 18 and 5 bu/ac increase over the wild-type control. In the highest yielding zone that was tested—more than 200 bu/ac zone, Event 16 yielded about 3 bu/ac more than the wild-type control and had 77% wins across locations.

To test AG099 containing events and resulting yield increase under different planting populations, an experiment was conducted in year 4 at six unique locations (Table 4). Experimental treatments consisted of planting populations of 36,000, 40,000, 44,000, and 48,000 plants per acre. Within each population, corn Event DP-202216-6 and the wild type control were evaluated across 12 different hybrid backgrounds. The yield of corn Event DP-202216-6 within and across densities was measured by calculating the difference in yield (BLUEs) of Event 16 to that of the wild type.

TABLE 4

Yield level of corn Event DP-202216-6 (E16) at various population densities.

| N | Population | E16 | Control | Difference | P-Value |
|---|---|---|---|---|---|
| 88 | 36,000 PPA | 226.3 | 223.4 | 2.9 | 0.31 |
| 94 | 40,000 PPA | 232.4 | 229.9 | 2.5 | 0.37 |
| 83 | 44,000 PPA | 232.0 | 228.5 | 3.5 | 0.21 |
| 89 | 48,000 PPA | 233.3 | 228.3 | 5.0 | 0.08 |

N = total comparisons = site number × hybrid background × replication number.

Across all hybrids, Event DP-202216-6 resulted in grain yield increases over the Wild Type in all tested planting populations. Yield increase over the wild type control was about 5.0 bu/acre at the highest tested plant population of 48,000 plants per acre. This represented a 2.1 bu/acre greater increase than was achieved at the tested lower population of 36,000 plants per acre.

Example 2

Secondary Trait Characteristics of Maize Plants Containing Event DP-202216-6

Secondary agronomic trait data was taken for both events (Events 16 and 18) in the field across a four-year period. Statistically significant increases for plant and ear height were observed in both events when averaged across all years and hybrids evaluated. Both events increased plant height by 0.7 inches. Event 16 and event 18 had exhibited increased ear height over the wild type control 2.0 and 1.4 inches respectively. No significant differences were observed for event 16 in either early or late root lodging, however event 18 plants displayed increased early root lodging by 4.8% over the control. Brittle snap was greater than the wild type control for event 18, while event 16 showed no statistically significant difference for brittle snap. No difference in test weight was observed for event 16, however event 18 had reduced test weight by 0.5 lb/bu when compared to the control. Both events had slightly increased grain moisture compared to the wild type control by 0.2% and 0.3% for events 16 and 18 respectively. *Fusarium* ear mold was significantly reduced relative to the wild type control by 1 and 0.6 scores on a one to ten score for events 16 and 18 respectively. The results are shown in Table 5 below.

TABLE 5

Secondary trait comparison in maize hybrids for Event 16 and 18 in comparison to the control.

| Trait Characteristic | EVENT 16 (DP-202216-6) | EVENT 18 |
|---|---|---|
| Plant Height | +0.7 in* | +0.7 in* |
| Ear Height | +2.0 in* | +1.4 in* |
| BOREAS Early Root Lodging | −0.1%$^{NS}$ | +4.8%* |
| BOREAS Late Root Lodging | −1.4%$^{NS}$ | −0.0%$^{NS}$ |
| Brittle Snap (Natural) | 0.0$^{NS}$ | +0.2* |
| BOREAS Brittle | +1.4%$^{NS}$ | +0.6%$^{NS}$ |
| Test Weight | 0.0 lbs/bu$^{NS}$ | −0.5 lbs/bu* |
| Grain Moisture | +0.2%* | +0.3%* |
| Fusers | −1 Score Less Disease* | −0.6 Score Less Disease* |

*represents statistical significance at p < 0.05. Significant increases for plant and ear height were observed in both events when averaged across all years and hybrids evaluated. Both events increased plant height by 0.7 inches. Event 16 and Event 18 had significantly increased ear height over the wild type control 2.0 and 1.4 inches respectively. No significant differences were observed for Event 16 in either early or late root lodging, however Event 18 significantly increased early root lodging by 4.8% over the control. Brittle snap was significantly greater than the wild type control for event 18, while Event 16 showed no differences for brittle snap. No difference in test weight was observed for Event 16 when compared to the wild-type control, however event 18 reduced test weight by 0.5 lbs per bushel when compared to the control. Both events slightly increased grain moisture over the wild type control by 0.2% and 0.3% for events 16 and 18 respectively. Finally, *fusarium* ear mold was significantly reduced relative to the wild type control by 1 and 0.6 scores on a one to ten score for Events 16 and 18 respectively.

Growing degree units to silk (GDUSLK): Measurement records the total accumulated growing degree units when 50% of the plants in the plot have fully emerged silks. A single day equivalent is approximately 2.5 growing degrees units (GDU) for this data set.

Growing degree units to shed (GDUSHD): Measurement records the total accumulated growing degree units when 50% of the plants in the plot have tassels that are shedding pollen. A single day equivalent is approximately 2.5 growing degrees units for this data set.

Ear height (EARHT): Measurement from the ground to the attachment point of the highest developed ear on the plant. Ear height is measured in inches.

Plant height (PLTHT): Measurement from the ground to the base of the flag leaf. Plant height is measured in inches.

Moisture (MST): Measurement of the percent grain moisture at harvest.

Yield: Recorded weight of grain harvested from each plot. Calculations of reported bu/acre yields were made by adjusting to measured moisture of each plot.

Inbred trials were planted at eight locations with two replicates of the entry list at each location. Both replicates were planted as nested designs where both events of AG099 and the Wild Type were nested together based on inbred background. Agronomic data and observations were collected for the inbred trials and analyzed for comparison to a wild type entry (WT), or without the AG099 trait version of the same genotype. On average and across different inbreds, the presence of AG099 gene as part of the Event DP-202216-6 did not show any significant agronomic characteristics as part of the inbred evaluations.

To evaluate the hybrid data, a mixed model framework was used to perform multi location analysis. In the multi-location analysis, main effect construct design is considered as fixed effect. Factors for location, background, tester, event, background by construct design, tester by construct design, tester by event, location by background, location by construct design, location by tester, location by background by construct design, location by tester by construct design, location by event, location by tester by event are considered as random effects. The spatial effects including range and plot within locations were considered as random effects to remove the extraneous spatial noise. The heterogeneous residual was assumed with autoregressive correlation as AR1*AR1 for each location. The estimate of construct design and prediction of event for each background were generated. The T-tests were conducted to compare construct design/event with WT. A difference was considered statistically significant if the P-value of the difference was less than 0.05. Yield analysis was by ASREML (VSN International Ltd; Best Linear Unbiased Prediction; Cullis, B. R et al (1998) *Biometrics* 54: 1-18, Gilmour, A. R. et al (2009); ASReml User Guide 3.0, Gilmour, A. R., et al (1995) *Biometrics* 51: 1440-50).

To evaluate the inbred data, a mixed model framework was used to perform multi location analysis. In the multi-location analysis, main effect construct design is considered as fixed effect. Factors for location, background, event, background by construct design, location by background, location by construct design, location by background by construct design, location by event and rep within location are considered as random effects. The spatial effects including range and plot within locations were considered as random effects to remove the extraneous spatial noise. The heterogeneous residual was assumed with autoregressive correlation as AR1*AR1 for each location. The estimate of construct design and prediction of event for each background were generated. The T-tests were conducted to compare construct design/event with WT. A difference was considered statistically significant if the P-value of the difference was less than 0.05. Yield analysis was by ASREML (VSN International Ltd; Best Linear Unbiased Prediction; Cullis, B. R et al (1998) *Biometrics* 54: 1-18, Gilmour, A. R. et al (2009); ASReml User Guide 3.0, Gilmour, A. R., et al (1995) *Biometrics* 51: 1440-50).

Example 3

Maize Field Grain Yield Increase

Maize transgenic plants expressing a recombinant maize polynucleotide sequence encoding the polypeptide (SEQ ID NO: 1) were field tested. The transgenic maize plants demonstrated efficacy for increased yield and yield stability. Transformed maize plants containing the recombinant polynucleotide encoding SEQ ID NO: 1 were then converted into elite inbreds and top-crossed for a series of grain yield trials for three years. Several hybrid platforms were evaluated in multiple unique environments that included various levels of drought and nitrogen stress and well as environments targeted for optimal yield levels, where yield levels ranged from 80 bu/acre to 250 bu/acre. An average planting density of about 30,000 to about 36,000 plants/acre was used for these field trials. A majority of the trial plots had a planting density of about 34,000 to about 35,000 plants per acre. Transgene efficacy was demonstrated by contrasts to an isogenic wild type control in all trials. Efficacy for yield and yield stability were demonstrated over the control in all environmental classification breakouts as well as the overall difference from the control across the three years of testing (below). In this Example, the recombinant polynucleotide encoding SEQ ID NO: 1 was expressed under a moderately constitutive promoter, e.g. Maize GOS2 promoter sequence. Maize transgenic plants containing the recombinant polynucleotide encoding SEQ ID NO: 1 demonstrated about 3.4 bu/acre increase over control maize plants not containing the recombinant AG099 gene, based on multi-year, multi-hybrid, multi-location field trials at P<0.05. A mixed model analysis of variance was conducted using ASREML.

To evaluate the effect of ZmGos2 operably linked to a polynucleotide encoding SEQ ID NO: 1 on grain yield, field trials were conducted in wide-ranging environments for four years. Across the four-year period, a total of 40 unique hybrid backgrounds were evaluated in combination with DP-202216-6 and DP382118 events. For each hybrid background, an inbred conversion that was homozygous for the respective event was top-crossed to a select tester to generate F1 seed. For the same hybrid background, the recurrent parent of the conversion was top-crossed to the same tester to generate F1 seed of a control. All subsequent comparisons were made between the heterozygous F1 transgenic hybrid with the control of that same hybrid background.

During the four-year period, experimental entries were evaluated across a range of environments at testing sites located in in Woodland, Calif.; Plainview, Tex.; Garden City, Kans.; York, Nebr.; Union City, Tenn.; Johnston, Iowa; Adel, Iowa; Marion, Iowa; Readlyn, Iowa; Reasnor, Iowa; Miami, Mo.; Sikeston, Mo.; Sciota, Ill.; San Jose, Ill.; Buda, Ill.; Princeton, Ill.; Humboldt, Ill.; Seymour, Ill.; Windfall, Ind.; Volga, S. Dak.; Janesville, Wis.; Mankato, Minn., and Viluco and Buin, Chile. All testing sites were established and managed with the goal of achieving optimal yield levels. Fifty-six unique testing sites provided data of sufficient quality across the four-year period. Average yield levels ranged from 10,900 kg ha-1 to 19,570 kg ha-1 across those testing sites.

Experimental designs were split plots with hybrid background as the main plot and event or the control as the sub plot. Two to three replicates were established at each testing site with main plots randomized within replication and sub plots randomized within main plot. Experimental entries were grown in four-row plots that ranged from 4.4 m to 5.3 m in length with a 0.5 m alley in between. Whole testing sites and individual plots of poor quality were removed from data collection procedures and analysis per a standardized procedure. Grain weights and moistures for each experimental entry were measured by harvesting the center two rows of the four-row plot using a small-plot research combine. Yield was standardized within the experiment by adjusting the harvested grain weight of each plot to fifteen percent moisture. A mixed model analysis of variance was conducted using ASREML accounting for random field and spatial components as well as the fixed components of event or control. BLUEs (Best Linear Unbiased Estimates) were generated for each event and control across all hybrid backgrounds for each location. Pairwise contrasts of the event BLUEs to control BLUEs were conducted to test for significant differences (BLUE DIFFs) at P<0.05 for both DP-202216-6 and Event 18.

These results demonstrate that expression of the recombinant polynucleotide encoding SEQ ID NO: 1 increases grain yield of maize under field conditions.

Example 4

AG099 Gene, Construct Design for Generating Event DP-202216-6

Maize (*Zea mays* L.) was transformed by *Agrobacterium*-mediated transformation with a plant transformation vector/plasmid. The T-DNA region of this plasmid is represented schematically in FIG. 1 and the sequence is represented by SEQ ID NO: 5 and the insert is represented by SEQ ID NO: 6. A summary of the genetic elements and their positions on the T DNA is described in Tables 6-7.

The T-DNA of transformed construct contains two gene cassettes. The first cassette (AG099 gene cassette) contains the AG099 encoding the AG099 protein. The 251 residue protein produced by expression of the AG099 sequence has an approximate molecular weight of 28 kDa. The expression of the AG099 gene is controlled by the promoter from the *Zea mays* translation initiation factor gos2 (zm-gos2) gene along with the intron 1 region from the maize ubiquitin 1 (ubiZM1) gene. Transcription of the AG099 gene cassette is terminated by the presence of the terminator sequence from the proteinase inhibitor II (pinII) gene of *Solanum tuberosum*.

The second gene cassette (mo-pat gene cassette) contains a phosphinothricin acetyl transferase gene (mo-pat) from *Streptomyces viridochromogenes*. The mo-pat gene expresses the phosphinothricin acetyl transferase (PAT) enzyme that confers tolerance to phosphinothricin. The PAT protein is 183 amino acids in length and has an approximate molecular weight of 21 kDa. Expression of the mo-pat gene is controlled by the ubiZM1 promoter, the 5' UTR and intron, in conjunction with a second copy of the pinII terminator.

TABLE 6

Description of Genetic Elements in the T-DNA Region of Plasmid PHP40099 for AG099 gene cassette

| Location on T-DNA (Base Pair Position) | Genetic Element | Size (bp) | Description |
|---|---|---|---|
| 1-25 | Right Border (RB) | 25 | T-DNA Right Border region from the *Agrobacterium tumefaciens* Ti plasmid |
| 758-1,614 | zm-gos2 Promoter | 857 | Promoter region from the *Zea mays* translation initiation factor gos2 gene |

TABLE 6-continued

Description of Genetic Elements in the T-DNA Region of Plasmid PHP40099 for AG099 gene cassette

| Location on T-DNA (Base Pair Position) | Genetic Element | Size (bp) | Description |
|---|---|---|---|
| 1,655-2,667 | ubiZM1 Intron | 1,013 | Intron region from the *Zea mays* ubiquitin gene 1 |
| 2,749-3,605 | zmm28 | 857 | MADS-domain transcription factor gene region from *Zea mays* including 5' and 3' noncoding regions as described below: 5' noncoding region at bp 2749-2808 (60 bp long); Coding sequence at bp 2,809-3,564 (756 bp long); 3' noncoding region at bp 3565-3605 (41 bp long) |

TABLE 7

Description of Genetic Elements in the T-DNA Region of Plasmid PHP40099 for Mo-pat gene cassette (continued)

| Location on T-DNA (Base pair position) | Genetic Element | Size (bp) | Description |
|---|---|---|---|
| 3,660-3,967 | pinII Terminator[a] | 308 | Terminator region from the *Solanum tuberosum* (potato) proteinase inhibitor II gene |
| 4,145-5,044 | ubiZM1 Promoter | 900 | Promoter region from the *Zea mays* ubiquitin gene 1 |
| 5,045-5,127 | ubiZM1 5' UTR | 83 | 5' untranslated region from the *Zea mays* ubiquitin gene 1 |
| 5,128-6,140 | ubiZM1 Intron | 1,013 | Intron region from the *Zea mays* ubiquitin gene 1 |
| 6,243-6,794 | mo-pat | 552 | Maize-optimized phosphinothricin acetyltransferase gene from *Streptomyces viridochromogenes* |
| 6,803-7,112 | pinII Terminator | 311 | Terminator region from the *Solanum tuberosum* (potato) proteinase inhibitor II gene |
| 7,446-7,470 | Left Border (LB) | 25 | T-DNA Left Border region from the *Agrobacterium tumefaciens* Ti plasmid |

[a]The pinII Terminator has 3 bp less on the 5' end than the other pinII Terminator in this vector.

Example 5

Segregation of DP-202216-6 Maize Across Two Generations

Separate generations (T2 and F1*1) of DP-202216-6 maize were grown in 4-inch pots, organized in flats containing 15 pots, using typical greenhouse production conditions. Up to 165 seeds were planted for each generation. After germination, but prior to leaf sampling, maize plants were thinned to 100 healthy plants. When plants were at approximately the V3 growth stage (i.e. when the collar of the third leaf becomes visible) leaf punch samples were collected from 100 plants. Leaf samples were analyzed using real-time PCR analysis for the presence or absence of the DP-202216-6 event and the AG099 and mo-pat genes.

PCR amplification of unique regions within the introduced genetic elements can distinguish the test plants from their non-genetically modified counterparts, and can be used to screen for the presence of the inserted T-DNA region of plasmid containing AG099. For detection of the AG099 and mo-pat genes contained within the T-DNA insert as well as the genomic 5' junction spanning the DP-202216-6 maize insertion site, regions between 76-bp and 105-bp were amplified using primers and probes specific for each unique sequence. Additionally, a 79-bp amplicon of an endogenous reference gene, High Mobility Group A (hmg-A), was used in duplex with each assay for both qualitative and quantitative assessment of each assay and to demonstrate the presence of sufficient quality and quantity of DNA within the PCR reaction. Data from hmg-A was used in calculations regarding scoring. Data were compared to the performance of the validated negative genomic control. PCR results were evaluated for proper segregation. The population from the T2 generation was expected to segregate at a 3:1 ratio and the population from the F1[*1] generation was expected to segregate at a 1:1 ratio, according to Mendelian rules of inheritance. A plant with positive PCR results for the associated assay was counted as a positive plant and a plant with negative PCR results was counted as a negative plant. For each generation, the total numbers of positive and negative plants are provided in Table 8. PCR results for all generations indicate that the AG099 T-DNA was inserted into a chromosome to generate Event DP-202216-6 in the maize genome.

TABLE 8

Summary of Segregation Results in Two Generations of DP202216 Maize

| Event | Generation | Expected Segregation Ratio (Positive: Negative) | Observed Segregation[a] | | | Statistical Analysis | |
|---|---|---|---|---|---|---|---|
| | | | Positive | Negative | Total | Chi-Square[b] | P-Value |
| DP-2Ø2216-6 | T2 | 3:1 | 80 | 20 | 100 | 1.33 | 0.2482 |
| | F1*[1] | 1:1 | 54 | 46 | 100 | 0.64 | 0.4237 |

[a]Event-specific and gene-specific PCR analyses were used to confirm the presence (PCR Positive) or absence (PCR Negative) of the traits of interest.
[b]Degrees of freedom = 1. A Chi-Square value greater than 3.84 (P-value less than 0.05) would indicate a significant difference.

Example 6

Copy Number/Zygosity Determination of Event 16

Copy number PCR and next-generation sequencing (NGS) analysis were used to demonstrate that a single insertion has occurred in DP-202216-6 maize (Event 16) and that the T-DNA is stably transferred across generations and the junction sequences were determined using sequencing analysis. Copy number PCR analysis was conducted on two generations (T2 and F1*1) and an application of NGS called Southern-by-Sequencing (SbS) was conducted on the T1 generation of DP202216 maize.

Genomic DNA extractions from leaf tissues of individual plants were obtained from DP202216 maize, which was generated by transforming a maize line with the plasmid PHP40099. Eight plants from the T1 generation of DP-202216-6 maize were used for SbS analysis. In addition, genomic DNA from the control maize line (used for transformation) was obtained for SbS analysis.

Southern-by-Sequencing Analysis

SbS utilizes probe-based sequence capture, Next Generation Sequencing (NGS) techniques, and bioinformatics procedures to isolate, sequence, and identify inserted DNA within the maize genome. By compiling a large number of unique sequencing reads and comparing them to the transformation plasmid, unique junctions due to inserted DNA are identified in the bioinformatics analysis and were used to determine the number of insertions within the plant genome. Eight plants of the T1 generation of DP202216 maize were analyzed by SbS to determine the insertion copy number in each plant. Six plants contained the DP202216 DNA insertion as shown by event-specific PCR analysis; the remaining two plants were shown to be negative for the insertion by the same assay. In addition, the control maize DNA was analyzed by SbS in the same manner.

Capture probes used to select PHP40099 plasmid sequences were designed and synthesized by a commercially available process. A series of unique sequences encompassing the plasmid sequence was used to design biotinylated oligonucleotides (70-74 bp) as capture probes.

Next-generation sequencing libraries were constructed using the genomic DNA from the individual DP202216 maize plants and the control maize line. Genomic DNA was randomly sheared to approximately 400 bp length and sequencing adapters ligated to the ends. SbS was performed on the DP202216 T1 plants essentially as described by Zastrow-Hayes, et al. Southern-by-Sequencing: A Robust Screening Approach for Molecular Characterization of Genetically Modified Crops. *The Plant Genome* 8: 1-15 (2015), incorporated herein by reference to the extent the methods described in that reference are applicable to the analysis disclosed herein. Briefly, the sequencing libraries from each plant were hybridized to the capture probes through two rounds of hybridization to enrich the targeted sequences. Following NGS on a commercially available HiSeq 2500 (Illumina, San Diego, Calif., USA) platform, the sequencing reads entered the bioinformatics pipeline for trimming and quality assurance. Reads were aligned against both the maize genome and the transformation construct, and reads that contained both genomic and plasmid sequence were identified as junction reads. Alignment of the junction reads to the transformation construct showed borders of the inserted DNA relative to the expected insertion.

Southern-by-Sequencing Results

Integration and copy number of the insertion were determined in DP202216-6 maize derived from construct PHP40099. The T-DNA from PHP40099 that was transferred to maize event DP-2Ø2216-6 is provided in FIG. 1. SbS was used in to evaluate the insertion in DP-202216-6 maize. SbS utilized capture probes to the transformation plasmid to isolate genomic DNA that hybridized to the probe sequences. Captured DNA was then sequenced using a NGS procedure and analyzed using bioinformatics tools. During the analysis, sequence reads that showed partial identity to the plasmid DNA sequence while the rest of the read did not match the contiguous plasmid sequence were identified as junctions between inserted DNA and genomic DNA, or between insertions of two plasmid DNA sequences that were not contiguous in the original plasmid. Multiple sequence reads were generated of each junction and these reads were compiled into a consensus sequence for the junction. A unique junction was defined as one in which the plasmid-derived sequence and the adjacent sequence were the same, although the overall length of the multiple reads for that junction varied due to the sequencing process. The number of unique junctions was related to the number of plasmid insertions present in the genome (for example, a single T-DNA insertion was expected to have two unique junctions). Detection of additional unique junctions beyond the two expected for a single insertion (if any) indicated the presence of additional plasmid insertions. Two or more insertions may be either genetically linked or unlinked to each other. For transformed lines that contained more than a single insertion, the analysis of several plants from a single generation would provide information about the segregation status of multiple insertions, as insertions that are tightly linked would be found in the same individual plant, while unlinked insertions would segregate randomly among the population. SbS also provided sequence information about the genomic context of an insertion, which can be used to identify a chromosome location if sufficient sequence of the untransformed plant genome was available. Each of the plants that were positive for the DP202216 DNA insertion resulted in the same two unique junctions that were consistent across all six plants. The 5' junction for all plants started with bp 23 of the PHP40099 T-DNA, and the insertion ended at the 3' junction at bp 7,458 of the T-DNA (FIG. 1). Right Border and Left Border termini deletions, as reported previously, may often occur in *Agrobacterium*-mediated transformation. These locations were identical across all six plants, indicating that the DP-202216-6 DNA insertion is consistent and stable across the T1 generation of DP-202216-6 maize. The SbS results for each plant were determined, including the number of unique reads at the 5' and 3' junctions for each plant (Table 9). There were no other junctions between the PHP40099 sequences and the maize genome detected in these six plants, indicating that SbS results showed that there are no additional plasmid-derived insertions present in DP-202216-6 maize. Additionally, there were no junctions between non-contiguous regions of the PHP40099 T-DNA identified, indicating that there are no detectable rearrangements or truncations in the inserted DNA other than the Right and Left Border truncations noted above. While coverage of maize endogenous elements in their native context was detected in the two negative plants, no junctions between the PHP40099 sequences and the maize genome were detected in either the two negative (for the DP-202216-6 event) plants from the segregating population of the T1 generation or from the control line, indicating that, as expected, these plants did not contain any insertions derived from PHP40099. Furthermore, there were no junctions between maize genome sequences and the backbone sequence of PHP40099 in any of the plants analyzed, demonstrating that no plasmid backbone sequences were incorporated into DP202216 maize.

SbS analysis of the T1 generation of DP-202216-6 maize demonstrated that there is a single copy of the PHP40099 T-DNA in DP-202216-6 maize and that no additional insertions are present in its genome.

TABLE 9

SbS Analysis of DP202216 Maize Plants

| Plant ID | Generation | Presence of DP-202216-6 DNA Insertion[a] | Unique Reads at 5' Junction[b] | Unique Reads at 3' Junction[c] |
|---|---|---|---|---|
| 335728647 | T1 | + | 25 | 23 |
| 335728648 | T1 | + | 20 | 31 |
| 335728649 | T1 | − | 0 | 0 |
| 335728650 | T1 | − | 0 | 0 |
| 335728651 | T1 | + | 31 | 29 |
| 335728652 | T1 | + | 50 | 39 |
| 335728653 | T1 | + | 32 | 24 |
| 335728654 | T1 | + | 37 | 23 |

[a]The presence of the DP202216 DNA insertion is based on event-specific PCR results.
[b]Unique reads supporting the location of the 5' genomic junction of the DP202216 DNA insertion at bp 23 of the PHP40099 T-DNA. Multiple identical NGS reads are condensed into each unique read.
[c]Unique reads supporting the location of the 3' genomic junction of the DP202216 DNA insertion at bp 7,458 of the PHP40099 T-DNA. Multiple identical NGS reads are condensed into each unique read.

Example 7

Event-Specific Detection Methods, Primers and Probes

For detection of the AG099 and mo-PAT genes contained within maize event DP-202216-6 as well as the genomic junction spanning the DP-202216-6 maize insertion site, regions of about 76-bp and 105-bp were amplified using primers and Taqman® probes specific for each unique sequence. Additionally, a 79-bp region of an endogenous reference gene, High Mobility Group A (hmg-A, GenBank accession number AF171874.1), is validated to be used in duplex with each assay for both qualitative and quantitative assessment of each assay and to demonstrate the presence of sufficient quality and quantity of DNA within the PCR reaction. Data from hmg-A was used in calculations regarding scoring. Data were compared to the performance of either the validated positive or copy number calibrator as well as negative genomic controls.

The real-time PCR reaction involves the 5' nuclease activity of the heat activated DNA polymerase. Two primers and one probe annealed to the target DNA with the probe, which contained a 5' fluorescent reporter dye and a 3' quencher dye. With each PCR cycle, the reporter dye is cleaved from the annealed probe by the polymerase, emitting a fluorescent signal that intensified with each subsequent cycle. The cycle at which the emission intensity of the sample amplicon rose above the detection threshold was referred to as the $C_T$ value. When no amplification occurred, there was no $C_T$ calculated by the instrument and was assigned a $C_T$ value of 40.00.

Samples were determined to be positive or negative for a specific gene of interest using the following criteria:
Positive:
  Endogenous gene $C_T$<35
  Gene of interest (GOI) $C_T$<35
  $\Delta C_T$ (delta $C_T$) (Endogenous gene $C_T$–GOI $C_T$)>−5
Negative:
  Endogenous gene $C_T$<35
  Gene of interest (GOI) $C_T$>35
  $\Delta C_T$ (Endogenous gene $C_T$–GOI $C_T$)< and >−5

If copy number of the test samples was to be determined, copy number calibrators (samples known to contain defined copies of the gene of interest, e.g. 1 or 2 copies) were used as controls for both the endogenous gene and gene of interest. The $\Delta C_T$ was calculated for the test samples and copy number calibrators as described above. The $\Delta\Delta C_T$ (delta delta $C_T$) was then used to statistically calculate copy number ($\Delta\Delta C_T$=Copy number calibrator $\Delta C_T$–sample GOI $\Delta C_T$). The algorithm tolerances were used to apply a copy number for each test sample. A copy number of 1 was applied to the sample population producing a similar mean $\Delta C_T$ when compared to the single copy calibrators, or when 0.7-1.0 $\Delta\Delta C_T$ was generated from a 2-copy calibrator. Likewise, a copy number of 2 was applied to a sample population producing a $\Delta\Delta C_T$ ranging between 0.7-1.0 when compared to the single copy calibrators; and a copy number of 3 was applied to a sample population producing a $\Delta\Delta C_T$ of approximately 0.5 when compared to the 2-copy population. The statistical algorithm also applied probabilities of each potential copy number assignment based on the assigned $\Delta\Delta C_T$ values following the analysis. Any $\Delta\Delta C_T$ values that fell outside expected ranges would produce copy number results with lower probabilities where $\Delta\Delta C_T$ values within expected ranges would produce results with high probabilities.

DNA Extraction

Genomic DNA samples, isolated from leaf tissue of 200 plants representing the T2 and F1 generations of DP202216 maize were extracted using an alkaline buffer comprised of sodium hydroxide, ethylenediaminetetraacetic acid disodium salt dihydrate (Na2-EDTA) and Tris. Approximately 3-ng of template DNA was used per reaction, regardless of total reaction volume.

Details on Composition and Preparation of Reaction Mixes

Each assay supporting the DP202216 maize insertion site and the AG099 and mo-PAT genes contained within event DP-202216-6 was multiplexed with the hmg-A endogenous reference assay. Reaction mixes included all the relevant components to support both the gene of interest and the endogenous gene for the PCR reaction. The base master mix, Bioline SensiFast™ Probe Lo-ROX master mix (commercially available) with 30% Bovine Serum Albumin (BSA) included as an additive was used. Individual concentrations of each primer varied per reaction between 300 nM and 900 nM, dependent on the optimal concentration established during the validation of the analysis. Individual concentrations of each probe per reaction were at 80 nM. Assay controls included no template controls (NTC) which consisted of water or Tris-EDTA (TE) buffer (10 mM Tris pH 8.0, 1 mM EDTA) as well as copy number calibrator and negative controls, all of which were validated for each assay performed. Annealing temperatures and number of cycles used during the PCR analyses are provided in Table 10. The primer and probes used for the PCR analysis are provided in Tables 11 and 12. Master mix formulations for each PCR analysis are provided in Tables 13-15.

PCR Parameters

The PCR parameters used during PCR analysis are listed below:

TABLE 10

Annealing Temperatures and Cycles used During the PCR Reaction

| Step | Description | | Temperature (° C.) | Time (seconds) | Cycles |
|---|---|---|---|---|---|
| 1 | Initial Denaturation | | 95 | 120[a] | 1 |
| 2a | Amplification | Denaturation | 95 | 1 | 40[b] |
| 2b | | Anneal/Extend | 60 | 20 | |

[a]If thermal cycling was completed using a Roche LightCycler ®480, 300 seconds were run for step 1
[b]If thermal cycling was completed using a Roche LightCycler ® 480, 45 cycles for steps 2a and 2b were performed.

Primers and Probes

The primers and probe used for each assay performed are listed below:

TABLE 11

Primers and Probes for PCR Analysis of the AG099 and mo-PAT Genes and the DP202216 Maize Insertion Site

| Reagent | Sequence (5' to 3') | Length (bp) |
|---|---|---|
| DP-202216-6 forward primer | CCATCTGAGGTCTGCACTCTCAC (SEQ ID NO: 15) | 23 |
| DP-202216-6 reverse primer | CTCCGCTCATGATCAGATTGTC (SEQ ID NO: 16) | 22 |
| DP-202216-6 probe | 6'FAM-AA+CA+CA+CT+CAA+A+CAC-iBFQ[a] (SEQ ID NO: 17) | 15 |
| AG099 forward primer | GGATGCTCCGCACTGTCAA (SEQ ID NO: 18) | 19 |
| AG099 reverse primer | AAGAAAGCTGGGTCGGCG (SEQ ID NO: 19) | 18 |
| AG099 probe | 6-FAM-TC+TC+G+A+AAG+G+GTGG-IBFQ[a] (SEQ ID NO: 20) | 14 |
| mo-PAT forward primer | CATCGTGAACCACTACATCGAGAC (SEQ ID NO: 21) | 24 |
| mo-PAT reverse primer | GTCGATCCACTCCTGCGG (SEQ ID NO: 22) | 18 |
| mo-PAT probe | 6-FAM-ACCGTGAACTTCCGCACCGAGC-BHQ1 (SEQ ID NO: 23) | 22 |

DP-202216-6 assay amplicon sequence (105-bp; primer and probe binding sites are in bold and underlined
CCATCTGAGGTCTGCACTCTCACCGGTAGTACAGCACAAACAACACACTCAAACACTGA
TAGTTTAAACTGAAGGCGGGAAACGACAATCTGATCATGAGCGGAG (SEQ ID NO: 24)

AG099 assay amplicon sequence (93-bp; primer and probe binding sites are in bold and underlined
GGATGCTCCGCACTGTCAAGTAACAGGTGAGGTCTTCCCAGTGTAGTTTTGCAGCTGA**TCT
CGAAAGGGTGGGCCGCCGACCCAGCTTTCTT** (SEQ ID NO: 25)

mo-PAT assay amplicon sequence (76-bp; primer and probe binding sites arein bold and underlined
CATCGTGAACCACTACATCGAGACCTCCACCGTGAACTTCCGCACCGAGCCGCAGACCC
CGCAGGAGTGGATCGAC (SEQ ID NO: 26)

[a]Probe designed as a Locked Nucleic Acids probe, commercially available from IDT, Coralville, IA.

TABLE 12

Primers and Probes for PCR Analysis of the hmg-A Endogenous Reference Gene

| Reagent | Sequence (5' to 3') | Length (base) |
|---|---|---|
| hmg-A forward primer | TTGGACTAGAAATCTCGTGCTGA (SEQ ID NO: 27) | 23 |
| hmg-A reverse primer | GCTACATAGGGAGCCTTGTCCT (SEQ ID NO: 28) | 22 |
| hmg-A probe | VIC-GCGTTTGTGTGGATTG-MGB (SEQ ID NO: 29) | 16 | hmg-A assay amplicon sequence (79-bp; primer and probe binding sites are in bold and underlined)
TTGGACTAGAAATCTCGTGCTGATTAATTGTTTTACGCGTGCGTTTGTGTGGATT GTAGGACAAGGCTCCCTATGTAGC (SEQ ID NO: 30)

Preparation of Master Mix

The components and concentrations supporting each master mix are listed below:

TABLE 13

Master Mix supporting Multiplex Assay: DP-2Ø2216-6 and hmg-A[a]

| Component | Stock Concentration | Final Concentration | Volume/reaction (µL) |
|---|---|---|---|
| SensiFast ™ probe Lo-ROX master mix | 2x | 1x | 1.5 |
| DP-2Ø2216-6 forward primer | 200 µM | 900 nM | 0.014 |
| DP-2Ø2216-6 reverse primer | 200 µM | 900 nM | 0.014 |
| DP-2Ø2216-6 probe | 100 µM | 80 nM | 0.002 |
| hmg-A forward primer | 200 µM | 300 nM | 0.005 |
| hmg-A reverse primer | 200 µM | 300 nM | 0.005 |
| hmg-A probe | 100 µM | 80 nM | 0.002 |
| Bovine Serum Albumin | 30% | 0.08%[b] | 0.009 |
| HPLC Molecular Biology Grade Water | N_A[c] | N_A[c] | 0.950 |

[a]The final volume of each reaction was 3 µL comprised of 2.5 µL of Master Mix and 0.5 µL of genomic DNA template.
[b]The concentration of Bovine Serum Albumin solution in the reaction, as a reagent, was 0.3%; the concentration based on the stock was 0.08%.
[c]N_A is equivalent to Not Applicable.

TABLE 14

Master Mix supporting Multiplex Assay: AG099 and hmg-A[a]

| Component | Stock Concentration | Final Concentration | Volume/reaction (µL) |
|---|---|---|---|
| SensiFast ™ probe Lo-ROX master mix | 2x | 1x | 1.5 |
| AG099 forward primer | 200 µM | 600 nM | 0.009 |
| AG099 reverse primer | 200 µM | 600 nM | 0.009 |
| AG099 probe | 100 µM | 80 nM | 0.002 |
| hmg-A forward primer | 200 µM | 300 nM | 0.005 |
| hmg-A reverse primer | 200 µM | 300 nM | 0.005 |
| hmg-A probe | 100 µM | 80 nM | 0.002 |
| Bovine Serum Albumin | 30% | 0.08%[b] | 0.009 |
| HPLC Molecular Biology Grade Water | N_A[c] | N_A[c] | 0.959 |

[a]The final volume of each reaction was 3 µL comprised of 2.5 µL of Master Mix and 0.5 µL of genomic DNA template.
[b]The concentration of Bovine Serum Albumin solution in the reaction, as a reagent, was 0.3%; the concentration based on the stock was 0.08%.
[c]N_A is equivalent to Not Applicable.

TABLE 15

Master Mix supporting Multiplex Assay: mo-PAT and hmg-A[a]

| Component | Stock Concentration | Final Concentration | Volume/reaction (μL) |
|---|---|---|---|
| SensiFast™ probe Lo-ROX master mix | 2x | 1x | 3.0 |
| mo-PAT forward primer | 200 μM | 900 nM | 0.027 |
| mo-PAT reverse primer | 200 μM | 900 nM | 0.027 |
| mo-PAT probe | 100 μM | 80 nM | 0.005 |
| hmg-A forward primer | 200 μM | 900 nM | 0.027 |
| hmg-A reverse primer | 200 μM | 900 nM | 0.027 |
| hmg-A probe | 100 μM | 80 nM | 0.005 |
| Bovine Serum Albumin | 30% | 0.08%[b] | 0.018 |
| HPLC Molecular Biology Grade Water | N_A[c] | N_A[c] | 1.864 |

[a]The final volume of each reaction was 6.0 μL comprised of 5.0 μL of Master Mix and 1.0 μL of genomic DNA template.
[b]The concentration of Bovine Serum Albumin solution in the reaction, as a reagent, was 0.3%; the concentration based on the stock was 0.08%.
[c]N_A is equivalent to Not Applicable PCR Analysis Genomic DNA samples isolated from collected leaf samples of DP202216 maize plants, along with copy number calibrator, negative and NTC controls, were subjected to qPCR amplification using SensiFast™ probe Lo-ROX master mix (Bioline, London, UK) in the presence of primer pair and probes specific for genes mo-PAT and AG099 and the insertion site specific for DP202216 maize which allow for the unique identification of the PHP40099 T-DNA insertion in DP202216 maize. For assay and DNA quality monitoring, maize hmg-A was included in duplex with each reaction as an endogenous control. Each qPCR reaction was set up in a total volume of 3 μL (DP202216 maize and AG099) or 6 μL (mo-PAT) with 3-ng of the isolated genomic DNA.

Results

The results of the qPCR copy number analyses of multiple generations indicate stable integration and segregation of a single copy of the genes within the T-DNA of plasmid PHP40099, with demonstrated transfer to subsequent generations.

PCR products between 76-bp and 105-bp, representing the insertion site/juntion for DP202216 maize as well as AG099 and mo-PAT genes within the T-DNA from plasmid PHP40099, were amplified and observed in leaf samples of DP202216 maize as well as eight copy number calibrator genomic controls, but were absent in each of the eight negative genomic controls and eight NTC controls. Each assay was performed at least four times with the same results observed each time. For each sample and all controls, $C_T$ values, $\Delta C_T$ values and copy numbers were calculated.

Using the maize endogenous reference gene hmg-A, a PCR product of 79-bp was amplified and observed in leaf samples of DP202216 maize as well as eight copy number calibrator and eight negative genomic controls. Amplification of the endogenous gene was not observed in the eight No Template (NTC) controls tested. The assay was performed at least four times with the same results observed each time. For each sample, and all controls, $C_T$ values, $\Delta C_T$ values and copy numbers (if applicable) were calculated.

Sensitivity of Construct-Specific PCR Analyses for DP202216 Maize

To assess the sensitivity of the construct-specific PCR assays, DP202216 maize DNA was diluted in control maize genomic DNA, resulting in test samples containing various amounts of DP202216 maize DNA (5-ng, 1-ng, 100-pg, 50-pg, 20-pg, 10-pg, 5-pg, 1-pg, 0.5-pg, 0.1-pg) in a total of 5-ng maize DNA. These various amounts of DP202216 maize DNA correspond to 100%, 20%, 2%, 1%, 0.4%, 0.2%, 0.1%, 0.01%, and 0.002% of DP202216 maize DNA in total maize genomic DNA, respectively. The various amounts of DP202216 maize DNA were subjected to real-time PCR amplification for both AG099 and mo-PAT genes. Based on these analyses, the limit of detection (LOD) was determined to be approximately 5-pg of DP202216 maize DNA in 5-ng of total DNA for mo-PAT, or 0.1%, and 10-pg of DP202216 maize DNA in 5-ng of total DNA for AG099, or 0.2%. The determined sensitivity of each assay described is sufficient for many screening applications. Each concentration was tested a total of four times with the same results observed each time. Real-time PCR analyses of DP202216 maize using event-specific and construct-specific assays confirm the stable integration and segregation of a single copy of the T-DNA of plasmid PHP40099 in leaf samples tested, as demonstrated by the quantified detection of event DP-202216-6 and AG099 and mo-PAT genes in DP-202216-6 maize. These results were reproducible among all the replicate qPCR analyses conducted. The maize endogenous reference gene assay for detection of hmg-A amplified as expected in all the test samples, negative controls and was not detected in the NTC samples. The sensitivity of the PCR methods under the conditions provided demonstrates that these assays can detect to approximately 5-pg, or 0.1% of the DP202216 maize DNA in a total of 5-ng maize genomic DNA for mo-PAT and to approximately 10-pg, or 0.2% of the DP202216 maize DNA in a total of 5-ng maize genomic DNA for AG099.

Example 8

AG099 Protein Expression and Concentration Calculations

Protein Extraction

Aliquots of processed leaf tissue samples were weighed into 1.2-ml tubes at the target weight of 10 mg. Each sample analyzed for AG099 protein concentration was extracted in chilled 0.25% ASB-14 in phosphate-buffered saline containing polysorbate 20 (PBST) and each sample analyzed for PAT protein concentration was extracted in 0.6 ml of chilled PBST. Following centrifugation, supernatants were removed, diluted in 0.25% ASB-14 in PBST (AG099) or PBST (PAT), and analyzed.

Determination of AG099 Protein Concentration

The AG099 ELISA method utilized an ELISA produced by Pioneer Hi-Bred International, Inc. to determine the concentration of the AG099 protein in samples. Standards (typically analyzed in triplicate wells) and diluted samples (typically analyzed in duplicate wells) were incubated in a plate pre-coated with a AG099 antibody. Following incubation, unbound substances were washed from the plate. A different AG099 antibody, conjugated to the enzyme horseradish peroxidase (HRP), was added to the plate and incubated. Unbound substances were washed from the plate. Detection of the bound AG099-antibody complex was accomplished by the addition of substrate, which generated a colored product in the presence of HRP. The reaction was stopped with an acid solution and the optical density (OD) of each well was determined using a plate reader.

Determination of PAT Protein Concentration

The PAT ELISA method utilized an ELISA kit produced by EnviroLogix Inc. to determine the concentration of PAT protein in samples. Standards (typically analyzed in triplicate wells) and diluted samples (typically analyzed in duplicate wells) were co-incubated with a PAT-specific antibody conjugated to the enzyme HRP in a plate pre-coated with a different PAT-specific antibody. Following incubation, unbound substances were washed from the plate. Detection of the bound PAT-antibody complex was accomplished by the addition of substrate, which generated a colored product in the presence of HRP. The reaction was stopped with an acid solution and the OD of each well was determined using a plate reader.

Calculations for Determining Protein Concentrations

SoftMax Pro GxP (Molecular Devices) microplate data software was used to perform the calculations required to convert the OD values obtained for each set of sample wells to a protein concentration value.

A standard curve was included on each ELISA plate. The equation for the standard curve was derived by the software, which used a quadratic fit to relate the OD values obtained for each set of standard wells to the respective standard concentration (ng/ml).

The quadratic regression equation was applied as follows:

$$y = Cx^2 + Bx + A$$

where x=known standard concentration and y=respective absorbance value (OD)

Interpolation of the sample concentration (ng/ml) was performed by solving for x in the above equation using the values for A, B, and C that were determined for the standard curve.

$$\text{Sample Concentration (ng/ml)} = \frac{-B + \sqrt{B^2 - 4C(A - sampleOD)}}{2C}$$

For example, given curve parameters of A=0.0476, B=0.4556, C=−0.01910, and a sample $$OD = 1.438$$

Sample Concentration =

$$\frac{-0.4556 + \sqrt{0.4556^2 - 4(-0.01910)(0.0476 - 1.438)}}{2(-0.01910)} = 3.6 \text{ ng/ml}$$

The sample concentration values were adjusted for a dilution factor expressed as 1:N by multiplying the interpolated concentration by N.

Adjusted Concentration=Interpolated Sample Concentration×Dilution Factor

For example, given an interpolated concentration of 3.6 ng/ml and a dilution factor of 1:20

Adjusted Concentration=3.6 ng/ml×20=72 ng/ml

Adjusted sample concentration values obtained from SoftMax Pro GxP software were converted from ng/ml to ng/mg sample weight as follows:

$$\begin{array}{l}\text{Sample Concentration} \\ \text{(ng protein/mg sample} \\ \text{weight)}\end{array} = \begin{array}{l}\text{Sample} \\ \text{Concentration} \\ \text{(ng/ml)}\end{array} \times \frac{\text{Extraction Buffer Volume (ml)}}{\text{Sample Target Weight (mg)}}$$

For example, sample concentration=72 ng/ml, extraction buffer volume=0.60 ml, and sample target weight=10 mg $$\begin{array}{l}\text{Sample Concentration} \\ \text{(ng protein/mg sample} \\ \text{weight)}\end{array} = 72 \text{ ng/ml} \times \frac{0.60 \text{ ml}}{10 \text{ mg}} = 4.3 \text{ ng/mg}$$

The reportable assay lower limit of quantification (LLOQ) in ng/ml was calculated as follows:

Reportable Assay LLOQ(ng/ml)=(lowest standard concentration−10%)×minimum dilution For example, lowest standard concentration=0.50 ng/ml and minimum dilution=10

Reportable Assay LLOQ(ng/ml)=(0.50 ng/ml−(0.50×0.10))×10=4.5 ng/ml

The LLOQ, in ng/mg sample weight, was calculated as follows:

$$LLOQ = \frac{\text{Reportable Assay } LLOQ}{\text{(ng/ml)}} \times \frac{\text{Extraction Buffer Volume (ml)}}{\text{Sample Target Weight (mg)}}$$

For example, reportable assay LLOQ=4.5 ng/ml, extraction buffer volume=0.60 ml, and sample target weight=10 mg $$LLOQ = 4.5 \text{ ng/ml} \times \frac{0.60 \text{ ml}}{10 \text{ mg}} = 0.27 \text{ ng/ml sample weight}$$

Means, standard deviations, and ranges for AG099 and PAT proteins for 1-copy DP202216 maize and null DP202216 maize are presented in Tables 16 and 17, respectively.

TABLE 16

Expressed AG099 Protein Concentrations in Leaf Samples

| Tissue (Growth Stage) | Generation | ng AG099/mg Tissue Dry Weight | | Sample LLOQ | Number of Samples <LLOQ/ Total Number of Samples Reported |
|---|---|---|---|---|---|
| | | Mean ± SD | Range | | |
| 1-Copy DP202216 Maize | | | | | |
| Leaf (V5) | T2 | 0.045 ± 0.0092 | 0.034-0.059 | 0.027 | 0/5 |
| Leaf (V5) | F1*[1] | 0.062 ± 0.012 | 0.044-0.078 | 0.027 | 0/5 |
| Leaf (V9) | T2 | 0.28 ± 0.058 | 0.19-0.34 | 0.027 | 0/5 |
| Leaf (V9) | F1*[1] | 0.40 ± 0.024 | 0.37-0.43 | 0.027 | 0/5 |
| Null DP202216 Maize | | | | | |
| Leaf (V5) | T2 | <0.027 ± 0 | <0.027 | 0.027 | 5/5 |
| Leaf (V5) | F1*[1] | <0.027 ± 0 | <0.027 | 0.027 | 5/5 |
| Leaf (V9) | T2 | 0.16 ± 0.023 | 0.14-0.19 | 0.027 | 0/5 |
| Leaf (V9) | F1*[1] | 0.31 ± 0.025 | 0.28-0.35 | 0.027 | 0/5 |

TABLE 17

Expressed PAT Protein Concentrations in Leaf Samples

| Tissue (Growth Stage) | Generation | ng PAT/mg Tissue Dry Weight | | Sample LLOQ | Number of Samples <LLOQ/ Total Number of Samples Reported |
|---|---|---|---|---|---|
| | | Mean ± SD | Range | | |
| 1-Copy DP202216 Maize | | | | | |
| Leaf (V9) | T2 | 86 ± 5.4 | 78-90 | 0.11 | 0/5 |
| Leaf (V9) | F1*[1] | 55 ± 4.6 | 48-60 | 0.11 | 0/5 |

Example 9

Transformation of Maize by *Agrobacterium* Transformation and Regeneration of Transgenic Plants Containing Event DP-202216-6

DP-202216-6 maize event was produced by *Agrobacterium*-mediated transformation with plasmid PHP40099. This protocol for generating transgenic maize plants used engineered *Agrobacterium tumefaciens* and immature embryos of a transformable maize line using moPAT as the selectable marker. Briefly, *Agrobacterium tumefaciens* strain (JTLBA4404) containing the plasmid described above was prepared using standard growth conditions including incubating the bacteria in the dark at 28 C prior to using for agro infection. Immature embryos were harvested from the transformable maize line ears at about 8-11 days after pollination with the embryo size ranging about 1.3 to 1.8 mm in length. *Agrobacterium* cell culture was used to infect the isolated immature embryos by adding the *Agrobacterium* cell culture to tubes containing embryos and culturing the embryos with the scutellum side up on co-cultivation medium at 21 C for about 3 days in dark. After 3 days, such cultured embryos were transferred to growth media containing carbenicillin to control *Agrobacterium* growth and cultured at 28 C in dark for about 7 days, followed by transfer to another growth media and cultured at 28 C in dark for about 21 days. The embryo callus was transferred to growth media containing bialaphos and cultured further at 28 C under dark with transfer to fresh media at 14-day interval. Callus were transferred to embryo maturation media for approximately 14 at 28 C in dark. Mature embryos were transferred to germination medium and placed in light at 28 C for about 7 days. Upon shoot and root development, the plantlets were transferred for growth under light at 28 C for about 7 days in tubes. After shoots were developed, the plantlets were sent to greenhouse for T1 seed production and further analysis.

Example 10

Transgene Expression in Maize DP-202216-6

Figure 2B:
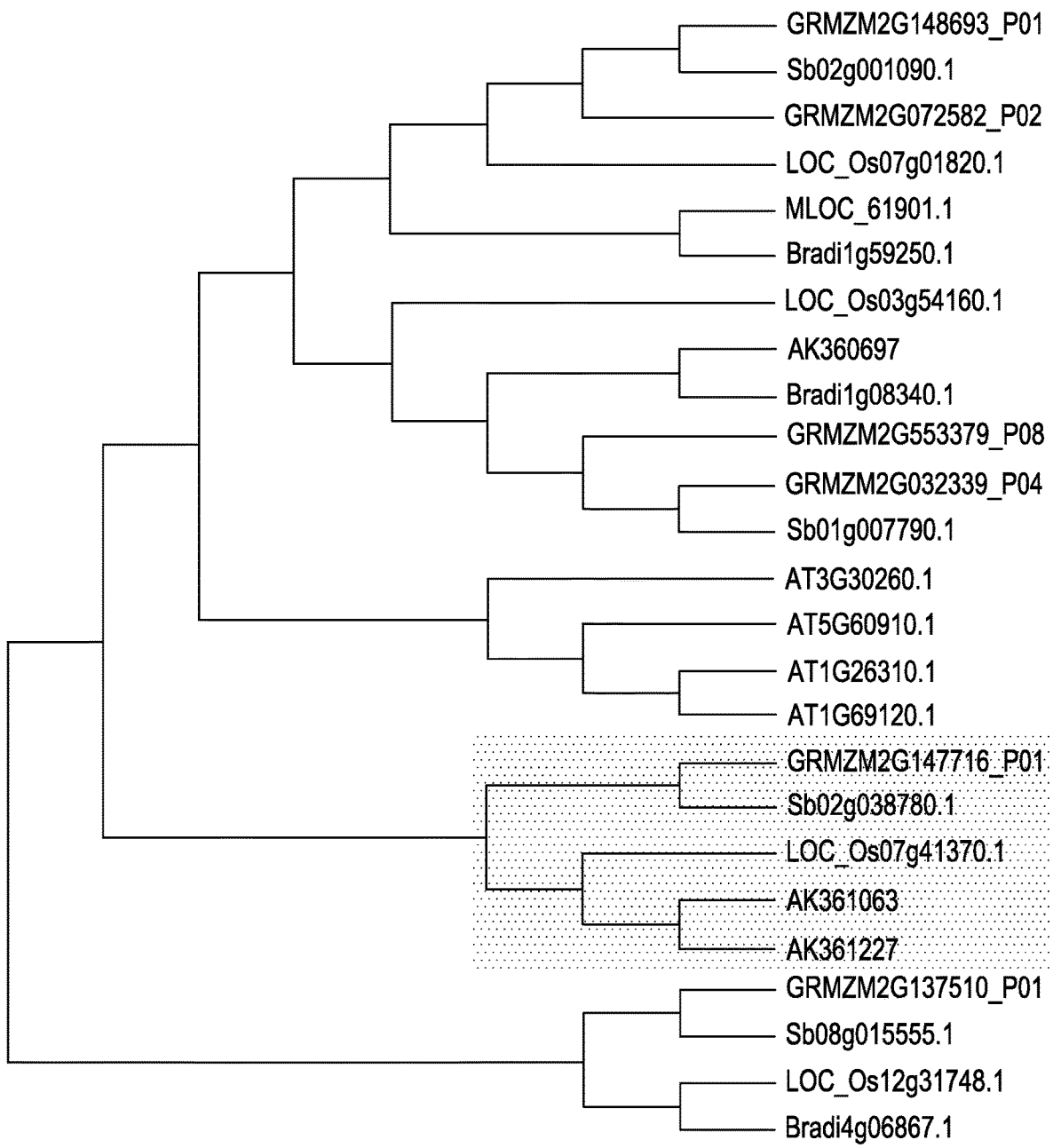
FIG. 2B shows the phylogenetic analysis of ZMM28 (GRMZM2G147716 P01) with other AP1-FUL clade members from representative plant species. The clade containing ZMM28 is highlighted in dotted region.
Figure 2C:
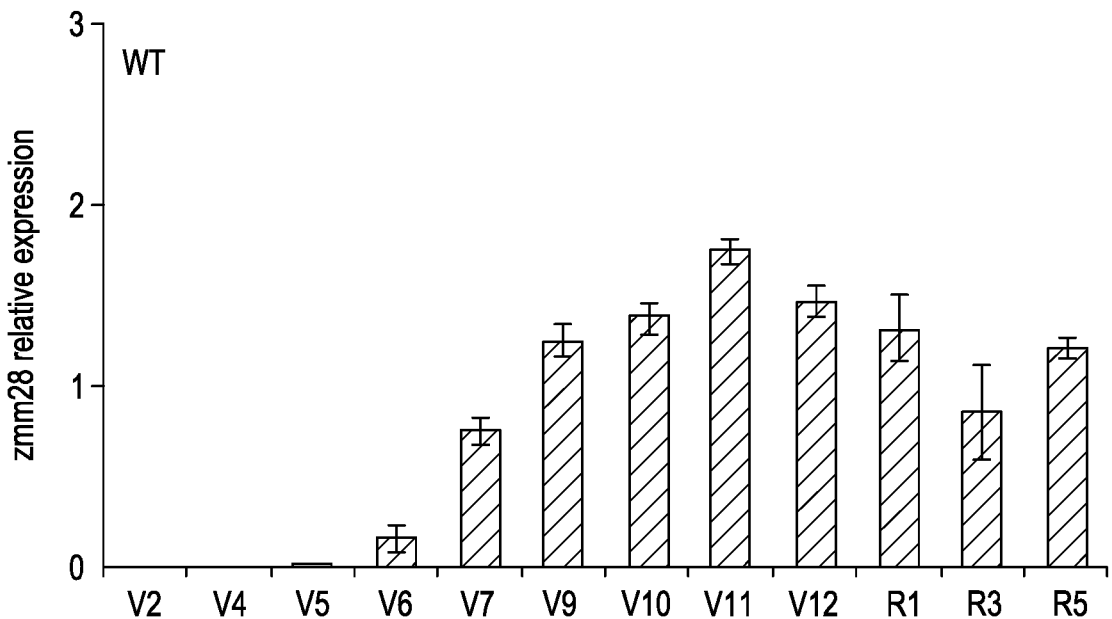
FIG. 2C shows the relative expression of zmm28 gene in the wild-type (WT) background (control) leaf tissue for the various growth stages.
Figure 2D:
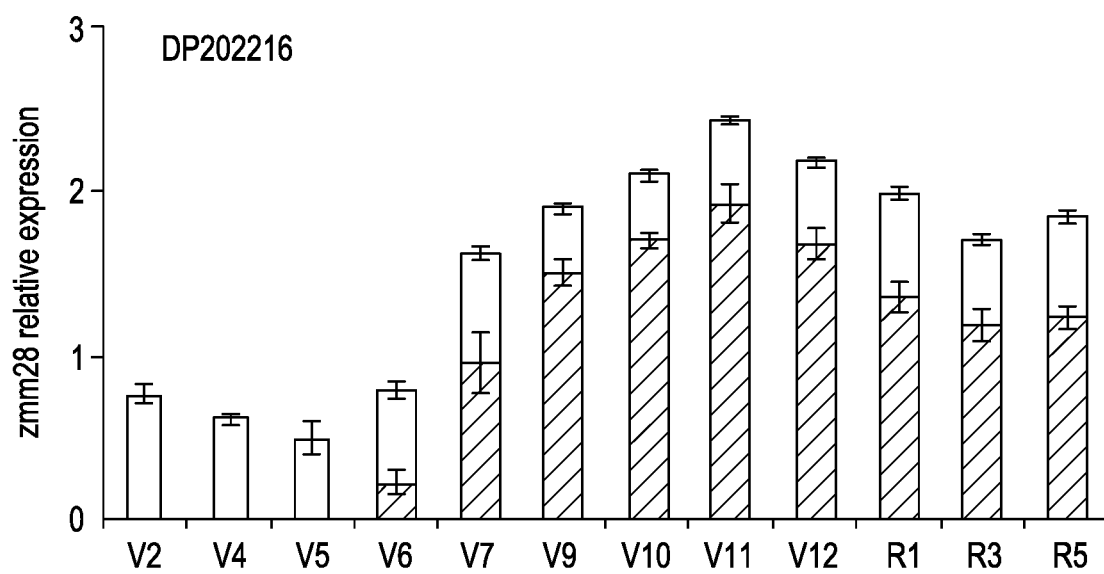
FIG. 2D shows the relative expression of zmm28 gene in leaf tissue of Event DP202216 (open bars) and wild-type (WT) background (hashed bars) for the various growth stages. Error bars represent standard error. Total (native and transgenic) zmm28 expression is significantly greater in transgenic plants than in the control at all growth stages ($p<0.05$).
Figure 2E:
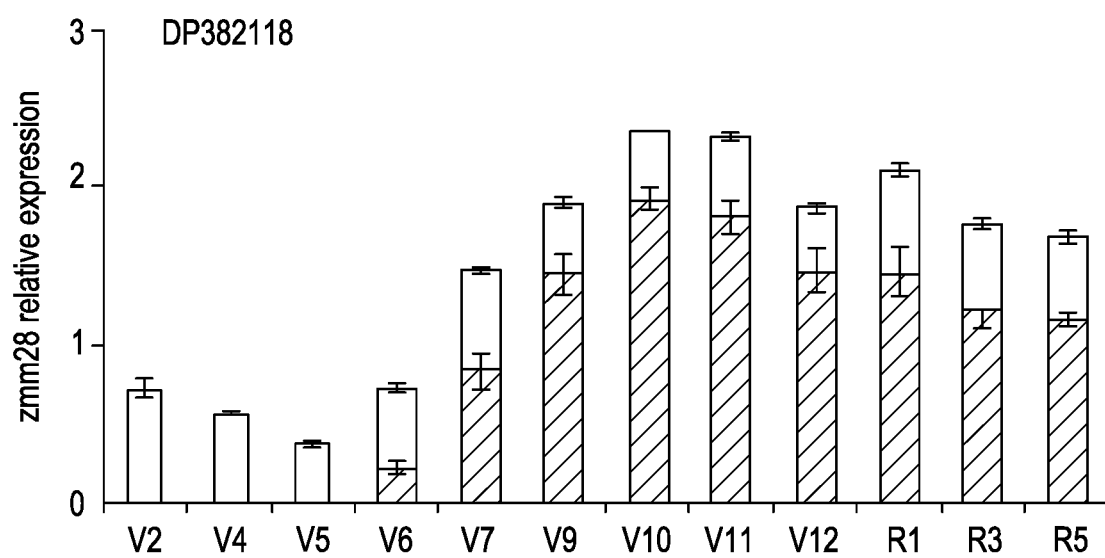
FIG. 2E shows the relative expression of zmm28 gene in Event 18 leaf tissue during different vegetative (V) and reproductive (R) stages.

Compared to zmm28 expression in control plants, in event 16, the zmm28 expression is observed in early growth stages (V2-V5) in leaf due to the presence of the transgenic zmm28, and then has a similar expression profile to that observed for control maize from V6 through senescence (FIGS. 2d and e). Expression of zmm28 is also found in root, stem, shoot apical meristem (SAM), tassel, ear and kernel in the maize events. Concentrations of ZMM28 protein in leaf in the two events follow a similar temporal profile to that for RNA levels and occur at sub-ppm levels. However, there is no strong correlative relationship between transcript level and protein expression in the root, as measured in this study.

Subcellular localization experiments of ZmGos2-zmm28 transgenic protein with either a N-terminal or C-terminal *Aequorea coerulescens* green fluorescent protein (AcGFP1) tag indicated localization to the nucleus in independent stably-transformed maize events. This result was confirmed in transient assays including a nuclear marker protein, histone H2B (GRMZM2G401147), fused to mKate2.

Example 11

Extended and Increased Expression of AG099 and Agronomic Characterization

A series of morphometric measurements were performed in the ZmGos2-zmm28 events. The extended and increased zmm28 gene expression resulted in observed early seedling growth, leaf biomass and total leaf area. Sample number tested for V2-V8 is 96 and about 48 for V10. Dry weight of leaves at the V8 stage from about 48 samples. Total leaf area at R1 stage was from 24 samples. Leaf carbon exchange rate at V11 stage was measured from 60 samples. Photosynthetic electron transport rate at V11 was determined from about 60 samples; N uptake from about 31 for control and 29 for DP202216 and DP382118. Assimilated N content in leaf and root, n=19 for control and DP382118, and n=20 for DP202216.

Plant height of DP202216 and DP382118 was significantly greater than that of controls from V2 to V7, averaged across all tested hybrids. Leaf dry weight was increased 11% and 22% for DP202216 and DP382118, respectively, at the V8 stage. Furthermore, both ZmGos2-zmm28 events had a greater total leaf area than WT, increasing by 4% on average at the R1 stage.

Modulation of zmm28 expression in maize resulted in improvement of certain measured vegetative phenotypes. These included an increase of early seedling vigor, measured as an increase of plant height and leaf biomass, as well as an increase of total leaf area at the R1 stage. Plant height was measured from the soil surface to the collar of the youngest fully expanded leaf. For leaf dry weight measurements, all the leaves collected from each individual plant, placed in a paper bag and dried at 70° C. for 72 hours, or until complete dryness. The samples were weighed after equilibrating at room temperature for 1 hour. Total leaf area was measured with field plot grown plants. Briefly, the plants were collected from the field plot by cutting the stalk at the soil surface at the R1 growth stage, then all the leaves from an individual plant were excised and leaf area of each leaf was measured with a Li-3100C leaf area meter (Li-Cor, Lincoln, Nebr. USA).

Example 12

Increased Photosynthesis and Photosynthetic Enzyme Activity

Photosynthesis was determined to see if this attribute was altered in the transgenic events. Photosynthesis, expressed as $CO_2$ exchange rate (CER) and photosynthetic electron transport rate (ETR), was measured from field-pot grown DP202216 and DP382118 plants in two hybrid backgrounds together with their controls at the V11 growth stage. The CER and ETR in DP-202216-6 were increased by 10% and 8%, respectively; while CER and ETR in DP382118 were increased 10% and 9%, respectively. Increased and extended expression of zmm28 in maize resulted in increased green leaf area at both vegetative and reproductive stages and increased photosynthesis rate per leaf area. This is supported by observed increases in both ETR and enzyme activity of key C4 cycle photosynthetic enzymes.

Extended and increased zmm28 expression resulted in increased C4 photosynthetic enzyme activities and nitrate reductase activity, but not glutamine synthase activity. Gas exchange studies revealed increases in $CO_2$ fixation rate in both DP202216 and DP382118. To determine whether photosynthesis-relevant enzyme activities were altered in the events, specific activities of major C4 photosynthetic enzymes were examined at two growth stages, V4 and V11. These two growth stages were chosen because at V4, only transgenic zmm28 is expressed (as measured), while at V11 both native and transgenic zmm28 are expressed (detectable). Statistically significant increases in activities were observed in one or both transgenic events for PEPC and NADP-MDH at V4, and for PEPC, NADP-MDH, and PPDK at V11. The most consistent effect was observed for NADP-MDH, with both events at V11 and event DP382118 at V4 having a significant increase in enzyme specific activity. These increases in the C4 photosynthetic enzyme activities are consistent with the increase in $CO_2$ fixation rate.

Nitrate reductase (NR) catalyzes the rate-limiting step in nitrate assimilation by initiating reduction of nitrate to organic forms, and this enzyme is well-established as a key regulator of N assimilation and acquisition. NR specific activity was assayed in leaf and root tissues from maize events DP202216, DP382118, and control plants at the V4 and V11 growth stages. The results showed that NR enzyme activity was significantly increased in DP202216 and DP382118 in leaf tissue at both growth stages. The increase of NR activity is consistent with the N uptake and assimilation results. However, there was no significant difference in NR activity in root tissue between the two events and control lines.

The specific activity of another key N assimilation enzyme—glutamine synthetase (GS)—was also examined in the same tissue samples used for the NR assays. GS activities did not show a significant difference between DP202216 and DP382118 and controls in either leaf or root. This may indicate that no additional GS activity is needed for the increased N assimilation measured in DP202216 and DP382118, given the extended and increased expression of zmm28 in the transgenic plants. Results showed that ZmGos2-zmm28 plants exhibit enhanced nitrogen metabolism, along with increaed nitrogen uptake rate and assimilation capacity.

Example 13

Increased N Uptake and Assimilation

Improving nitrogen (N) utilization is an attribute to increase crop yield. It was investigated whether extended and increased expression of zmm28 could improve N uptake. DP202216, DP382118, and control plants were grown hydroponically in a growth chamber and were analyzed at the V8 stage. Results demonstrated that N uptake was increased by 16% in DP202216 and 18% in DP382118 compared to controls (P<0.05). In addition, nitrogen assimilation, measured as the amount of assimilated N in leaf and root tissues at the R1 growth stage, was significantly greater in DP202216 and DP382118. At the R1 Stage, DP202216 and DP382118 had increased assimilated N over that of controls; 10% and 12%, respectively, in the leaf; and 23% and 17%, respectively, in the root (P<0.05).

For response under the Examples herein, separate statistical analyses were conducted using SAS software, Version 9.4 (SAS Institute Inc., Cary, N.C., USA) or ASReml 3.0 (VSN International, Hemel Hempstead, U K, 2009). Linear mixed models were fitted per the design of each experiment, event means were estimated (known as empirical best linear unbiased estimators), and 95% confidence intervals for those estimates were calculated.

Statistical assumptions of the linear mixed models (i.e. normality, independence, and homogeneous variance of the residual error) were evaluated using plots of studentized conditional residuals. For nitrate reductase, a log transformation was conducted prior to analysis to remedy departures from assumptions. Results for nitrate reductase were back-transformed to the original data scale prior to reporting. The assumptions were satisfied for all other responses. Each of the transgenic events was compared to the respective control using two-tailed t-tests of differences between the estimates. In experiments with multiple hybrids, when interaction of event and hybrid was found significant, the comparisons were conducted within each hybrid. The approximated degrees of freedom for the statistical tests were derived using the Kenward-Roger method.

What is claimed is:

1. A corn plant, seed, cell or part thereof comprising event DP-202216-6, wherein the event comprises the nucleotide sequence set forth in SEQ ID NO: 14, and wherein a representative sample of seed comprising the event has been deposited with American Type Culture Collection (ATCC) with Accession No. PTA-124653.

2. The corn plant, seed, cell, or plant part of claim 1, wherein the plant part is selected from the group consisting of pericarp, pollen, ovule, flower, grain, shoot, root, stalk, silk, tassel, ear, and leaf tissue.

3. A method of increasing grain yield of a population of maize plants in a field, the method comprising growing a population of maize plants comprising Event DP-202216-6 in a field and thereby increasing grain yield of the population of maize plants compared to a control plant not comprising the Event DP-202216-6, wherein the Event comprises the nucleotide sequence set forth in SEQ ID NO:14 and wherein a representative sample of seed comprising the Event has been deposited with American Type Culture Collection (ATCC) with Accession No. PTA-124653.

4. The method of claim 3 wherein the population of maize plants are grown under abiotic stress.

5. The method of claim 4, wherein the abiotic stress is low nitrogen.

6. The method of claim 5, wherein the low nitrogen is about 25% to about 75% reduction in the amount of nitrogen normally applied to grow hybrid corn plants in the field.

* * * * *

SEQUENCE LISTING

```
<160> NUMBER OF SEQ ID NOS: 32

<210> SEQ ID NO 1
<211> LENGTH: 251
<212> TYPE: PRT
<213> ORGANISM: Zea mays

<400> SEQUENCE: 1

Met Gly Arg Gly Pro Val Gln Leu Arg Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Leu Ile Val Phe
        35                  40                  45

Ser Thr Lys Gly Lys Leu Tyr Glu Tyr Ser Ser His Ser Ser Met Glu
    50                  55                  60

Gly Ile Leu Glu Arg Tyr Gln Arg Tyr Ser Phe Glu Glu Arg Ala Val
65                  70                  75                  80

Leu Asn Pro Ser Ile Glu Asp Gln Ala Asn Trp Gly Asp Glu Tyr Val
                85                  90                  95

Arg Leu Lys Ser Lys Leu Asp Ala Leu Gln Lys Ser Gln Arg Gln Leu
            100                 105                 110

Leu Gly Glu Gln Leu Ser Ser Leu Thr Ile Lys Glu Leu Gln Gln Leu
        115                 120                 125

Glu Gln Gln Leu Asp Ser Ser Leu Lys His Ile Arg Ser Arg Lys Asn
    130                 135                 140

Gln Leu Met Phe Asp Ser Ile Ser Ala Leu Gln Lys Lys Glu Lys Ala
145                 150                 155                 160

Leu Thr Asp Gln Asn Gly Val Leu Gln Lys Phe Met Glu Ala Glu Lys
                165                 170                 175

Glu Lys Asn Lys Ala Leu Met Asn Ala Gln Leu Arg Glu Gln Gln Asn
            180                 185                 190

Gly Ala Ser Thr Ser Ser Pro Ser Leu Ser Pro Pro Ile Val Pro Asp
        195                 200                 205

Ser Met Pro Thr Leu Asn Ile Gly Pro Cys Gln His Arg Gly Ala Ala
    210                 215                 220

Glu Ser Glu Ser Glu Pro Ser Pro Ala Pro Ala Gln Ala Asn Arg Gly
225                 230                 235                 240

Asn Leu Pro Pro Trp Met Leu Arg Thr Val Lys
                245                 250

<210> SEQ ID NO 2
<211> LENGTH: 857
<212> TYPE: DNA
<213> ORGANISM: Zea mays

<400> SEQUENCE: 2
ccccatcacc attgctgcga cgagagtgag cgggagaggg taggtggcga ggcggcggag    60
```

```
atggggcggg ggccggtgca gctgcgccgg atcgagaaca agatcaaccg ccaggtgacc      120
ttctccaagc gccggaacgg gctgctgaag aaggcccacg agatctccgt gctctgcgac      180
gcagaggtcg cgctcatcgt cttctccact aaggggaagc tctacgagta ctctagccat      240
tccagcatgg aaggcattct tgagcgttac cagcgttact catttgaaga aagggcagta      300
cttaacccaa gtattgaaga ccaggcaaat tggggagatg aatatgtccg gttaaaatcc      360
aaacttgatg cacttcagaa gagtcaaagg cagctgttag agaacaatt gagttcactg       420 accataaaag aactccagca actggagcaa caactggaca gttctttgaa gcatattagg      480
tcaagaaaga atcagctcat gttcgattca atttccgcgc ttcagaaaaa ggagaaagca      540
cttacagatc aaaacggtgt cctgcaaaag ttcatggagg cagagaagga gaaaaacaag      600
gctttgatga acgcgcagct ccgggagcag caaaatggag catcaacaag ctccccatca      660
ctttcaccac caatagttcc agattccatg ccaactctaa atatagggcc atgtcaacat      720
agaggggcag cagaatctga gtctgaaccg tctcctgctc ctgcacaagc aaacagggc       780 aacctgccac catggatgct ccgcactgtc aagtaacagg tgaggtcttc ccagtgtagt      840
tttgcagctg atctcga                                                     857
```

<210> SEQ ID NO 3
<211> LENGTH: 857
<212> TYPE: DNA
<213> ORGANISM: Zea mays

<400> SEQUENCE: 3

```
taattattgg ctgtaggatt ctaaacagag cctaaatagc tggaatagct ctagccctca       60
atccaaacta atgatatcta tacttatgca actctaaatt tttattctaa aagtaatatt      120 tcattttgt caacgagatt ctcactcta ttccacaatc ttttgaagca atatttacct       180
taaatctgta ctctatacca ataatcatat attctattat ttattttat ctctctccta       240 aggagcatcc ccctatgtct gcatggcccc cgcctcgggt cccaatctct tgctctgcta      300
gtagcacaga agaaaacact agaaatgact tgcttgactt agagtatcag ataaacatca      360
tgtttactta actttaattt gtatcggttt ctactatttt tataatattt ttgtctctat      420
agatactacg tgcaacagta taatcaacct agtttaatcc agagcgaagg atttttttact    480 aagtacgtga ctccatatgc acagcgttcc ttttatggtt cctcactggg cacagcataa      540
acgaaccctg tccaatgttt tcagcgcgaa caaacagaaa ttccatcagc gaacaaacaa      600
catacatgcg agatgaaaat aaataataaa aaaagctccg tctcgatagg ccggcacgaa      660
tcgagagcct ccatagccag tttttttccat cggaacggcg gttcgcgcac ctaattatat     720
gcaccacacg cctataaagc caaccaaccc gtcggagggg cgcaagccag acagaagaca      780
gcccgtcagc ccctctcgtt tttcatccgc cttcgcctcc aaccgcgtgc gctccacgcc      840
tcctccagga aagcgag                                                     857
```

<210> SEQ ID NO 4
<211> LENGTH: 1013
<212> TYPE: DNA
<213> ORGANISM: Zea mays

<400> SEQUENCE: 4

```
gtacgccgct cgtcctcccc ccccccctc tctaccttct ctagatcggc gttccggtcc        60
atgcatggtt agggcccggt agttctactt ctgttcatgt ttgtgttaga tccgtgtttg      120
tgttagatcc gtgctgctag cgttcgtaca cggatgcgac ctgtacgtca gacacgttct      180
```

```
gattgctaac ttgccagtgt ttctctttgg ggaatcctgg gatggctcta gccgttccgc      240
agacgggatc gatttcatga ttttttttgt ttcgttgcat agggtttggt ttgccctttt      300
cctttatttc aatatatgcc gtgcacttgt ttgtcgggtc atctttcat gctttttttt       360 gtcttggttg tgatgatgtg gtctggttgg gcggtcgttc tagatcggag tagaattctg      420
tttcaaacta cctggtggat ttattaattt tggatctgta tgtgtgtgcc atacatattc      480
atagttacga attgaagatg atggatggaa atatcgatct aggataggta tacatgttga      540
tgcgggtttt actgatgcat atacagagat gcttttttgtt cgcttggttg tgatgatgtg     600
gtgtggttgg gcggtcgttc attcgttcta gatcggagta gaatactgtt tcaaactacc      660
tggtgtattt attaattttg gaactgtatg tgtgtgtcat acatcttcat agttacgagt      720
ttaagatgga tggaaatatc gatctaggat aggtatacat gttgatgtgg gttttactga      780
tgcatataca tgatggcata tgcagcatct attcatatgc tctaaccttg agtacctatc      840
tattataata aacaagtatg ttttataatt attttgatct tgatatactt ggatgatggc      900
atatgcagca gctatatgtg gattttttta gccctgcctt catacgctat ttatttgctt      960
ggtactgttt cttttgtcga tgctcaccct gttgtttggt gttacttctg cag            1013

<210> SEQ ID NO 5
<211> LENGTH: 7470
<212> TYPE: DNA
<213> ORGANISM: Artificial Sequence
<220> FEATURE:
<223> OTHER INFORMATION: T-DNA from plasmid

<400> SEQUENCE: 5
gtttacccgc caatatatcc tgtcaaacac tgatagttta aactgaaggc gggaaacgac       60
aatctgatca tgagcggaga attaagggag tcacgttatg accccgccg atgacgcggg       120 acaagccgtt ttacgtttgg aactgacaga accgcaacgt tgaaggagcc actcagcaag      180
ctggtacgat tgtaatacga ctcactatag ggcgaattga gcgctgttta aacgctcttc      240
aactggaaga gcggttacta ccggctggat ggcggggcct tgatcgtgca ccgccggcgt      300
ccggactaac taactagtcg agctagttac cctatgaggt gacatgaagc gctcacggtt      360
actatgacgg ttagcttcac gactgttggt ggcagtagcg tacgacttag ctatagttcc      420
ggacttaccc ttaagataac ttcgtatagc atacattata cgaagttatg ggcccaccgg      480
tggtaccgag ctcgtttaaa cgctcttcaa ctggaagagc ggttaccaga gctggtcacc      540
tttgtccacc aagatggaac tggcgcgcct cattaattaa gtcagcggcc gctctagttg      600
aagacacgtt catgtcttca tcgtaagaag acactcagta gtcttcggcc agaatggcca      660
tctggattca gcaggcctag aaggccattt atcgctatca actttgtata gaaaagttgg      720
gccgaattcg agctcggtac ggccagaatg gccctggtaa ttattggctg taggattcta      780
aacagagcct aaatagctgg aatagctcta gccctcaatc caaactaatg atatctatac      840
ttatgcaact ctaaattttt attctaaaag taatatttca ttttttgtcaa cgagattctc      900 tactctattc cacaatcttt tgaagcaata tttaccttaa atctgtactc tataccaata      960
atcatatatt ctattattta tttttatctc tctcctaagg agcatccccc tatgtctgca     1020 tggccccccgc ctcgggtccc aatctcttgc tctgctagta gcacagaaga aaacactaga     1080
aatgacttgc ttgacttaga gtatcagata aacatcatgt ttacttaact ttaatttgta     1140
tcggtttcta ctatttttat aatatttttg tctctataga tactacgtgc aacagtataa     1200
```

```
tcaacctagt ttaatccaga gcgaaggatt ttttactaag tacgtgactc catatgcaca    1260
gcgttccttt tatggttcct cactgggcac agcataaacg aaccctgtcc aatgttttca    1320
gcgcgaacaa acagaaattc catcagcgaa caaacaacat acatgcgaga tgaaaataaa    1380
taataaaaaa agctccgtct cgataggccg gcacgaatcg agagcctcca tagccagttt    1440
tttccatcgg aacggcggtt cgcgcaccta attatatgca ccacacgcct ataaagccaa    1500
ccaacccgtc ggaggggcgc aagccagaca gaagacagcc cgtcagcccc tctcgttttt    1560
catccgcctt cgcctccaac cgcgtgcgct ccacgcctcc tccaggaaag cgaggatctc    1620
ccccaaatcc acccgtcggc acctccgctt caaggtacgc cgctcgtcct cccccccccc    1680
cctctctacc ttctctagat cggcgttccg gtccatgcat ggttagggcc cggtagttct    1740
acttctgttc atgtttgtgt tagatccgtg tttgtgttag atccgtgctg ctagcgttcg    1800
tacacggatg cgacctgtac gtcagacacg ttctgattgc taacttgcca gtgtttctct    1860
ttggggaatc ctgggatggc tctagccgtt ccgcagacgg gatcgatttc atgatttttt    1920
ttgtttcgtt gcatagggtt tggtttgccc ttttccttta tttcaatata tgccgtgcac    1980
ttgtttgtcg ggtcatcttt tcatgctttt ttttgtcttg gttgtgatga tgtggtctgg    2040
ttgggcggtc gttctagatc ggagtagaat tctgtttcaa actacctggt ggatttatta    2100
attttggatc tgtatgtgtg tgccatacat attcatagtt acgaattgaa gatgatggat    2160
ggaaatatcg atctaggata ggtatacatg ttgatgcggg ttttactgat gcatatacag    2220
agatgctttt tgttcgcttg gttgtgatga tgtggtgtgg ttgggcggtc gttcattcgt    2280
tctagatcgg agtagaatac tgtttcaaac tacctggtgt atttattaat tttggaactg    2340
tatgtgtgtg tcatacatct tcatagttac gagtttaaga tggatggaaa tatcgatcta    2400
ggataggtat acatgttgat gtgggtttta ctgatgcata tacatgatgg catatgcagc    2460
atctattcat atgctctaac cttgagtacc tatctattat aataaacaag tatgttttat    2520
aattattttg atcttgatat acttggatga tggcatatgc agcagctata tgtgattttt    2580
tttagccctg ccttcatacg ctatttattt gcttggtact gtttcttttg tcgatgctca    2640
ccctgttgtt tggtgttact tctgcaggtc gactctagga tccaagcttg gcctagaagg    2700
ccagcttcaa gtttgtacaa aaaagcaggc tccgcggccg ccccccttcc ccatcaccat    2760
tgctgcgacg agagtgagcg ggagagggta ggtggcgagg cggcggagat ggggcggggg    2820
ccggtgcagc tgcgccggat cgagaacaag atcaaccgcc aggtgacctt ctccaagcgc    2880
cggaacgggc tgctgaagaa ggcccacgag atctccgtgc tctgcgacgc agaggtcgcg    2940
ctcatcgtct tctccactaa ggggaagctc tacgagtact ctagccattc cagcatggaa    3000
ggcattcttg agcgttacca gcgttactca tttgaagaaa gggcagtact aacccaagt     3060
attgaagacc aggcaaattg gggagatgaa tatgtccggt taaaatccaa acttgatgca    3120
cttcagaaga gtcaaaggca gctgttagga gaacaattga gttcactgac cataaaagaa    3180
ctccagcaac tggagcaaca actggacagt tctttgaagc atattaggtc aagaaagaat    3240
cagctcatgt tcgattcaat ttccgcgctt cagaaaaagg agaaagcact tacagatcaa    3300
aacggtgtcc tgcaaaagtt catggaggca gagaaggaga aaaacaaggc tttgatgaac    3360
gcgcagctcc gggagcagca aaatggagca tcaacaagct ccccatcact ttcaccacca    3420
atagttccag attccatgcc aactctaaat atagggccat gtcaacatag aggggcagca    3480
gaatctgagt ctgaaccgtc tcctgctcct gcacaagcaa acaggggcaa cctgccacca    3540
tggatgctcc gcactgtcaa gtaacaggtg aggtcttccc agtgtagttt tgcagctgat    3600
```

```
ctcgaaaggg tgggcgcgcc gacccagctt tcttgtacaa agtggccgtt aacggatcca    3660
gacttgtcca tcttctggat tggccaactt aattaatgta tgaaataaaa ggatgcacac    3720
atagtgacat gctaatcact ataatgtggg catcaaagtt gtgtgttatg tgtaattact    3780
agttatctga ataaaagaga aagagatcat ccatatttct tatcctaaat gaatgtcacg    3840
tgtctttata attctttgat gaaccagatg catttcatta accaaatcca tatacatata    3900
aatattaatc atatataatt aatatcaatt gggttagcaa aacaaatcta gtctaggtgt    3960
gttttgcgaa ttgcggcaag cttgcggccg ccccgggcaa ctttattata caaagttgat    4020
agataaatcc tgaggatctg tcttcctaa ggacccggga tatcggaccg attaaacttt    4080
aattcggtcc gataacttcg tatagcatac attatacgaa gttatacctg gtggcgccgc    4140
tagcctgcag tgcagcgtga cccggtcgtg cccctctcta gagataatga gcattgcatg    4200
tctaagttat aaaaaattac cacatatttt ttttgtcaca cttgtttgaa gtgcagttta    4260
tctatcttta tacatatatt taaactttac tctacgaata ataatctaa tagtactaca    4320 ataatatcag tgttttagag aatcatataa atgaacagtt agacatggtc taaggacaa    4380 ttgagtattt tgacaacagg actctacagt tttatctttt tagtgtgcat gtgttctcct    4440 tttttttgc aaatagcttc acctatataa tacttcatcc attttattag tacatccatt    4500
tagggtttag ggtaatggt ttttatagac taattttttt agtacatcta ttttattcta    4560
ttttagcctc taaattaaga aaactaaaac tctattttag ttttttttatt taataattta    4620 gatataaaat agaataaaat aaagtgacta aaaattaaac aaatacctt taagaaatta    4680 aaaaaactaa ggaaacattt tcttgtttc gagtagataa tgccagcctg ttaaacgccg    4740
tcgacgagtc taacgacac caaccagcga accagcagcg tcgcgtcggg ccaagcgaag    4800
cagacggcac ggcatctctg tcgctgcctc tggaccctc tcgagagttc cgctccaccg    4860
ttggacttgc tccgctgtcg gcatccagaa attgcgtggc ggagcggcag acgtgagccg    4920
gcacggcagg cggcctcctc ctcctctcac ggcaccggca gctacggggg attccttcc    4980 caccgctcct tcgctttccc ttcctcgccc gccgtaataa atagacaccc cctccacacc    5040
ctctttcccc aacctcgtgt tgttcggagc gcacacacac acaaccagat ctccccaaa    5100 tccacccgtc ggcacctccg cttcaaggta cgccgctcgt cctcccccc cccctctct    5160 accttctcta gatcggcgtt ccggtccatg catggttagg gcccggtagt tctacttctg    5220
ttcatgtttg tgttagatcc gtgtttgtgt tagatccgtg ctgctagcgt tcgtacacgg    5280
atgcgacctg tacgtcagac acgttctgat tgctaacttg ccagtgtttc tctttgggga    5340
atcctgggat ggctctagcc gttccgcaga cgggatcgat ttcatgattt tttttgtttc    5400
gttgcatagg gtttggtttg ccctttcct ttatttcaat atatgccgtg cacttgtttg    5460
tcgggtcatc ttttcatgct tttttttgtc ttggttgtga tgatgtggtc tggttgggcg    5520
gtcgttctag atcggagtag aattctgttt caaactacct ggtggatta ttaattttgg    5580 atctgtatgt gtgtgccata catattcata gttacgaatt gaagatgatg gatggaaata    5640
tcgatctagg ataggtatac atgttgatgc gggttttact gatgcatata cagagatgct    5700
ttttgttcgc ttggttgtga tgatgtggtg tggttgggcg gtcgttcatt cgttctagat    5760
cggagtagaa tactgtttca aactacctgg tgtatttatt aatttggaa ctgtatgtgt    5820 gtgtcataca tcttccatagt tacgagtta agatggatgg aaatatcgat ctaggatagg    5880
tatacatgtt gatgtgggtt ttactgatgc atatacatga tggcatatgc agcatctatt    5940
```

```
catatgctct aaccttgagt acctatctat tataataaac aagtatgttt tataattatt    6000
ttgatcttga tatacttgga tgatggcata tgcagcagct atatgtggat ttttttagcc    6060
ctgccttcat acgctattta tttgcttggt actgtttctt ttgtcgatgc tcaccctgtt    6120
gtttggtgtt acttctgcag gtcgactcta gaggatcaat tcgctagcga agttcctatt    6180
ccgaagttcc tattctctag aaagtatagg aacttcagat ccaccgggat ccacacgaca    6240
ccatgtcccc cgagcgccgc cccgtcgaga tccgcccggc caccgccgcc gacatggccg    6300
ccgtgtgcga catcgtgaac cactacatcg agacctccac cgtgaacttc cgcaccgagc    6360
cgcagacccc gcaggagtgg atcgacgacc tggagcgcct ccaggaccgc tacccgtggc    6420
tcgtggccga ggtggagggc gtggtggccg gcatcgccta cgccggcccg tggaaggccc    6480
gcaacgccta cgactggacc gtggagtcca ccgtgtacgt gtcccaccgc caccagcgcc    6540
tcggcctcgg ctccaccctc tacacccacc tcctcaagag catggaggcc cagggcttca    6600
agtccgtggt ggccgtgatc ggcctcccga acgaccgtc cgtgcgcctc cacgaggccc    6660
tcggctacac cgcccgcggc accctccgcg ccgccggcta caagcacggc ggctggcacg    6720
acgtcggctt ctggcagcgc gacttcgagc tgccggcccc gccgcgcccg gtgcgcccgg    6780
tgacgcagat ctgagtcgaa acctagactt gtccatcttc tggattggcc aacttaatta    6840
atgtatgaaa taaaggatg cacacatagt gacatgctaa tcactataat gtgggcatca    6900
aagttgtgtg ttatgtgtaa ttactagtta tctgaataaa agagaaagag atcatccata    6960
tttcttatcc taaatgaatg tcacgtgtct ttataattct ttgatgaacc agatgcattt    7020
cattaaccaa atccatatac atataaatat taatcatata taattaatat caattgggtt    7080
agcaaaacaa atctagtcta ggtgtgtttt gcgaatgcgg ccctagcgta tacgaagttc    7140
ctattccgaa gttcctattc tccagaaagt ataggaactt ctgtacacct gagctgattc    7200
cgatgacttc gtaggttcct agctcaagcc gctcgtgtcc aagcgtcact tacgattagc    7260
taatgattac ggcatctagg accgactagc taactaacta gtacgtagaa ttaattcatt    7320
ccgattaatc gtggcctctt gctcttcagg atgaagagct atgtttaaac gtgcaagcgc    7380
tactagacaa ttcagtacat taaaaacgtc cgcaatgtgt tattaagttg tctaagcgtc    7440
aatttgttta caccacaata tatcctgcca                                    7470
```

<210> SEQ ID NO 6
<211> LENGTH: 7436
<212> TYPE: DNA
<213> ORGANISM: Artificial Sequence
<220> FEATURE:
<223> OTHER INFORMATION: INSERT DNA

<400> SEQUENCE: 6

```
tcaaacactg atagtttaaa ctgaaggcgg gaaacgacaa tctgatcatg agcggagaat      60
taagggagtc acgttatgac ccccgccgat gacgcgggac aagccgtttt acgtttggaa     120
ctgacagaac cgcaacgttg aaggagccac tcagcaagct ggtacgattg taatacgact     180
cactataggg cgaattgagc gctgtttaaa cgctcttcaa ctggaagagc ggttactacc     240
ggctggatgg cggggccttg atcgtgcacc gccggcgtcc ggactaacta actagtcgag     300
ctagttaccc tatgaggtga catgaagcgc tcacggttac tatgacggtt agcttcacga     360
ctgttggtgg cagtagcgta cgacttagct atagttccgg acttacccctt aagataactt     420
cgtatagcat acattatacg aagttatggg cccaccggtg gtaccgagct cgtttaaacg     480
ctcttcaact ggaagagcgg ttaccagagc tggtcacctt tgtccaccaa gatggaactg     540
```

-continued

```
gcgcgcctca ttaattaagt cagcggccgc tctagttgaa gacacgttca tgtcttcatc    600
gtaagaagac actcagtagt cttcggccag aatggccatc tggattcagc aggcctagaa    660
ggccatttat cgctatcaac tttgtataga aaagttgggc cgaattcgag ctcggtacgg    720
ccagaatggc cctggtaatt attggctgta ggattctaaa cagagcctaa atagctggaa    780
tagctctagc cctcaatcca aactaatgat atctatactt atgcaactct aaattttat    840 tctaaaagta atatttcatt tttgtcaacg agattctcta ctctattcca caatcttttg    900
aagcaatatt taccttaaat ctgtactcta taccaataat catatattct attatttatt    960
tttatctctc tcctaaggag catcccccta tgtctgcatg gcccccgcct cgggtcccaa   1020
tctcttgctc tgctagtagc acagaagaaa acactagaaa tgacttgctt gacttagagt   1080
atcagataaa catcatgttt acttaacttt aatttgtatc ggtttctact atttttataa   1140
tatttttgtc tctatagata ctacgtgcaa cagtataatc aacctagttt aatccagagc   1200
gaaggatttt ttactaagta cgtgactcca tatgcacagc gttccttta tggttcctca   1260 ctgggcacag cataaacgaa ccctgtccaa tgttttcagc gcgaacaaac agaaattcca   1320
tcagcgaaca acaacatac atgcgagatg aaaataaata ataaaaaaag ctccgtctcg    1380
ataggccggc acgaatcgag agcctccata gccagttttt tccatcggaa cggcggttcg   1440
cgcacctaat tatatgcacc acacgccat aaagccaacc aacccgtcgg aggggcgcaa    1500
gccagacaga agacagcccg tcagcccctc tcgttttca tccgccttcg cctccaaccg    1560
cgtgcgctcc acgcctcctc caggaaagcg aggatctccc ccaaatccac ccgtcggcac   1620
ctccgcttca aggtacgccg ctcgtcctcc cccccccccc tctctacctt ctctagatcg   1680
gcgttccggt ccatgcatgg ttagggcccg gtagttctac ttctgttcat gtttgtgtta   1740
gatccgtgtt tgtgttagat ccgtgctgct agcgttcgta cacggatgcg acctgtacgt   1800
cagacacgtt ctgattgcta acttgccagt gtttctcttt ggggaatcct gggatggctc   1860
tagccgttcc gcagacggga tcgatttcat gattttttt gtttcgttgc atagggtttg    1920
gtttgccctt ttcctttatt tcaatatatg ccgtgcactt gtttgtcggg tcatctttc    1980 atgctttttt ttgtcttggt tgtgatgatg tggtctggtt gggcggtcgt tctagatcgg   2040
agtagaattc tgtttcaaac tacctggtgg atttattaat tttggatctg tatgtgtgtg   2100
ccatacatat tcatagttac gaattgaaga tgatggatgg aaatatcgat ctaggatagg   2160
tatacatgtt gatgcgggtt ttactgatgc atatacagag atgcttttg ttcgcttggt    2220 tgtgatgatg tggtgtggtt gggcggtcgt tcattcgttc tagatcggag tagaatactg   2280
tttcaaacta cctggtgtat ttattaattt tggaactgta tgtgtgtgtc atacatcttc   2340
atagttacga gtttaagatg gatggaaata tcgatctagg ataggtatac atgttgatgt   2400 gggtttact gatgcatata catgatggca tatgcagcat ctattcatat gctctaacct    2460
tgagtaccta tctattataa taaacaagta tgttttataa ttatttgat cttgatatac    2520 ttggatgatg gcatatgcag cagctatatg tggattttt tagccctgcc ttcatacgct    2580
atttatttgc ttggtactgt ttcttttgtc gatgctcacc ctgttgtttg gtgttacttc   2640
tgcaggtcga ctctaggatc caagcttggc ctagaaggcc agcttcaagt ttgtacaaaa   2700
aagcaggctc cgcggccgcc cccttcccc atcaccattg ctgcgacgag agtgagcggg    2760
agagggtagg tggcgaggcg gcggagatgg ggcggggcc ggtgcagctg cgccggatcg    2820
agaacaagat caaccgccag gtgaccttct ccaagcgccg gaacgggctg ctgaagaagg   2880
```

```
cccacgagat ctccgtgctc tgcgacgcag aggtcgcgct catcgtcttc tccactaagg    2940
ggaagctcta cgagtactct agccattcca gcatggaagg cattcttgag cgttaccagc    3000
gttactcatt tgaagaaagg gcagtactta acccaagtat tgaagaccag gcaaattggg    3060
gagatgaata tgtccggtta aaatccaaac ttgatgcact tcagaagagt caaaggcagc    3120
tgttaggaga acaattgagt tcactgacca taaaagaact ccagcaactg gagcaacaac    3180
tggacagttc tttgaagcat attaggtcaa gaaagaatca gctcatgttc gattcaattt    3240
ccgcgcttca gaaaaggag aaagcactta cagatcaaaa cggtgtcctg caaaagttca    3300
tggaggcaga gaaggagaaa aacaaggctt tgatgaacgc gcagctccgg gagcagcaaa    3360
atggagcatc aacaagctcc ccatcacttt caccaccaat agttccagat tccatgccaa    3420
ctctaaatat agggccatgt caacatagag gggcagcaga atctgagtct gaaccgtctc    3480
ctgctcctgc acaagcaaac aggggcaacc tgccaccatg gatgctccgc actgtcaagt    3540
aacaggtgag gtcttcccag tgtagttttg cagctgatct cgaaagggtg ggcgcgccga    3600
cccagctttc ttgtacaaag tggccgttaa cggatccaga cttgtccatc ttctggattg    3660
gccaacttaa ttaatgtatg aaataaaagg atgcacacat agtgacatgc taatcactat    3720
aatgtgggca tcaaagttgt gtgttatgtg taattactag ttatctgaat aaaagagaaa    3780
gagatcatcc atatttctta tcctaaatga atgtcacgtg tctttataat tctttgatga    3840
accagatgca tttcattaac caaatccata tacatataaa tattaatcat atataattaa    3900
tatcaattgg gttagcaaaa caaatctagt ctaggtgtgt tttgcgaatt gcggcaagct    3960
tgcggccgcc ccgggcaact ttattataca aagttgatag ataaatcctg aggatctggt    4020
cttcctaagg acccgggata tcggaccgat taaactttaa ttcggtccga taacttcgta    4080
tagcatacat tatacgaagt tatacctggt ggcgccgcta gcctgcagtg cagcgtgacc    4140
cggtcgtgcc cctctctaga gataatgagc attgcatgtc taagttataa aaaattacca    4200 catattttt ttgtcacact tgtttgaagt gcagtttatc tatctttata catatattta    4260
aactttactc tacgaataat ataatctata gtactacaat aatatcagtg ttttagagaa    4320
tcatataaat gaacagttag acatggtcta aaggacaatt gagtatttg acaacaggac    4380 tctacagttt tatctttta gtgtgcatgt gttctccttt tttttttgcaa atagcttcac    4440 ctatataata cttcatccat tttattagta catccattta gggtttaggg ttaatggttt    4500
ttatagacta atttttttag tacatctatt ttattctatt ttagcctcta aattaagaaa    4560
actaaaactc tattttagtt ttttttattta ataatttaga tataaaatag aataaaataa    4620
agtgactaaa aattaaacaa atacccttta agaaattaaa aaaactaagg aaacatttt    4680 cttgttcga gtagataatg ccagcctgtt aaacgccgtc gacgagtcta acggacacca    4740
accagcgaac cagcagcgtc gcgtcgggcc aagcgaagca gacggcacgg catctctgtc    4800
gctgcctctg gaccctctc gagagttccg ctccaccgtt ggacttgctc cgctgtcggc    4860
atccagaaat tgcgtggcgg agcggcagac gtgagccggc acggcaggcg gcctcctcct    4920
cctctcacgg caccggcagc tacgggggat tcctttccca ccgctccttc gctttccctt    4980
cctcgcccgc cgtaataaat agacaccccc tccacaccct ctttccccaa cctcgtgttg    5040
ttcggagcgc acacacacac aaccagatct cccccaaatc cacccgtcgg cacctccgct    5100
tcaaggtacg ccgctcgtcc tccccccccc ccctctctac cttctctaga tcggcgttcc    5160
ggtccatgca tggttagggc ccggtagttc tacttctgtt catgtttgtg ttagatccgt    5220
gtttgtgtta gatccgtgct gctagcgttc gtacacggat gcgacctgta cgtcagacac    5280
```

-continued

```
gttctgattg ctaacttgcc agtgtttctc tttggggaat cctgggatgg ctctagccgt    5340
tccgcagacg ggatcgattt catgattttt tttgtttcgt tgcatagggt ttggtttgcc    5400
cttttccttt atttcaatat atgccgtgca cttgtttgtc gggtcatctt ttcatgcttt    5460
tttttgtctt ggttgtgatg atgtggtctg gttgggcggt cgttctagat cggagtagaa    5520
ttctgtttca aactacctgg tggatttatt aattttggat ctgtatgtgt gtgccataca    5580
tattcatagt tacgaattga agatgatgga tggaaatatc gatctaggat aggtatacat    5640
gttgatgcgg gttttactga tgcatataca gagatgcttt ttgttcgctt ggttgtgatg    5700
atgtggtgtg gttgggcggt cgttcattcg ttctagatcg gagtagaata ctgtttcaaa    5760
ctacctggtg tatttattaa ttttggaact gtatgtgtgt gtcatacatc ttcatagtta    5820
cgagtttaag atggatggaa atatcgatct aggataggta tacatgttga tgtgggtttt    5880
actgatgcat atacatgatg gcatatgcag catctattca tatgctctaa ccttgagtac    5940
ctatctatta taataaacaa gtatgtttta taattatttt gatcttgata tacttggatg    6000
atggcatatg cagcagctat atgtggattt ttttagccct gccttcatac gctatttatt    6060
tgcttggtac tgtttctttt gtcgatgctc accctgttgt ttggtgttac ttctgcaggt    6120
cgactctaga ggatcaattc gctagcgaag ttcctattcc gaagttccta ttctctagaa    6180
agtataggaa cttcagatcc accgggatcc acacgacacc atgtccccg agcgccgccc    6240 cgtcgagatc cgcccggcca ccgccgccga catggccgcc gtgtgcgaca tcgtgaacca    6300
ctacatcgag acctccaccg tgaacttccg caccgagccg cagacccgc aggagtggat    6360 cgacgacctg gagcgcctcc aggaccgcta cccgtggctc gtgccgagg tggagggcgt    6420 ggtggccggc atcgcctacg ccggcccgtg gaaggcccgc aacgcctacg actggaccgt    6480
ggagtccacc gtgtacgtgt cccaccgcca ccagcgcctc ggcctcggct ccaccctcta    6540
cacccacctc ctcaagagca tggaggccca gggcttcaag tccgtggtgg ccgtgatcgg    6600
cctcccgaac gacccgtccg tgcgcctcca cgaggccctc ggctacaccg cccgcggcac    6660
cctccgcgcc gccggctaca agcacggcgg ctggcacgac gtcggcttct ggcagcgcga    6720
cttcgagctg ccggccccgc cgcgcccggt gcgcccggtg acgcagatct gagtcgaaac    6780
ctagacttgt ccatcttctg gattggccaa cttaattaat gtatgaaata aaaggatgca    6840
cacatagtga catgctaatc actataatgt gggcatcaaa gttgtgtgtt atgtgtaatt    6900
actagttatc tgaataaaag agaaagagat catccatatt tcttatccta aatgaatgtc    6960
acgtgtcttt ataattcttt gatgaaccag atgcatttca ttaaccaaat ccatatacat    7020
ataaatatta atcatatata attaatatca attgggttag caaaacaaat ctagtctagg    7080
tgtgttttgc gaatgcggcc ctagcgtata cgaagttcct attccgaagt tcctattctc    7140
cagaaagtat aggaacttct gtacacctga gctgattccg atgacttcgt aggttcctag    7200
ctcaagccgc tcgtgtccaa gcgtcactta cgattagcta atgattacgg catctaggac    7260
cgactagcta actaactagt acgtagaatt aattcattcc gattaatcgt ggcctcttgc    7320
tcttcaggat gaagagctat gtttaaacgt gcaagcgcta ctagacaatt cagtacatta    7380
aaaacgtccg caatgtgtta ttaagttgtc taagcgtcaa tttgtttaca ccacaa       7436
```

<210> SEQ ID NO 7
<211> LENGTH: 10
<212> TYPE: DNA
<213> ORGANISM: Artificial Sequence
<220> FEATURE:

<223> OTHER INFORMATION: JUNCTION SEQUENCE

<400> SEQUENCE: 7
cacactcaaa                                                          10

<210> SEQ ID NO 8
<211> LENGTH: 10
<212> TYPE: DNA
<213> ORGANISM: Artificial Sequence
<220> FEATURE:
<223> OTHER INFORMATION: JUNCTION

<400> SEQUENCE: 8
cacaaagtag                                                          10

<210> SEQ ID NO 9
<211> LENGTH: 20
<212> TYPE: DNA
<213> ORGANISM: Artificial Sequence
<220> FEATURE:
<223> OTHER INFORMATION: JUNCTION

<400> SEQUENCE: 9
aacaacacac tcaaacactg                                               20

<210> SEQ ID NO 10
<211> LENGTH: 20
<212> TYPE: DNA
<213> ORGANISM: Artificial Sequence
<220> FEATURE:
<223> OTHER INFORMATION: JUNCTION

<400> SEQUENCE: 10
tacaccacaa agtagacaag                                               20

<210> SEQ ID NO 11
<211> LENGTH: 30
<212> TYPE: DNA
<213> ORGANISM: Artificial Sequence
<220> FEATURE:
<223> OTHER INFORMATION: JUNCTION

<400> SEQUENCE: 11
gcacaaacaa cacactcaaa cactgatagt                                    30

<210> SEQ ID NO 12
<211> LENGTH: 30
<212> TYPE: DNA
<213> ORGANISM: Artificial Sequence
<220> FEATURE:
<223> OTHER INFORMATION: JUNCTION

<400> SEQUENCE: 12
ttgtttacac cacaaagtag acaagttgtg                                    30

<210> SEQ ID NO 13
<211> LENGTH: 7456
<212> TYPE: DNA
<213> ORGANISM: Artificial Sequence
<220> FEATURE:
<223> OTHER INFORMATION: JUNCTION + INSERT

<400> SEQUENCE: 13
aacaacacac tcaaacactg atagtttaaa ctgaaggcgg gaaacgacaa tctgatcatg    60
agcggagaat taagggagtc acgttatgac ccccgccgat gacgcgggac aagccgtttt   120

```
acgtttggaa ctgacagaac cgcaacgttg aaggagccac tcagcaagct ggtacgattg      180
taatacgact cactataggg cgaattgagc gctgtttaaa cgctcttcaa ctggaagagc      240
ggttactacc ggctggatgg cggggccttg atcgtgcacc gccggcgtcc ggactaacta      300
actagtcgag ctagttaccc tatgaggtga catgaagcgc tcacggttac tatgacggtt      360
agcttcacga ctgttggtgg cagtagcgta cgacttagct atagttccgg acttacccct      420
aagataactt cgtatagcat acattatacg aagttatggg cccaccggtg gtaccgagct      480
cgtttaaacg ctcttcaact ggaagagcgg ttaccagagc tggtcacctt tgtccaccaa      540
gatgaaactg gcgcgcctca ttaattaagt cagcggccgc tctagttgaa gacacgttca      600
tgtcttcatc gtaagaagac actcagtagt cttcggccag aatggccatc tggattcagc      660
aggcctagaa ggccatttat cgctatcaac tttgtataga aaagttgggc gaattcgag      720 ctcggtacgg ccagaatggc cctggtaatt attggctgta ggattctaaa cagagcctaa      780
atagctggaa tagctctagc cctcaatcca aactaatgat atctatactt atgcaactct      840
aaatttttat tctaaaagta atatttcatt tttgtcaacg agattctcta ctctattcca      900
caatcttttg aagcaatatt taccttaaat ctgtactcta taccaataat catatattct      960
attatttatt tttatctctc tcctaaggag catcccccta tgtctgcatg gcccccgcct     1020
cgggtcccaa tctcttgctc tgctagtagc acagaagaaa acactagaaa tgacttgctt     1080
gacttagagt atcagataaa catcatgttt acttaacttt aatttgtatc ggtttctact     1140 attttttataa tattttttgtc tctatagata ctacgtgcaa cagtataatc aacctagttt     1200
aatccagagc gaaggatttt ttactaagta cgtgactcca tatgcacagc gttcctttta     1260
tggttcctca ctgggcacag cataaacgaa ccctgtccaa tgttttcagc gcgaacaaac     1320
agaaattcca tcagcgaaca aacaacatac atgcgagatg aaaataaata ataaaaaaag     1380
ctccgtctcg ataggccggc acgaatcgag agcctccata gccagttttt tccatcggaa     1440
cggcggttcg cgcacctaat tatatgcacc acacgcctat aaagccaacc aacccgtcgg     1500
aggggcgcaa gccagacaga agacagcccg tcagcccctc tcgttttttca tccgccttcg     1560 cctccaaccg cgtgcgctcc acgcctcctc caggaaagcg aggatctccc ccaaatccac     1620
ccgtcggcac ctccgcttca aggtacgccg ctcgtcctcc cccccccccc tctctacctt     1680
ctctagatcg gcgttccggt ccatgcatgg ttagggcccg gtagttctac ttctgttcat     1740
gtttgtgtta gatccgtgtt tgtgttagat ccgtgctgct agcgttcgta cacggatgcg     1800
acctgtacgt cagacacgtt ctgattgcta acttgccagt gtttctcttt ggggaatcct     1860
gggatggctc tagccgttcc gcagacggga tcgatttcat gattttttt gtttcgttgc     1920 atagggtttg gtttgccctt ttcctttatt tcaatatatg ccgtgcactt gtttgtcggg     1980 tcatctttc atgctttttt ttgtcttggt tgtgatgatg tggtctggtt gggcggtcgt     2040 tctagatcg agtagaattc tgtttcaaac tacctggtgg atttattaat tttgatctg      2100 tatgtgtgtg ccatacatat tcatagttac gaattgaaga tgatggatgg aaatatcgat     2160
ctaggatagg tatacatgtt gatgcgggtt ttactgatgc atatacagag atgcttttg      2220 ttcgcttggt tgtgatgatg tggtgtggtt gggcggtcgt tcattcgttc tagatcggag     2280
tagaatactg tttcaaacta cctggtgtat ttattaattt tggaactgta tgtgtgtgtc     2340
atacatcttc atagttacga gtttaagatg gatggaaata tcgatctagg ataggtatac     2400
atgttgatgt gggttttact gatgcatata catgatggca tatgcagcat ctattcatat     2460
```

```
gctctaacct tgagtaccta tctattataa taaacaagta tgttttataa ttattttgat    2520
cttgatatac ttggatgatg gcatatgcag cagctatatg tggattttttt tagccctgcc    2580
ttcatacgct atttatttgc ttggtactgt ttcttttgtc gatgctcacc ctgttgtttg    2640
gtgttacttc tgcaggtcga ctctaggatc caagcttggc ctagaaggcc agcttcaagt    2700
ttgtacaaaa aagcaggctc cgcggccgcc cccttccccc atcaccattg ctgcgacgag    2760
agtgagcggg agagggtagg tggcgaggcg cggagatgg ggcgggggcc ggtgcagctg      2820
cgccggatcg agaacaagat caaccgccag gtgaccttct ccaagcgccg gaacgggctg    2880
ctgaagaagg cccacgagat ctccgtgctc tgcgacgcag aggtcgcgct catcgtcttc    2940
tccactaagg ggaagctcta cgagtactct agccattcca gcatggaagg cattcttgag    3000
cgttaccagc gttactcatt tgaagaaagg gcagtactta acccaagtat tgaagaccag    3060
gcaaattggg gagatgaata tgtccggtta aaatccaaac ttgatgcact tcagaagagt    3120
caaaggcagc tgttaggaga acaattgagt tcactgacca taaaagaact ccagcaactg    3180
gagcaacaac tggacagttc tttgaagcat attaggtcaa gaaagaatca gctcatgttc    3240
gattcaattt ccgcgcttca gaaaaggag aaagcactta cagatcaaaa cggtgtcctg     3300
caaaagttca tggaggcaga gaaggagaaa acaaggctt tgatgaacgc gcagctccgg      3360
gagcagcaaa atggagcatc aacaagctcc ccatcacttt caccaccaat agttccagat    3420
tccatgccaa ctctaaatat agggccatgt caacatagag gggcagcaga atctgagtct    3480
gaaccgtctc ctgctcctgc acaagcaaac aggggcaacc tgccaccatg gatgctccgc    3540
actgtcaagt aacaggtgag gtcttcccag tgtagttttg cagctgatct cgaaagggtg    3600
ggcgcgccga cccagctttc ttgtacaaag tggccgttaa cggatccaga cttgtccatc    3660
ttctggattg gccaacttaa ttaatgtatg aaataaaagg atgcacacat agtgacatgc    3720
taatcactat aatgtgggca tcaaagttgt gtgttatgtg taattactag ttatctgaat    3780
aaaagagaaa gagatcatcc atatttctta tcctaaatga atgtcacgtg tctttataat    3840
tctttgatga accagatgca tttcattaac caaatccata tacatataaa tattaatcat    3900
atataattaa tatcaattgg gttagcaaaa caaatctagt ctaggtgtgt tttgcgaatt    3960
gcggcaagct tgcggccgcc ccgggcaact ttattataca aagttgatag ataaatcctg    4020
aggatctggt cttcctaagg acccgggata tcggaccgat taaactttaa ttcggtccga    4080
taacttcgta tagcatacat tatacgaagt tatacctggt ggcgccgcta gcctgcagtg    4140
cagcgtgacc cggtcgtgcc cctctctaga gataatgagc attgcatgtc taagttataa    4200
aaaattacca catatttttt ttgtcacact tgtttgaagt gcagtttatc tatctttata    4260
catatattta aactttactc tacgaataat ataatctata gtactacaat aatatcagtg    4320
ttttagagaa tcatataaat gaacagttag acatggtcta aaggacaatt gagtattttg    4380
acaacaggac tctacagttt tatctttta gtgtgcatgt gttctccttt ttttttgcaa     4440
atagcttcac ctatataata cttcatccat tttattagta catccattta gggtttaggg    4500
ttaatggttt ttatagacta atttttttag tacatctatt ttattctatt tagcctcta     4560
aattaagaaa actaaaactc tattttagtt tttttattta ataatttaga tataaaatag    4620
aataaaataa agtgactaaa aattaaacaa ataccctta agaaattaaa aaactaagg      4680
aaacattttt cttgtttcga gtagataatg ccagcctgtt aaacgccgtc gacgagtcta    4740
acggacacca accagcgaac cagcagcgtc gcgtcgggcc aagcgaagca gacggcacgg    4800
catctctgtc gctgcctctg gaccctctc gagagttccg ctccaccgtt ggacttgctc      4860
```

```
cgctgtcggc atccagaaat tgcgtggcgg agcggcagac gtgagccggc acggcaggcg    4920
gcctcctcct cctctcacgg caccggcagc tacggggat tcctttccca ccgctccttc     4980
gctttccctt cctcgcccgc cgtaataaat agacaccccc tccacaccct ctttccccaa    5040
cctcgtgttg ttcggagcgc acacacacac aaccagatct cccccaaatc cacccgtcgg    5100
cacctccgct tcaaggtacg ccgctcgtcc tcccccccc ccctctctac cttctctaga     5160
tcggcgttcc ggtccatgca tggttagggc ccggtagttc tacttctgtt catgtttgtg    5220
ttagatccgt gtttgtgtta gatccgtgct gctagcgttc gtacacggat gcgacctgta    5280
cgtcagacac gttctgattg ctaacttgcc agtgtttctc tttggggaat cctgggatgg    5340
ctctagccgt tccgcagacg ggatcgattt catgattttt tttgtttcgt tgcatagggt    5400
ttggtttgcc ctttccttt atttcaatat atgccgtgca cttgtttgtc gggtcatctt     5460
ttcatgcttt ttttgtctt ggttgtgatg atgtggtctg gttgggcggt cgttctagat     5520
cggagtagaa ttctgtttca aactaccgg tggatttatt aattttggat ctgtatgtgt     5580
gtgccataca tattcatagt tacgaattga agatgatgga tggaaatatc gatctaggat    5640
aggtatacat gttgatgcgg gttttactga tgcatataca gagatgcttt ttgttcgctt    5700
ggttgtgatg atgtggtgtg gttgggcggt cgttcattcg ttctagatcg gagtagaata    5760
ctgtttcaaa ctacctggtg tatttattaa ttttggaact gtatgtgtgt gtcatacatc    5820
ttcatagtta cgagtttaag atggatggaa atatcgatct aggataggta tacatgttga    5880
tgtgggtttt actgatgcat atacatgatg gcatatgcag catctattca tatgctctaa    5940
ccttgagtac ctatctatta taataaacaa gtatgtttta taattatttt gatcttgata    6000
tacttggatg atggcatatg cagcagctat atgtggattt ttttagccct gccttcatac    6060
gctatttatt tgcttggtac tgtttctttt gtcgatgctc accctgttgt ttggtgttac    6120
ttctgcaggt cgactctaga ggatcaattc gctagcgaag ttcctattcc gaagttccta    6180
ttctctagaa agtataggaa cttcagatcc accgggatcc acacgacacc atgtcccccg    6240
agcgccgccc cgtcgagatc cgcccggcca ccgccgccga catggccgcc gtgtgcgaca    6300
tcgtgaacca ctacatcgag acctccaccg tgaacttccg caccgagccg cagacccgc    6360 aggagtggat cgacgacctg agcgcctcc aggaccgcta cccgtggctc gtggccgagg    6420
tggagggcgt ggtggccggc atcgcctacg ccggcccgtg gaaggcccgc aacgcctacg    6480
actggaccgt ggagtccacc gtgtacgtgt cccaccgcca ccagcgcctc ggcctcggct    6540
ccaccctcta cacccacctc ctcaagagca tggaggccca gggcttcaag tccgtggtgg    6600
ccgtgatcgg cctcccgaac gacccgtccg tgcgcctcca cgaggccctc ggctacaccg    6660
cccgcggcac cctccgcgcc gccggctaca agcacgcgg ctggcacgac gtcggcttct    6720
ggcagcgcga cttcgagctg ccggccccgc cgcgcccggt gcgcccggtg acgcagatct    6780
gagtcgaaac ctagacttgt ccatcttctg gattggccaa cttaattaat gtatgaaata    6840
aaaggatgca cacatagtga catgctaatc actataatgt gggcatcaaa gttgtgtgtt    6900
atgtgtaatt actagttatc tgaataaaag agaaagagat catccatatt tcttatccta    6960
aatgaatgtc acgtgtcttt ataattcttt gatgaaccag atgcatttca ttaaccaaat    7020
ccatatacat ataaatatta atcatatata attaatatca attgggttag caaaacaaat    7080
ctagtctagg tgtgttttgc gaatgcggcc ctagcgtata cgaagttcct attccgaagt    7140
tcctattctc cagaaagtat aggaacttct gtacacctga gctgattccg atgacttcgt    7200
```

| | | | |
|---|---|---|---|
| aggttcctag | ctcaagccgc | tcgtgtccaa gcgtcactta cgattagcta atgattacgg | 7260 |
| catctaggac | cgactagcta | actaactagt acgtagaatt aattcattcc gattaatcgt | 7320 |
| ggcctcttgc | tcttcaggat | gaagagctat gtttaaacgt gcaagcgcta ctagacaatt | 7380 |
| cagtacatta | aaaacgtccg | caatgtgtta ttaagttgtc taagcgtcaa tttgtttaca | 7440 |
| ccacaaagta | gacaag | | 7456 |

```
<210> SEQ ID NO 14
<211> LENGTH: 7476
<212> TYPE: DNA
<213> ORGANISM: Artificial Sequence
<220> FEATURE:
<223> OTHER INFORMATION: INSERT + JUNCTION

<400> SEQUENCE: 14
```

| | | | |
|---|---|---|---|
| gtacagcaca | aacaacacac | tcaaacactg atagtttaaa ctgaaggcgg gaaacgacaa | 60 |
| tctgatcatg | agcggagaat | taagggagtc acgttatgac ccccgccgat gacgcgggac | 120 |
| aagccgtttt | acgtttggaa | ctgacagaac cgcaacgttg aaggagccac tcagcaagct | 180 |
| ggtacgattg | taatacgact | cactataggg cgaattgagc gctgtttaaa cgctcttcaa | 240 |
| ctggaagagc | ggttactacc | ggctggatgg cggggccttg atcgtgcacc gccggcgtcc | 300 |
| ggactaacta | actagtcgag | ctagttaccc tatgaggtga catgaagcgc tcacggttac | 360 |
| tatgacggtt | agcttcacga | ctgttggtgg cagtagcgta cgacttagct atagttccgg | 420 |
| acttacccct | aagataactt | cgtatagcat acattatacg aagttatggg cccaccggtg | 480 |
| gtaccgagct | cgtttaaacg | ctcttcaact ggaagagcgg ttaccagagc tggtcacctt | 540 |
| tgtccaccaa | gatggaactg | gcgcgcctca ttaattaagt cagcggccgc tctagttgaa | 600 |
| gacacgttca | tgtcttcatc | gtaagaagac actcagtagt cttcggccag aatggccatc | 660 |
| tggattcagc | aggcctagaa | ggccatttat cgctatcaac tttgtataga aagttgggc | 720 |
| cgaattcgag | ctcggtacgg | ccagaatggc cctggtaatt attggctgta ggattctaaa | 780 |
| cagagcctaa | atagctggaa | tagctctagc cctcaatcca aactaatgat atctatactt | 840 |
| atgcaactct | aaattttat | tctaaaagta atatttcatt tttgtcaacg agattctcta | 900 |
| ctctattcca | caatcttttg | aagcaatatt taccttaaat ctgtactcta taccaataat | 960 |
| catatattct | attatttatt | tttatctctc tcctaaggag catccccta tgtctgcatg | 1020 |
| gcccccgcct | cgggtcccaa | tctcttgctc tgctagtagc acagaagaaa acactagaaa | 1080 |
| tgacttgctt | gacttagagt | atcagataaa catcatgttt acttaacttt aatttgtatc | 1140 |
| ggtttctact | attttttataa | tattttgtc tctatagata ctacgtgcaa cagtataatc | 1200 |
| aacctagttt | aatccagagc | gaaggatttt ttactaagta cgtgactcca tatgcacagc | 1260 |
| gttcctttta | tggttcctca | ctgggcacag cataaacgaa ccctgtccaa tgttttcagc | 1320 |
| gcgaacaaac | agaaattcca | tcagcgaaca acaacatac atgcgagatg aaaataaata | 1380 |
| ataaaaaaag | ctccgtctcg | ataggccggc acgaatcgag agcctccata gccagttttt | 1440 |
| tccatcggaa | cggcggttcg | cgcacctaat tatatgcacc acacgcctat aaagccaacc | 1500 |
| aacccgtcgg | aggggcgcaa | gccagacaga agacagcccg tcagccctc tcgttttca | 1560 |
| tccgccttcg | cctccaaccg | cgtgcgctcc acgcctcctc caggaaagcg aggatctccc | 1620 |
| ccaaatccac | ccgtcggcac | ctccgcttca aggtacgccg ctcgtcctcc cccccccccc | 1680 |
| tctctacctt | ctctagatcg | gcgttccggt ccatgcatgg ttagggcccg gtagttctac | 1740 |
| ttctgttcat | gtttgtgtta | gatccgtgtt tgtgttagat ccgtgctgct agcgttcgta | 1800 |

```
cacggatgcg acctgtacgt cagacacgtt ctgattgcta acttgccagt gtttctcttt    1860
ggggaatcct gggatggctc tagccgttcc gcagacggga tcgatttcat gattttttt     1920 gtttcgttgc atagggtttg gtttgcccct ttcctttatt tcaatatatg ccgtgcactt    1980
gtttgtcggg tcatcttttc atgctttttt ttgtcttggt tgtgatgatg tggtctggtt    2040
gggcggtcgt tctagatcgg agtagaattc tgtttcaaac tacctggtgg atttattaat    2100
tttggatctg tatgtgtgtg ccatacatat tcatagttac gaattgaaga tgatggatgg    2160
aaatatcgat ctaggatagg tatacatgtt gatgcgggtt ttactgatgc atatacagag    2220 atgcttttg ttcgcttggt tgtgatgatg tggtgtggtt gggcggtcgt tcattcgttc     2280
tagatcggag tagaatactg tttcaaacta cctggtgtat ttattaattt tggaactgta    2340
tgtgtgtgtc atacatcttc atagttacga gtttaagatg gatggaaata tcgatctagg    2400
ataggtatac atgttgatgt gggttttact gatgcatata catgatggca tatgcagcat    2460
ctattcatat gctctaacct tgagtaccta tctattataa taaacaagta tgttttataa    2520
ttattttgat cttgatatac ttggatgatg gcatatgcag cagctatatg tggatttttt    2580
tagccctgcc ttcatacgct atttatttgc ttggtactgt ttcttttgtc gatgctcacc    2640
ctgttgtttg gtgttacttc tgcaggtcga ctctaggatc caagcttggc ctagaaggcc    2700
agcttcaagt ttgtacaaaa aagcaggctc cgcggccgcc cccttccccc atcaccattg    2760
ctgcgacgag agtgagcggg agagggtagg tggcgaggcg gcggagatgg ggcggggcc     2820 ggtgcagctg cgccggatcg agaacaagat caaccgccag gtgaccttct ccaagcgccg    2880
gaacgggctg ctgaagaagg cccacgagat ctccgtgctc tgcgacgcag aggtcgcgct    2940
catcgtcttc tccactaagg ggaagctcta cgagtactct agccattcca gcatggaagg    3000
cattcttgag cgttaccagc gttactcatt tgaagaaagg gcagtactta acccaagtat    3060
tgaagaccag gcaaattggg gagatgaata tgtccggtta aaatccaaac ttgatgcact    3120
tcagaagagt caaaggcagc tgttaggaga acaattgagt tcactgacca taaaagaact    3180
ccagcaactg gagcaacaac tggacagttc tttgaagcat attaggtcaa gaaagaatca    3240
gctcatgttc gattcaattt ccgcgcttca gaaaaaggag aaagcactta cagatcaaaa    3300
cggtgtcctg caaaagttca tggaggcaga aaggagaaa acaaggctt tgatgaacgc      3360 gcagctccgg gagcagcaaa atggagcatc aacaagctcc ccatcacttt caccaccaat    3420
agttccagat tccatgccaa ctctaaatat agggccatgt caacatagag gggcagcaga    3480
atctgagtct gaaccgtctc ctgctcctgc acaagcaaac aggggcaacc tgccaccatg    3540
gatgctccgc actgtcaagt aacaggtgag gtcttcccag tgtagttttg cagctgatct    3600
cgaaagggtg ggcgcgccga cccagctttc ttgtacaaag tggccgttaa cggatccaga    3660
cttgtccatc ttctggattg gccaacttaa ttaatgtatg aaataaaagg atgcacacat    3720
agtgacatgc taatcactat aatgtgggca tcaaagttgt gtgttatgtg taattactag    3780
ttatctgaat aaaagagaaa gagatcatcc atatttctta tcctaaatga atgtcacgtg    3840
tctttataat tctttgatga accagatgca tttcattaac caaatccata tacatataaa    3900
tattaatcat atataattaa tatcaattgg gttagcaaaa caaatctagt ctaggtgtgt    3960
tttgcgaatt gcggcaagct tgcggccgcc ccgggcaact ttattataca agttgatag     4020 ataaatcctg aggatctggt cttcctaagg acccgggata tcggaccgat taaactttaa    4080
ttcggtccga taacttcgta tagcatacat tatacgaagt tatacctggt ggcgccgcta    4140
```

-continued

```
gcctgcagtg cagcgtgacc cggtcgtgcc cctctctaga gataatgagc attgcatgtc    4200
taagttataa aaaattacca catattttt ttgtcacact tgtttgaagt gcagtttatc     4260
tatctttata catatattta aactttactc tacgaataat ataatctata gtactacaat    4320
aatatcagtg ttttagagaa tcatataaat gaacagttag acatggtcta aaggacaatt    4380
gagtattttg acaacaggac tctacagttt tatcttttta gtgtgcatgt gttctccttt    4440 tttttttgcaa atagcttcac ctatataata cttcatccat tttattagta catccattta   4500
gggtttaggg ttaatggttt ttatagacta attttttag tacatctatt ttattctatt     4560
ttagcctcta aattaagaaa actaaaactc tattttagtt tttttattta ataatttaga    4620
tataaaatag aataaaataa agtgactaaa aattaaacaa atacccttta agaaattaaa    4680
aaaactaagg aaacatttttt cttgtttcga gtagataatg ccagcctgtt aaacgccgtc   4740
gacgagtcta acggacacca accagcgaac cagcagcgtc gcgtcgggcc aagcgaagca    4800
gacggcacgg catctctgtc gctgcctctg gacccctctc gagagttccg ctccaccgtt    4860
ggacttgctc cgctgtcggc atccagaaat tgcgtggcgg agcggcagac gtgagccggc    4920
acggcaggcg gcctcctcct cctctcacgg caccggcagc tacggggat tcctttccca     4980 ccgctccttc gctttccctt cctcgcccgc cgtaataaat agacaccccc tccacaccct    5040
ctttccccaa cctcgtgttg ttcggagcgc acacacacac aaccagatct cccccaaatc    5100
cacccgtcgg cacctccgct tcaaggtacg ccgctcgtcc tcccccccc cctctctac      5160 cttctctaga tcggcgttcc ggtccatgca tggttagggc ccggtagttc tacttctgtt    5220
catgtttgtg ttagatccgt gtttgtgtta gatccgtgct gctagcgttc gtacacggat    5280
gcgacctgta cgtcagacac gttctgattg ctaacttgcc agtgtttctc tttggggaat    5340
cctgggatgg ctctagccgt tccgcagacg ggatcgattt catgattttt tttgtttcgt    5400
tgcatagggt ttggtttgcc cttttccttt atttcaatat atgccgtgca cttgtttgtc    5460
gggtcatctt ttcatgcttt tttttgtctt ggttgtgatg atgtggtctg gttgggcggt    5520
cgttctagat cggagtagaa ttctgtttca aactacctgg tggatttatt aattttggat    5580
ctgtatgtgt gtgccataca tattcatagt tacgaattga agatgatgga tggaaatatc    5640
gatctaggat aggtatacat gttgatgcgg gttttactga tgcatataca gagatgcttt    5700
ttgttcgctt ggttgtgatg atgtggtgtg gttgggcggt cgttcattcg ttctagatcg    5760
gagtagaata ctgtttcaaa ctacctggtg tatttattaa ttttggaact gtatgtgtgt    5820
gtcatacatc ttcatagtta cgagtttaag atggatggaa atatcgatct aggataggta    5880
tacatgttga tgtgggtttt actgatgcat atacatgatg gcatatgcag catctattca    5940
tatgctctaa ccttgagtac ctatctatta aataaacaa gtatgtttta taattatttt     6000
gatcttgata tacttggatg atggcatatg cagcagctat atgtggattt ttttagccct    6060
gccttcatac gctatttatt tgcttggtac tgtttctttt gtcgatgctc accctgttgt    6120
ttggtgttac ttctgcaggt cgactctaga ggatcaattc gctagcgaag ttcctattcc    6180
gaagttccta ttctctagaa agtataggaa cttcagatcc accgggatcc acacgacacc    6240
atgtcccccg agcgccgccc cgtcgagatc cgccggcca ccgccgccga catgccgcc      6300 gtgtgcgaca tcgtgaacca ctacatcgag acctccaccg tgaacttccg caccgagccg    6360 cagacccgc aggagtggat cgacgacctg gagcgcctcc aggaccgcta cccgtggctc    6420
gtggccgagg tggagggcgt ggtggccggc atcgcctacg ccggcccgtg gaaggccgc    6480 aacgcctacg actggaccgt ggagtccacc gtgtacgtgt cccaccgcca ccagcgcctc    6540
```

-continued

```
ggcctcggct ccaccctcta cacccacctc ctcaagagca tggaggccca gggcttcaag    6600
tccgtggtgg ccgtgatcgg cctcccgaac gacccgtccg tgcgcctcca cgaggccctc    6660
ggctacaccg cccgcggcac cctccgcgcc gccggctaca agcacggcgg ctggcacgac    6720
gtcggcttct ggcagcgcga cttcgagctg ccggcccgc cgcgcccggt gcgcccggtg    6780
acgcagatct gagtcgaaac ctagacttgt ccatcttctg gattggccaa cttaattaat    6840
gtatgaaata aaaggatgca cacatagtga catgctaatc actataatgt gggcatcaaa    6900
gttgtgtgtt atgtgtaatt actagttatc tgaataaaag agaaagagat catccatatt    6960
tcttatccta aatgaatgtc acgtgtcttt ataattcttt gatgaaccag atgcatttca    7020
ttaaccaaat ccatatacat ataaatatta atcatatata attaatatca attgggttag    7080
caaaacaaat ctagtctagg tgtgttttgc gaatgcggcc ctagcgtata cgaagttcct    7140
attccgaagt tcctattctc cagaaagtat aggaacttct gtacacctga gctgattccg    7200
atgacttcgt aggttcctag ctcaagccgc tcgtgtccaa gcgtcactta cgattagcta    7260
atgattacgg catctaggac cgactagcta actaactagt acgtagaatt aattcattcc    7320
gattaatcgt ggcctcttgc tcttcaggat gaagagctat gtttaaacgt gcaagcgcta    7380
ctagacaatt cagtacatta aaaacgtccg caatgtgtta ttaagttgtc taagcgtcaa    7440
tttgtttaca ccacaaagta gacaagttgt gttcaa                              7476
```

<210> SEQ ID NO 15
<211> LENGTH: 23
<212> TYPE: DNA
<213> ORGANISM: Artificial Sequence
<220> FEATURE:
<223> OTHER INFORMATION: Oligonucleotide

<400> SEQUENCE: 15

```
ccatctgagg tctgcactct cac                                            23
```

<210> SEQ ID NO 16
<211> LENGTH: 22
<212> TYPE: DNA
<213> ORGANISM: Artificial Sequence
<220> FEATURE:
<223> OTHER INFORMATION: OLIGONUCLEOTIDE

<400> SEQUENCE: 16

```
ctccgctcat gatcagattg tc                                             22
```

<210> SEQ ID NO 17
<211> LENGTH: 15
<212> TYPE: DNA
<213> ORGANISM: Artificial Sequence
<220> FEATURE:
<223> OTHER INFORMATION: Probe

<400> SEQUENCE: 17

```
aacacactca aacac                                                     15
```

<210> SEQ ID NO 18
<211> LENGTH: 19
<212> TYPE: DNA
<213> ORGANISM: Artificial Sequence
<220> FEATURE:
<223> OTHER INFORMATION: Oligonucleotide

<400> SEQUENCE: 18
ggatgctccg cactgtcaa                                                                  19

<210> SEQ ID NO 19
<211> LENGTH: 18
<212> TYPE: DNA
<213> ORGANISM: Artificial Sequence
<220> FEATURE:
<223> OTHER INFORMATION: Oligonucleotide

<400> SEQUENCE: 19
aagaaagctg ggtcggcg                                                                   18

<210> SEQ ID NO 20
<211> LENGTH: 14
<212> TYPE: DNA
<213> ORGANISM: Artificial Sequence
<220> FEATURE:
<223> OTHER INFORMATION: Probe

<400> SEQUENCE: 20
tctcgaaagg gtgg                                                                       14

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
catcgtgaac cactacatcg agac                                                            24

<210> SEQ ID NO 22
<211> LENGTH: 18
<212> TYPE: DNA
<213> ORGANISM: Artificial Sequence
<220> FEATURE:
<223> OTHER INFORMATION: Oligonucleotide

<400> SEQUENCE: 22
gtcgatccac tcctgcgg                                                                   18

<210> SEQ ID NO 23
<211> LENGTH: 22
<212> TYPE: DNA
<213> ORGANISM: Artificial Sequence
<220> FEATURE:
<223> OTHER INFORMATION: Probe

<400> SEQUENCE: 23
accgtgaact tccgcaccga gc                                                              22

<210> SEQ ID NO 24
<211> LENGTH: 105
<212> TYPE: DNA
<213> ORGANISM: Artificial Sequence
<220> FEATURE:
<223> OTHER INFORMATION: Amplicon

<400> SEQUENCE: 24
ccatctgagg tctgcactct caccggtagt acagcacaaa caacacactc aaacactgat            60
agtttaaact gaaggcggga aacgacaatc tgatcatgag cggag                           105

<210> SEQ ID NO 25
<211> LENGTH: 93

<212> TYPE: DNA
<213> ORGANISM: Artificial Sequence
<220> FEATURE:
<223> OTHER INFORMATION: Amplicon

<400> SEQUENCE: 25
ggatgctccg cactgtcaag taacaggtga ggtcttccca gtgtagtttt gcagctgatc    60
tcgaaagggt gggcgcgccg acccagcttt ctt    93

<210> SEQ ID NO 26
<211> LENGTH: 76
<212> TYPE: DNA
<213> ORGANISM: Artificial Sequence
<220> FEATURE:
<223> OTHER INFORMATION: Amplicon

<400> SEQUENCE: 26
catcgtgaac cactacatcg agacctccac cgtgaacttc cgcaccgagc cgcagacccc    60
gcaggagtgg atcgac    76

<210> SEQ ID NO 27
<211> LENGTH: 23
<212> TYPE: DNA
<213> ORGANISM: Artificial Sequence
<220> FEATURE:
<223> OTHER INFORMATION: Oligo

<400> SEQUENCE: 27
ttggactaga aatctcgtgc tga    23

<210> SEQ ID NO 28
<211> LENGTH: 22
<212> TYPE: DNA
<213> ORGANISM: Artificial Sequence
<220> FEATURE:
<223> OTHER INFORMATION: Oligo

<400> SEQUENCE: 28
gctacatagg gagccttgtc ct    22

<210> SEQ ID NO 29
<211> LENGTH: 16
<212> TYPE: DNA
<213> ORGANISM: Artificial Sequence
<220> FEATURE:
<223> OTHER INFORMATION: Probe

<400> SEQUENCE: 29
gcgtttgtgt ggattg    16

<210> SEQ ID NO 30
<211> LENGTH: 79
<212> TYPE: DNA
<213> ORGANISM: Artificial Sequence
<220> FEATURE:
<223> OTHER INFORMATION: Amplicon

<400> SEQUENCE: 30
ttggactaga aatctcgtgc tgattaattg ttttacgcgt gcgtttgtgt ggattgtagg    60
acaaggctcc ctatgtagc    79

<210> SEQ ID NO 31
<211> LENGTH: 435
<212> TYPE: DNA

```
<213> ORGANISM: Artificial Sequence
<220> FEATURE:
<223> OTHER INFORMATION: Junction

<400> SEQUENCE: 31
tacttatatg ggctctgccg ttggagatga tgggcaaggc cttccgagga gccgagatga      60
ggatttaggc cttccattga gttgcgctcg ggccgtcctc ggtggcacga accagtgggc     120
caacggggcc aacgggccta actaatcgtg tctgatggat ggtcctccgt tccagagaaa     180
tcagacctgc tggctgtggg cctgtggctg aggagccggc agtgatccat cgagtgctac     240
tgttttcttt tttcagaaca gcgtgcagca aaggctcact gtgcagttta aacacctaaa     300
agacccgaca agtcggtgtt ggtactgagg acgaacccag accgaatgat tgcctcgccc     360
tcaccaccta tttcttccca tctgaggtct gcactctcac cggtagtaca gcacaaacaa     420
cacactcaaa cactg                                                      435

<210> SEQ ID NO 32
<211> LENGTH: 417
<212> TYPE: DNA
<213> ORGANISM: Artificial Sequence
<220> FEATURE:
<223> OTHER INFORMATION: Junction

<400> SEQUENCE: 32
tacaccacaa agtagacaag ttgtgttcaa accgcggatc agaaacaaat aaagcgaccc      60
cgcatgcacg tcaggtacca acccaaatcg ggaccctccc cccggctccg gccggtgtct     120
cccaagttaa acggccgccc gcgccaataa ttaccaccac accccggtag agagatggag     180
tagaagaaga aaaaaaatca tccgccaagc cgcgatccgc gaccgcagcg catcgacggc     240
gcacccccct cccctccggt cgtcggtcca cagcagacag gccgcgtcat tgcagattac     300
tgcaccaccg catcgcatca tcgcagcggc ccgcatgaac gaacacgagc ccccattttc     360
cgcgcgggtt gccgagccgg cagcccagcg cggacacggg gagctagcgg cggtcag       417
```